United States Patent
Asai et al.

[11] Patent Number: 6,087,379
[45] Date of Patent: Jul. 11, 2000

[54] CYCLIC AMINE DERIVATIVES

[75] Inventors: Fumitoshi Asai, Tanashi; Atsuhiro Sugidachi, Kawasaki; Toshihiko Ikeda, Yokohama; Hiroyuki Koike, Tokyo; Teruhiko Inoue, Ube; Katsunori Takata, Yamaguchi; Ryo Iwamura, Ube; Jun-ichiro Kita, Ube; Kenji Yoneda, Ube, all of Japan

[73] Assignees: Sankyo Company, Limited, Tokyo; Ube Industries, Ltd., Ube, both of Japan

[21] Appl. No.: 09/257,818

[22] Filed: Feb. 25, 1999

Related U.S. Application Data

[63] Continuation of application No. PCT/JP97/02990, Aug. 28, 1997.

[30] Foreign Application Priority Data

Aug. 28, 1996 [JP] Japan .................. 8-226507

[51] Int. Cl.$^7$ .................. A61K 31/445; A61K 31/46; A61K 31/40; C07D 211/54; C07D 207/12; C07D 205/04
[52] U.S. Cl. .................. 514/327; 514/210; 514/212; 514/227.5; 514/231.5; 514/255; 514/299; 514/304; 514/424; 540/604; 544/59; 544/158; 544/384; 546/112; 546/129; 546/221; 548/556; 548/952; 548/965
[58] Field of Search .................. 546/221, 112, 546/129; 514/327, 304, 299, 424, 210, 212, 227.5, 231.2, 255; 548/556, 952, 965; 540/604; 544/59, 158, 384

[56] References Cited

U.S. PATENT DOCUMENTS

| | | | |
|---|---|---|---|
| 4,051,141 | 9/1977 | Castaigne | 260/294.8 |
| 4,529,596 | 7/1985 | Aubert et al. | 514/231 |
| 4,740,510 | 4/1988 | Badore et al. | 514/291 |
| 5,556,854 | 9/1996 | Furrer et al. | 514/234.2 |

FOREIGN PATENT DOCUMENTS

| | | |
|---|---|---|
| 9222847 | 3/1993 | Austria . |
| WO 93/14077 | 7/1993 | WIPO . |
| WO 95/07691 | 3/1995 | WIPO . |

OTHER PUBLICATIONS

A. Anderson, Jr. et al, "The Synthesis of Azetidine–3–Carboxylic Acid", *J. Org. Chem.*, vol. 37, No. 24, pp. 3953–3955 (1972).

P. Lumley et al, "A Method for Quantitating Platelet Aggregation and Analyzing Drug–Receptor Interactions on Platelets in Whole Blood in Vitro", *J. Pharmacol. Methods*, vol. 6, pp. 153–166 (1981).

G.V.R. Born, "Aggregation of Blood Platelets by Adenosine Diphosphate and its Reversal", *Nature*, vol. 194, No. 4832, pp. 927–929 (Jun. 1962).

*Primary Examiner*—Evelyn Mei Huang
*Attorney, Agent, or Firm*—Frishauf, Holtz, Goodman, Langer & Chick, P.C.

[57] ABSTRACT

A cyclic amine derivative represented by the following formula:

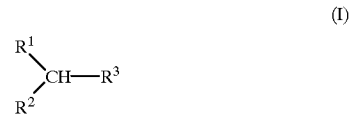

(I)

wherein $R^1$ represents a substituted or unsubstituted phenyl group, $R^2$ represents a substituted of unsubstituted $C_1$–$C_8$ aliphatic acyl group, a substituted or unsubstituted benzoyl group or a $C_1$–$C_4$ alkoxycarbonyl group, and $R^3$ represents a substituted 3 to 7 membered saturated cyclic amino group which may form a fused ring; or pharmaceutically acceptable salts thereof. The compounds and salts have excellent platelet aggregation inhibitory action. They are useful for the treatment and prevention of such diseases as embolism, thrombosis or arteriosclerosis and for the preparation of pharmaceutical compositions for such uses.

70 Claims, No Drawings

CYCLIC AMINE DERIVATIVES

This application is a continuation application of International Application PCT/JP97/02990 filed Aug. 28, 1997.

BACKGROUND OF THE INVENTION

The present invention relates to a cyclic amine derivative or pharmaceutically acceptable salt thereof which has excellent platelet aggregation inhibitory action, arteriosclerosis progress inhibitory action or the like and is useful as a therapeutic agent or a preventive agent against embolism, thrombosis or arteriosclerosis; a composition for the prevention or treatment of embolism, thrombosis or arteriosclerosis which comprises the above-described compound as an effective ingredient; use of it for the preparation of a pharmaceutical for the prevention or treatment of the above-described disease; or a method for the treatment or prevention of the above-described disease, which comprises administering a pharmacologically effective amount of the above-described compound to a warm-blooded animal.

As a cyclic amine derivative having platelet aggregation inhibitory action or the like, for example, a hydropyridine derivative is known, ex. U.S. Pat. No. 4,051,141, Japanese Patent Application Kokai No. Sho 59-27895 (EP99802) and Japanese Patent Application Kokai No. Hei 6-41139 (EP542411).

SUMMARY OF THE INVENTION

The present inventors have investigated the pharmacological action of cyclic amine derivatives over long years. As a result, it has been found that specific cyclic amine derivatives have excellent platelet aggregation inhibitory action, arteriosclerosis progress inhibitory action or the like (particularly, platelet aggregation inhibitory action) and is therefore useful as a therapeutic agent or a preventive agent (particularly, therapeutic agent) against embolism, thrombosis or arteriosclerosis (particularly, embolism or thrombosis), leading to the completion of the present invention.

The present invention provides a cyclic amine derivative or a pharmaceutically acceptable salt which has excellent platelet aggregation inhibitory action, arteriosclerosis progress inhibitory action or the like and is useful as a therapeutic agent or a preventive agent against embolism, thrombosis or arteriosclerosis; a composition for the prevention or treatment of embolism, thrombosis or arteriosclerosis which comprises the above-described compound as an effective ingredient; use of the above-described compound for the preparation of a pharmaceutical for the prevention or treatment of the above-described disease; or a method for the prevention or treatment of the above-described disease, which comprises administering a pharmacologically effective amount of the above-described compound to a warm-blooded animal.

The cyclic amine derivative according to the present invention is represented by the following formula:

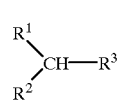

(I)

In the above formula, $R^1$ represents a substituted or unsubstituted phenyl group (the substituent of said phenyl group being a $C_1$–$C_4$ alkyl group, a halogen atom, a fluoro-substituted-($C_1$–$C_4$ alkyl) group, a $C_1$–$C_4$ alkoxy group, a fluoro-substituted-($C_1$–$C_4$ alkoxy) group, a cyano group or a nitro group), $R^2$ represents a substituted or unsubstituted, $C_1$–$C_8$ aliphatic acyl group (the substituent of said group being a halogen atom, a hydroxyl group, a $C_1$–$C_4$ alkoxy group or a cyano group), a substituted or unsubstituted benzoyl group (the substituent of said group being a $C_1$–$C_4$ alkyl group, a halogen atom or a $C_1$–$C_4$ alkoxy group) or a ($C_1$–$C_4$ alkoxy)carbonyl group, and $R^3$ represents a substituted, 3 to 7 membered, saturated cyclic amino group which may form a fused ring [the non-optional substituent of said group being a protected or unprotected mercapto group or a $C_1$–$C_4$ alkyl group substituted with a protected or unprotected mercapto group, said cyclic amino group being preferably further substituted with a group of the formula $=CR^4R^5$ (in which $R^4$ and $R^5$ are the same or different and each independently represents a hydrogen atom, a $C_1$–$C_4$ alkyl group, a carboxy group, a ($C_1$–$C_4$ alkoxy)carbonyl group, a carbamoyl group or a mono- or di-($C_1$–$C_4$ alkyl)carbamoyl group); and the protecting group of said mercapto group being a $C_1$–$C_{20}$ alkanoyl group, a $C_3$–$C_{20}$ alkenoyl group, a substituted or unsubstituted benzoyl group (the substituent of said group being a $C_1$–$C_4$ alkyl group, a halogen atom or a $C_1$–$C_4$ alkoxy group) or a ($C_1$–$C_4$ alkoxy)carbonyl group].

The $C_1$–$C_4$ alkyl group in the definition of substituents for the substituted or unsubstituted phenyl group of $R^1$ is a straight or branched $C_1$–$C_4$ alkyl group, and may be for example, a methyl, ethyl, propyl, isopropyl, butyl, sec-butyl, t-butyl or isobutyl group, of which a methyl or ethyl group is preferred and a methyl group is particularly preferred.

The halogen atom in the definition of substituents for the substituted or unsubstituted phenyl group of $R^1$ may be, for example, a fluorine, chlorine, bromine or iodine atom, of which a fluorine, chlorine or bromine atom is preferred and a fluorine or chlorine atom is particularly preferred.

The fluoro-substituted-($C_1$–$C_4$ alkyl) group in the definition of the substituents for the substituted or unsubstituted phenyl group of $R^1$ is a straight or branched fluoro-substituted $C_1$–$C_4$ alkyl group, and may be, for example, a fluoromethyl, difluoromethyl, trifluoromethyl, 2-fluoroethyl, 2-fluoropropyl, 3-fluoropropyl, 2-fluorobutyl, 3-fluorobutyl or 4-fluorobutyl group, of which a difluoromethyl or trifluoromethyl group is preferred and a trifluoromethyl group is particularly preferred.

The $C_1$–$C_4$ alkoxy group in the definition of the substituents for the substituted or unsubstituted phenyl group of $R^1$ is a straight or branched $C_1$–$C_4$ alkoxy group, and may be, for example, a methoxy, ethoxy, propoxy, isopropoxy, butoxy, sec-butoxy, t-butoxy or isobutoxy group, of which a methoxy or ethoxy group is preferred and a methoxy group is particularly preferred.

The fluoro-substituted-($C_1$–$C_4$ alkoxy) group in the definition of the substituents for the substituted or unsubstituted phenyl group of $R^1$ is a straight or branched fluoro-substituted-($C_1$–$C_4$ alkoxy) group, and may be, for example, fluoromethoxy, difluoromethoxy, trifluoromethoxy, 2-fluoroethoxy, 2-fluoropropoxy, 3-fluoropropoxy, 2-fluoroisopropoxy or 4-fluorobutoxy group, of which a difluoromethoxy or trifluoromethoxy group is preferred and a trifluoromethoxy group is particularly preferred.

As the substituent for the substituted or unsubstituted phenyl group of $R^1$, a methyl group, ethyl group, halogen atom, fluoro-substituted methyl group, methoxy group, ethoxy group, fluoro-substituted methoxy group, cyano group or nitro group is preferred, of which a fluorine atom, chlorine atom, bromine atom, trifluoromethyl group, difluoromethoxy group, trifluoromethoxy group, cyano group or nitro group is more preferred and a fluorine or chlorine atom is particularly preferred.

The number of said substituents preferably ranges from 1 to 3, of which 1 or 2 is more preferred. The substituent position is preferably at the 2- or 4-position, of which the 2-position is particularly preferred.

The aliphatic acyl group of the substituted or unsubstituted $C_1$–$C_8$ aliphatic acyl group of $R^2$ is a straight or branched $C_1$–$C_8$ alkanoyl group, and may be, for example, a formyl, acetyl, propionyl, butyryl, isobutyryl, valeryl, isovaleryl, pivaloyl, hexanoyl, heptanoyl or octanoyl group; or a ($C_3$–$C_7$ cycloalkyl)carbonyl group such as a cyclopropylcarbonyl, cyclobutylcarbonyl, cyclopentylcarbonyl, cyclohexylcarbonyl or cycloheptylcarbonyl group, of which a $C_2$–$C_4$ alkanoyl or ($C_3$–$C_6$ cycloalkyl)carbonyl group is preferred and an acetyl, propionyl, isobutyryl, cyclopropylcarbonyl or cyclobutylcarbonyl group is more preferred.

The halogen atom and the $C_1$–$C_4$ alkoxy group each of which is a substituent for the aliphatic acyl group have the same meanings as defined for the substituents of said phenyl group, while the substituent for the aliphatic acyl group is preferably a fluorine atom, chlorine atom, hydroxyl group, methoxy group, ethoxy group or cyano group, of which a fluorine or chlorine atom is more preferred and a fluorine atom is particularly preferred.

Specific examples of the substituted aliphatic acyl group may be, for example, fluoroacetyl, difluoroacetyl, trifluoroacetyl, chloroacetyl, trichloroacetyl, bromoacetyl, iodoacetyl, 3-fluoropropionyl, 3-chloropropionyl, 3-bromopropionyl, 3-iodopropionyl, 4-fluorobutyryl, 4-chlorobutyryl, 5-fluorovaleryl, hydroxyacetyl, 3-hydroxypropionyl, 4-hydroxybutyryl, 5-hydroxyvaleryl, methoxyacetyl, 3-methoxypropionyl, 4-methoxybutyryl, 5-methoxyvaleryl, ethoxyacetyl, 3-ethoxypropionyl, 4-ethoxybutyryl, 5-ethoxyvaleryl, cyanoacetyl, 3-cyanopropionyl, 4-cyanobutyryl, 5-cyanovaleryl, 2-fluorocyclopropylcarbonyl, 2,2-difluorocyclopropylcarbonyl, 2-chlorocyclopropylcarbonyl, 2-bromocyclopropylcarbonyl, 2-fluorocyclobutylcarbonyl, 2-chlorocyclobutylcarbonyl, 2-fluorocyclopentylcarbonyl, 2-chlorocyclopentylcarbonyl, 2-fluorocyclohexylcarbonyl, 2-chlorocyclohexylcarbonyl, 2-hydroxycyclopropylcarbonyl, 2-hydroxycyclobutylcarbonyl, 2-hydroxycyclopentylcarbonyl, 2-hydroxycyclohexylcarbonyl, 2-methoxycyclopropycarbonyl, 2-methoxycyclobutylcarbonyl, 2-methoxycyclopentylcarbonyl, 2-methoxycyclohexylcarbonyl, 2-ethoxycyclopropylcarbonyl, 2-ethoxycyclobutylcarbonyl, 2-ethoxycyclopentylcarbonyl, 2-ethoxycyclohexylcarbonyl, 2-cyanocyclopropylcarbonyl, 2-cyanocyclobutylcarbonyl, 2-cyanocyclopentylcarbonyl and 2-cyanocyclohexylcarbonyl groups, of which fluoroacetyl, difluoroacetyl, trifluoroacetyl, chloroacetyl, 3-fluoropropionyl, 3-chloropropionyl, hydroxyacetyl, 3-hydroxypropionyl, methoxyacetyl, 3-methoxypropionyl, ethoxyacetyl, cyanoacetyl, 3-cyanopropionyl, 2-fluorocyclopropylcarbonyl, 2,2-difluorocyclopropylcarbonyl,
2-chlorocyclopropylcarbonyl, 2-fluorocyclobutylcarbonyl, 2-chlorocyclobutylcarbonyl, 2-fluorocyclopentylcarbonyl, 2-fluorocyclohexylcarbonyl, 2-hydroxycyclopropylcarbonyl, 2-methoxycyclopropylcarbonyl, 2-ethoxycyclopropylcarbonyl and 2-cyanocyclopropylcarbonyl groups are preferred, fluoroacetyl, difluoroacetyl, trifluoroacetyl, chloroacetyl, 3-fluoropropionyl, 2-fluorocyclopropylcarbonyl, 2-chlorocyclopropylcarbonyl and 2-fluorocyclobutylcarbonyl groups are more preferred, and fluoroacetyl, difluoroacetyl, trifluoroacetyl, 3-fluoropropionyl and 2-fluorocyclopropylcarbonyl groups are particularly preferred.

The $C_1$–$C_4$ alkyl group, halogen atom and $C_1$–$C_4$ alkoxy group in the definition of the substituent for the substituted or unsubstituted benzoyl group of $R^2$ have the same meanings as defined for the substituents of said phenyl group. As the substituent for the benzoyl group, a methyl group, ethyl group, fluorine atom, chlorine atom, methoxy group or ethoxy group is preferred, of which a fluorine or chlorine atom is more preferred and a fluorine atom is particularly preferred.

The $C_1$–$C_4$ alkoxy part of the ($C_1$–$C_4$ alkoxy)carbonyl group of $R^2$ has the same meaning as defined for the substituents of said phenyl group. A methoxycarbonyl or ethoxycarbonyl group is preferred, of which a methoxycarbonyl group is particularly preferred.

Examples of the amino part of the substituted 3 to 7 membered saturated cyclic amino group which may form a fused ring are $C_2$–$C_8$ cyclic amino groups which may have an oxygen, nitrogen or sulfur atom, and may be, for example, 1-aziridinyl, 1-azetidinyl, 1-pyrrolidinyl, 1-piperidinyl, 2H-hexahydroazepin-1-yl, 7-azabicyclo[3.1.1]heptan-7-yl, 8-azabicyclo[3.2.1]octan-8-yl, 9-azabicyclo[3.3.1]nonan-9-yl, 4-morpholinyl, 4-thiomorpholinyl or 4-piperazinyl groups, of which a 1-azetidinyl, 1-pyrrolidinyl, 1-piperidinyl, 7-azabicyclo[3.1.1]heptan-7-yl, 8-azabicyclo[3.2.1]octan-8-yl, 9-azabicyclo[3.3.1]nonan-9-yl, 4-morpholinyl or 4-thiomorpholinyl group is preferred, a 1-azetidinyl, 1-pyrrolidinyl, 1-piperidinyl, 8-azabicyclo[3.2.1]octan-8-yl or 9-azabicyclo[3.3.1]nonan-9-yl group is more preferred, a 1-azetidinyl, 1-pyrrolidinyl, 1-piperidinyl or 8-azabicyclo[3.2.1]octan-8-yl group is still more preferred, and a 1-azetidinyl, 1-piperidinyl or 8-azabicyclo[3.2.1]octan-8-yl group is particularly preferred.

The $C_1$–$C_4$ alkyl part of the mercapto-substituted $C_1$–$C_4$ alkyl group which is a substituent of the 3 to 7 membered cyclic amino group represented by $R^3$, and the $C_1$–$C_4$ alkyl part of the $C_1$–$C_4$ alkyl group or the mono- or di-($C_1$–$C_4$ alkyl)carbamoyl group represented by $R^4$ or $R^5$ have the same meanings as defined for the substituents of said phenyl group, while the ($C_1$–$C_4$ alkoxy)carbonyl group represented by $R^4$ or $R^5$ has the same meaning as defined in the above-described $R^2$.

The $C_1$–$C_{20}$ alkanoyl group which is a protecting group for the mercapto group is a straight or branched $C_1$–$C_{20}$ alkanoyl group, and may be, for example, a $C_1$–$C_8$ alkanoyl group as exemplified above in $R^2$, or a nonanoyl, decanoyl, lauroyl, myristoyl, palmitoyl, stearoyl or icosanoyl group, of which a $C_1$–$C_{12}$ alkanoyl group is preferred and a $C_1$–$C_6$ alkanoyl group is more preferred and a $C_2$–$C_5$ alkanoyl group is particularly preferred.

Examples of the $C_3$–$C_{20}$ alkenoyl group which is a protecting group for the mercapto group are straight or branched $C_3$–$C_{20}$ alkenoyl groups, and may be, for example, acroyl, methacroyl, 2-butenoyl, 3-butenoyl, 2-pentenoyl, 3-pentenoyl, 2-hexenoyl, 3-hexenoyl, 2-octenoyl, 3-octenoyl, 5-dodecenoyl (particularly, cis-form), palmitoleoyl, oleoyl or 11-icosenoyl (particularly, cis-form), of which $C_8$–$C_{20}$ alkenoyl groups are preferred, $C_{12}$–$C_{20}$ alkenoyl groups are more preferred, $C_{15}$–$C_{20}$ alkenoyl groups are still more preferred and a palmitoleoyl or oleoyl group is particularly preferred.

The substituted or unsubstituted benzoyl group and ($C_1$–$C_4$ alkoxy)carbonyl group each being a protecting group for the mercapto group have the same meanings as defined above in $R^2$.

As the substituted 3 to 7 membered saturated cyclic amino group which may form a fused ring, preferred are a 3-(protected or unprotected mercapto, or protected or unprotected mercapto $C_1$–$C_4$ alkyl)-1-azetidinyl group, a 3-(protected or unprotected mercapto, or protected or unprotected mercapto $C_1$–$C_4$ alkyl)-1-pyrrolidinyl group, a 3- or 4-(protected or unprotected mercapto, or protected or unprotected mercapto $C_1$–$C_4$ alkyl)-1-piperidinyl group, a 4-(protected or unprotected mercapto, or protected or unprotected mercapto $C_1$–$C_4$ alkyl)-3-(=$CR^4R^5$)-1-piperidinyl group [in which $R^4$ and $R^5$ are the same or different and each independently represents a hydrogen atom, a $C_1$–$C_4$ alkyl group, a carboxy group, a ($C_1$–$C_4$ alkoxy)carbonyl group, a carbamoyl group, or a mono- or di-($C_1$–$C_4$ alkyl)carbamoyl group] or a 8-aza-3-(protected or unprotected mercapto, or protected or unprotected mercapto $C_1$–$C_4$ alkyl)-bicyclo[3.2.1]octan-8-yl group, more preferred are 3-(protected or unprotected mercapto, or protected or unprotected mercaptomethyl)-1-azetidinyl groups, 3-(protected or unprotected mercapto, or protected or unprotected mercaptomethyl)-1-pyrrolidinyl groups, 3- or 4-(protected or unprotected mercapto, or protected or unprotected mercaptomethyl)- 1-piperidinyl groups, 4-(protected or unprotected mercapto)-3-(=$CR^4R^5$)-1-piperidinyl groups (in which $R^4$ and $R^5$ are the same or different and each independently represents a hydrogen atom, a methyl group, an ethyl group, a carboxy group, a methoxycarbonyl group, an ethoxycarbonyl group, a carbamoyl group, a methylcarbamoyl group, an ethylcarbamoyl group, a dimethylcarbamoyl group or a diethylcarbamoyl group) or 8-aza-3-(protected or unprotected mercapto, or protected or unprotected mercaptomethyl)-bicyclo[3.2.1]octan-8-yl groups, still more preferred are 3-(protected or unprotected mercapto)-1-azetidinyl groups, 3-(protected or unprotected mercapto)-1-pyrrolidinyl groups, 3- or 4-(protected or unprotected mercapto)-1-piperidinyl groups, 4-(protected or unprotected mercapto)-3-(=$CR^4R^5$)-1-piperidinyl groups (in which $R^4$ represents a hydrogen atom and $R^5$ represents a hydrogen atom, a methyl group, a carboxy group, a methoxycarbonyl group, an ethoxycarbonyl group, a carbamoyl group, a methylcarbamoyl group or a dimethylcarbamoyl group) or 8-aza-3-(protected or unprotected mercapto)bicyclo[3.2.1]octan-8-yl groups, and particularly preferred are 3-(protected or unprotected mercapto)-1-azetidinyl groups, 4-(protected or unprotected mercapto)-1-piperidinyl groups, 4-(protected or unprotected mercapto)-3-(=$CR^4R^5$)-1-piperidinyl groups (in which $R^4$ represents a hydrogen atom and $R^5$ represents a carboxy group, a methoxycarbonyl group, an ethoxycarbonyl group, a carbamoyl group, a methylcarbamoyl group or a dimethylcarbamoyl group) or 8-aza-3-(protected or unprotected mercapto)bicyclo[3.2.1]octan-8-yl groups.

In the compound represented by the formula (I), a carbon atom to which $R^1$ is bonded may be an asymmetric carbon atom and if so, there exist optical isomers based thereon. These isomers and mixtures thereof are also embraced in the compound of the present invention. When in the compound represented by the formula (I), a double bond is contained in the molecule thereof and/or two substituents are included in the cycloalkyl group or cyclic amino group, there exist cis/trans geometrical isomers based on them. These isomers and mixtures thereof are also embraced in the compound of the present invention.

The compound (I) of the present invention can be converted easily into a pharmaceutically acceptable salt thereof by treatment with a base when $R^4$ or $R^5$ represents a carboxy group. Examples of such a salt may be inorganic salts, for example, alkali metal salts such as a sodium salt, potassium salt or lithium salt, alkaline earth metal salts such as a calcium salt or magnesium salt, metal salts such as an aluminum salt, iron salt, zinc salt, copper salt, nickel salt or cobalt salt, or an ammonium salt; or amine salts, for example, organic salts such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt or tris(hydroxymethyl)aminomethane salt, of which the alkali metal salts (particularly sodium salt or potassium salt) are preferred.

Alternatively, the compound (I) can be converted easily into a pharmaceutically acceptable salt thereof by the treatment with an acid. Examples of such a salt may be, for example, inorganic acid salts such as hydrochloride, sulfate, nitrate or phosphate, or organic acid salts such as acetate, propionate, butyrate, benzoate, oxalate, malonate, succinate, maleate, fumarate, tartrate, citrate, methanesulfonate, ethanesulfonate, benzenesulfonate or p-toluenesulfonate, of which the hydrochloride, sulfate, nitrate, oxalate, succinate, fumarate or methanesulfonate is preferred.

In addition, the hydrates of the compound (I) or its salt are also embraced in the present invention.

As the compound represented by the formula (I) which is an effective ingredient of the present invention, the following compounds are preferred:

(1) compounds wherein $R^1$ represents a substituted phenyl group (the substituent of said group being methyl, ethyl, halogen, fluoro-substituted-methyl, methoxy, ethoxy, fluoro-substituted-methoxy, cyano or nitro), (2) compounds wherein $R^1$ represents a substituted phenyl group (the substituent of said group being fluorine, chlorine, bromine, trifluoromethyl, difluoromethoxy, trifluoromethoxy, cyano or nitro), (3) compounds wherein $R^1$ represents a substituted phenyl group (the substituent of said group being fluorine or chlorine), (4) compounds wherein the number of substituents on the substituted phenyl group represented by $R^1$ ranges from 1 to 3, (5) compounds wherein the number of substituents on the substituted phenyl group represented by $R^1$ is 1 or 2, (6) compounds wherein the position of the substituent on the substituted phenyl group represented by $R^1$ is 2 or 4, (7) compounds wherein $R^2$ represents a substituted or unsubstituted $C_2$–$C_4$ alkanoyl or ($C_3$–$C_6$ cycloalkyl) carbonyl group (the substituent of said group being fluorine, chlorine, hydroxyl, methoxy, ethoxy or cyano), a substituted or unsubstituted benzoyl group (the substituent of said group being methyl, ethyl, fluorine, chlorine, methoxy or ethoxy) or a ($C_1$–$C_4$ alkoxy)carbonyl group, (8) compounds wherein $R^2$ represents a $C_2$–$C_4$ alkanoyl or ($C_3$–$C_6$ cycloalkyl)carbonyl group which is unsubstituted or substituted by fluorine or chlorine, a benzoyl group or a ($C_1$–$C_4$ alkoxy)carbonyl group, (9) compounds wherein $R^2$ represents an acetyl, propionyl, isobutyryl, cyclopropylcarbonyl or cyclobutylcarbonyl group, said groups being unsubstituted or being substituted by fluorine, or a methoxycarbonyl or ethoxycarbonyl group,

(10) compounds wherein $R^2$ represents a propionyl, cyclopropylcarbonyl, methoxycarbonyl or ethoxycarbonyl group,

(11) compounds wherein $R^3$ represents a 3-(protected or unprotected mercapto, or protected or unprotected mercapto $C_1$–$C_4$ alkyl)-1-azetidinyl group, 3-(protected or unprotected mercapto, or protected or unprotected mercapto $C_1$–$C_4$ alkyl)-1-pyrrolidinyl group, 3- or 4-(protected or unprotected mercapto, or protected or unprotected mercapto $C_1$–$C_4$ alkyl)-1-piperidinyl group, 4-(protected or unprotected mercapto, or protected or unprotected mercapto $C_1$–$C_4$ alkyl)-3-(=$CR^4R^5$)-1-piperidinyl group or 8-aza-3-(protected or unprotected mercapto, or protected or unprotected mercapto $C_1$–$C_4$ alkyl)bicyclo[3.2.1]octan-8-yl group, $R^4$ and $R^5$ are the same or different and each independently represents a hydrogen atom, $C_1$–$C_4$ alkyl group, carboxy group, ($C_1$–$C_4$ alkoxy)carbonyl group, carbamoyl group, or mono- or di-($C_1$–$C_4$ alkyl)carbamoyl group, and the protecting group for the mercapto group is a $C_1$–$C_{20}$ alkanoyl, $C_3$–$C_{20}$ alkenoyl, substituted or unsubstituted benzoyl (the substituent of said group being a $C_1$–$C_4$ alkyl group, a halogen atom or a $C_1$–$C_4$ alkoxy group) or ($C_1$–$C_4$ alkoxy)carbonyl group,

(12) compounds wherein $R^3$ represents a 3-(protected or unprotected mercapto, or protected or unprotected mercaptomethyl)-1-azetidinyl group, 3-(protected or unprotected mercapto, or protected or unprotected mercaptomethyl)-1-pyrrolidinyl group, 3- or 4-(protected or unprotected mercapto, or protected or unprotected mercaptomethyl)-1-piperidinyl group, 4-(protected or unprotected mercapto)-3-(=$CR^4R^5$)-1-piperidinyl group or 8-aza-3-(protected or unprotected mercapto, or protected or unprotected mercaptomethyl)bicyclo[3.2.1]octan-8-yl group, $R^4$ and $R^5$ are the same or different and each independently represents a hydrogen atom or a methyl, ethyl, carboxy, methoxycarbonyl, ethoxycarbonyl, carbamoyl, methylcarbamoyl, ethylcarbamoyl, dimethylcarbamoyl or diethylcarbamoyl group, and the protecting group for the mercapto group is a $C_1$–$C_{20}$ alkanoyl, $C_8$–$C_{20}$ alkenoyl, substituted or unsubstituted benzoyl (the substituent of said group being methyl, ethyl, fluorine, chlorine, methoxy or ethoxy) or ($C_1$–$C_4$ alkoxy)carbonyl group,

(13) compounds wherein $R^3$ represents a 3-(protected or unprotected mercapto)-1-azetidinyl group, 3-(protected or unprotected mercapto)-1-pyrrolidinyl group, 3- or 4-(protected or unprotected mercapto)-1-piperidinyl group, 4-(protected or unprotected mercapto)-3-(=$CR^4R^5$)-1-piperidinyl group or 8-aza-3-(protected or unprotected mercapto)bicyclo[3.2.1]octan-8-yl group, $R^4$ represents a hydrogen atom, $R^5$ represents a hydrogen atom or a methyl, carboxy, methoxycarbonyl, ethoxycarbonyl, carbamoyl, methylcarbamoyl, or dimethylcarbamoyl group, and the protecting group for the mercapto group is a $C_2$–$C_6$ alkanoyl, palmitoleoyl, oleoyl, benzoyl, methoxycarbonyl or ethoxycarbonyl group, and

(14) compounds wherein $R^3$ represents a 3-(protected or unprotected mercapto)-1-azetidinyl group, 4-(protected or unprotected mercapto)-1-piperidinyl group, 4-(protected or unprotected mercapto)-3-(=$CR^4R^5$)-1-piperidinyl group or 8-aza-3-(protected or unprotected mercapto)bicyclo[3.2.1]octan-8-yl group, $R^4$ represents a hydrogen atom, $R^5$ represents a carboxy, methoxycarbonyl, ethoxycarbonyl, carbamoyl, methylcarbamoyl or dimethylcarbamoyl group, and the protecting group for the mercapto group is a $C_2$–$C_5$ alkanoyl, benzoyl, methoxycarbonyl or ethoxycarbonyl group.

$R^1$ is preferred in the order of (1) to (3) and (4) to (6), $R^2$ is preferred in the order of (7) to (10) and $R^3$ is preferred in the order of (11) to (14).

As the compound represented by the formula (I), any combination of 2 to 4 groups selected from the class consisting of a group of (1) to (3), a group of (4) to (6), a group of (7) to (10) and a group of (11) to (14) can be employed. Preferred examples in such a combination include:

(15) compounds wherein $R^1$ represents a substituted phenyl group (the substituent of said group being methyl, ethyl, halogen, fluoro-substituted-methyl, methoxy, ethoxy, fluoro-substituted-methoxy, cyano or nitro), the number of substituents on the substituted phenyl group represented by $R^1$ ranges from 1 to 3, $R^2$ represents a substituted or unsubstituted $C_2$–$C_4$ alkanoyl or ($C_3$–$C_6$ cycloalkyl)carbonyl group (the substituent of said group being fluorine, chlorine, hydroxyl, methoxy, ethoxy or cyano), a substituted or unsubstituted benzoyl group (the substituent of said group being methyl, ethyl, fluorine, chlorine, methoxy or ethoxy) or a ($C_1$–$C_4$ alkoxy)carbonyl group,

(16) compounds wherein $R^1$ represents a substituted phenyl group (the substituent of said group being fluorine, chlorine, bromine, trifluoromethyl, difluoromethoxy, trifluoromethoxy, cyano or nitro), the number of substituents on the substituted phenyl group represented by $R^1$ is 1 or 2, and $R^2$ represents a $C_2$–$C_4$ alkanoyl or ($C_3$–$C_6$ cycloalkyl) carbonyl group which is unsubstituted or is substituted by fluorine or chlorine, a benzoyl group or a ($C_1$–$C_4$ alkoxy)carbonyl group,

(17) compounds wherein $R^1$ represents a substituted phenyl group (the substituent of said group being fluorine, chlorine, bromine, trifluoromethyl, difluoromethoxy, trifluoromethoxy, cyano or nitro), the position of the substituent on the substituted phenyl group represented by $R^1$ is 2 or 4, $R^2$ represents a $C_2$–$C_4$ alkanoyl or ($C_3$–$C_6$ cycloalkyl) carbonyl group which is unsubstituted or is substituted by fluorine or chlorine, a benzoyl group or a ($C_1$–$C_4$ alkoxy)carbonyl group, $R^3$ represents a 3-(protected or unprotected mercapto, or protected or unprotected mercapto $C_1$–$C_4$ alkyl)-1-azetidinyl group, 3-(protected or unprotected mercapto, or protected or unprotected mercapto $C_1$–$C_4$ alkyl)-1-pyrrolidinyl group, 3-or 4-(protected or unprotected mercapto, or protected or unprotected mercapto $C_1$–$C_4$ alkyl)-1-piperidinyl group, 4-(protected or unprotected mercapto, or protected or unprotected mercapto $C_1$–$C_4$ alkyl)-3-(=$CR^4R^5$)-1-piperidinyl group or 8-aza-3-(protected or unprotected mercapto, or protected or unprotected mercapto $C_1$–$C_4$ alkyl)bicyclo[3.2.1] octan-8-yl group, $R^4$ and $R^5$ are the same or different and each independently represents a hydrogen atom, $C_1$–$C_4$ alkyl group, carboxy group, ($C_1$–$C_4$ alkoxy)carbonyl group, carbamoyl group, or mono- or di-($C_1$–$C_4$ alkyl)carbamoyl group, and the protecting group for the mercapto group is a $C_1$–$C_{20}$ alkanoyl, $C_3$–$C_{20}$ alkenoyl, substituted or unsubstituted benzoyl (the substituent of said group being a $C_1$–$C_4$ alkyl group, a halogen atom or a $C_1$–$C_4$ alkoxy group) or ($C_1$–$C_4$ alkoxy)carbonyl group,

(18) compounds wherein $R^1$ represents a substituted phenyl group (the substituent of said group being fluorine or chlorine), the position of the substituent on the substituted phenyl group represented by $R^1$ is 2 or 4, $R^2$ represents an acetyl, propionyl, isobutyryl, cyclopropylcarbonyl or cyclobutylcarbonyl group, said groups being unsubstituted or being substituted by fluorine, or a methoxycarbonyl or ethoxycarbonyl group, $R^3$ represents a 3-(protected or unprotected mercapto, or protected or unprotected mercaptomethyl)-1-azetidinyl group, 3-(protected or unprotected mercapto, or protected or unprotected mercaptomethyl)-1-pyrrolidinyl group, 3- or 4-(protected or unprotected mercapto, or protected or unprotected mercaptomethyl)-1-piperidinyl group, 4-(protected or unprotected mercapto)-3-(=$CR^4R^5$)-1-piperidinyl group or 8-aza-3-(protected or unprotected mercapto, or protected or unprotected mercaptomethyl)bicyclo[3.2.1]octan-8-yl group, $R^4$ and $R^5$ are the same or different and each independently represents a hydrogen atom, or a methyl, ethyl, carboxy, methoxycarbonyl, ethoxycarbonyl, carbamoyl, methylcarbamoyl, ethylcarbamoyl, dimethylcarbamoyl or diethylcarbamoyl group, and the protecting group for the mercapto group is a $C_1$–$C_{20}$ alkanoyl, $C_8$–$C_{20}$ alkenoyl, substituted or unsubstituted benzoyl (the substituent of said group being methyl, ethyl, fluorine, chlorine, methoxy or ethoxy) or ($C_1$–$C_4$ alkoxy)carbonyl group,

(19) compounds wherein $R^1$ represents a substituted phenyl group (the substituent of said group being a fluorine or chlorine atom), the position of the substituent on the substituted phenyl group represented by $R^1$ is 2 or 4, $R^2$ represents a propionyl, cyclopropylcarbonyl, methoxycarbonyl or ethoxycarbonyl group, $R^3$ represents a 3-(protected or unprotected mercapto)-1-azetidinyl group, 3-(protected or unprotected mercapto)-1-pyrrolidinyl group, 3- or 4-(protected or unprotected mercapto)-1-piperidinyl group, 4-(protected or unprotected mercapto)-3-(=$CR^4R^5$)-1-piperidinyl group or 8-aza-3-(protected or unprotected mercapto)bicyclo[3.2.1]octan-8-yl group, $R^4$ represents a hydrogen atom, $R^5$ represents a hydrogen atom, or a methyl, carboxy, methoxycarbonyl, ethoxycarbonyl, carbamoyl, methylcarbamoyl or dimethylcarbamoyl group, and the protecting group for the mercapto group is a $C_2$–$C_6$ alkanoyl, palmitoleoyl, oleoyl, benzoyl, methoxycarbonyl or ethoxycarbonyl group, and

(20) compounds wherein $R^1$ represents a substituted phenyl group (the substituent of said group being a fluorine or chlorine atom), the position of the substituent on the substituted phenyl group represented by $R^1$ is 2 or 4, $R^2$ represents a propionyl, cyclopropylcarbonyl, methoxycarbonyl or ethoxycarbonyl group, $R^3$ represents a 3-(protected or unprotected mercapto)-1-azetidinyl group, 4-(protected or unprotected mercapto)-1-piperidinyl group, 4-(protected or unprotected mercapto)-3-(=$CR^4R^5$)-1-piperidinyl group or 8-aza-3-(protected or unprotected mercapto)bicyclo [3.2.1]octan-8-yl group, $R^4$ represents a hydrogen atom, $R^5$ represents a carboxy, methoxycarbonyl, ethoxycarbonyl, carbamoyl, methylcarbamoyl or dimethylcarbamoyl group, and the protecting group of the mercapto group is a $C_2$–$C_5$ alkanoyl, benzoyl, methoxycarbonyl or ethoxycarbonyl group.

The above-described compounds are preferred in the order of (15) to (20).

As the compound of the formula (I), the following compounds in Table 1 can be given as specific preferred examples.

TABLE 1

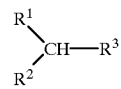

(I)

| Comp. No. | $R^1$ | $R^2$ | $R^3$ |
|---|---|---|---|
| 1 | Ph | CHO | 3-SH-Pyrd |
| 2 | 2-F—Ph | Ac | 3-SH-Pyrd |
| 3 | 3-F—Ph | PhCO | 3-SH-Pyrd |

TABLE 1-continued $$\underset{R^2}{\overset{R^1}{\diagdown}}CH-R^3 \qquad (I)$$

| Comp. No. | R¹ | R² | R³ |
|---|---|---|---|
| 4 | 4-F—Ph | 4-F-PhCO | 3-SH-Pyrd |
| 5 | 2-Cl—Ph | c-PrCO | 3-SH-Pyrd |
| 6 | 3-Cl—Ph | 2,4-diF—PhCO | 3-SH-Pyrd |
| 7 | 4-Cl—Ph | i-Bur | 3-SH-Pyrd |
| 8 | 2-Br—Ph | FCH₂CO | 3-SH-Pyrd |
| 9 | 4-I—Ph | 3-Cl-Prop | 3-SH-Pyrd |
| 10 | 2-NO₂—Ph | c-PrCO | 3-SH-Pyrd |
| 11 | 2-F—Ph | 2,2-diF-c-PrCO | 3-SH-Pyrd |
| 12 | 2-CN—Ph | c-PrCO | 3-SH-Pyrd |
| 13 | 4-CN—Ph | Prop | 3-SH-Pyrd |
| 14 | 2-F-4-Me—Ph | NCCH₂CO | 3-SH-Pyrd |
| 15 | 2-CF₃—Ph | c-PrCO | 3-SH-Pyrd |
| 16 | 2-F-4-OMe—Ph | MeOCH₂CO | 3-SH-Pyrd |
| 17 | 2-F—Ph | 2-F-c-PrCO | 3-SH-Pyrd |
| 18 | Pent-F—Ph | Ac | 3-SH-Pyrd |
| 19 | 2,6-di-F—Ph | 3-F-Prop | 3-SH-Pyrd |
| 20 | 2-F—Ph | c-PrCO | 3-SH-Pyrd |
| 21 | 2,4-di-F—Ph | c-BuCO | 3-SH-Pyrd |
| 22 | 2-F-6-Cl—Ph | Bur | 3-SH-Pyrd |
| 23 | 2-F-6-CN—Ph | HOCH₂CO | 3-SH-Pyrd |
| 24 | 2-F-6-NO₂Ph | CF₃CO | 3-SH-Pyrd |
| 25 | Ph | BuOCO | 3-SH-Pyrd |
| 26 | 2-F—Ph | MeOCO | 3-SH-Pyrd |
| 27 | 3-F—Ph | EtOCO | 3-SH-Pyrd |
| 28 | 4-F—Ph | PrOCO | 3-SH-Pyrd |
| 29 | 2-Cl—Ph | MeOCO | 3-SH-Pyrd |
| 30 | 3-Cl—Ph | i-PrOCO | 3-SH-Pyrd |
| 31 | 4-Cl—Ph | i-BuOCO | 3-SH-Pyrd |
| 32 | Ph | CHO | 3-(CH₂SH)-Pyrd |
| 33 | 2-F—Ph | Ac | 3-(CH₂SH)-Pyrd |
| 34 | 3-F—Ph | PhCO | 3-(CH₂SH)-Pyrd |
| 35 | 4-F—Ph | 4-F-PhCO | 3-(CH₂SH)-Pyrd |
| 36 | 2-Cl—Ph | c-PrCO | 3-(CH₂SH)-Pyrd |
| 37 | 3-Cl—Ph | 2,4-diF-PhCO | 3-(CH₂SH)-Pyrd |
| 38 | 4-Cl—Ph | i-Bur | 3-(CH₂SH)-Pyrd |
| 39 | 2-Br—Ph | FCH₂CO | 3-(CH₂SH)-Pyrd |
| 40 | 4-I—Ph | 3-Cl-Prop | 3-(CH₂SH)-Pyrd |
| 41 | 2-NO₂—Ph | c-PrCO | 3-(CH₂SH)-Pyrd |
| 42 | 2-F—Ph | 2,2-diF-c-PrCO | 3-(CH₂SH)-Pyrd |
| 43 | 2-CN—Ph | c-PrCO | 3-(CH₂SH)-Pyrd |
| 44 | 4-CN—Ph | Prop | 3-(CH₂SH)-Pyrd |
| 45 | 2-F-4-Me—Ph | NCCH₂CO | 3-(CH₂SH)-Pyrd |
| 46 | 2-CF₃—Ph | c-PrCO | 3-(CH₂SH)-Pyrd |
| 47 | 2-F-4-OMe—Ph | MeOCH₂CO | 3-(CH₂SH)-Pyrd |
| 48 | 2-F—Ph | 2-F-c-PrCO | 3-(CH₂SH)-Pyrd |
| 49 | Pent-F—Ph | Ac | 3-(CH₂SH)-Pyrd |
| 50 | 2,6-di-F—Ph | 3-F-Prop | 3-(CH₂SH)-Pyrd |
| 51 | 2-F—Ph | c-PrCO | 3-(CH₂SH)-Pyrd |
| 52 | 2,4-di-F—Ph | c-BuCO | 3-(CH₂SH)-Pyrd |
| 53 | 2-F-6-Cl—Ph | Bur | 3-(CH₂SH)-Pyrd |
| 54 | 2-F-6-CN—Ph | HOCH₂CO | 3-(CH₂SH)-Pyrd |
| 55 | 2-F-6-NO₂—Ph | CF₃CO | 3-(CH₂SH)-Pyrd |
| 56 | Ph | BuOCO | 3-(CH₂SH)-Pyrd |
| 57 | 2-F—Ph | MeOCO | 3-(CH₂SH)-Pyrd |
| 58 | 3-F—Ph | EtOCO | 3-(CH₂SH)-Pyrd |
| 59 | 4-F—Ph | PrOCO | 3-(CH₂SH)-Pyrd |
| 60 | 2-Cl—Ph | MeOCO | 3-(CH₂SH)-Pyrd |
| 61 | 3-Cl—Ph | i-PrOCO | 3-(CH₂SH)-Pyrd |
| 62 | 4-Cl-Ph | i-BuOCO | 3-(CH₂SH)-Pyrd |
| 63 | Ph | CHO | 4-SH-Pipd |
| 64 | 2-F—Ph | Ac | 4-SH-Pipd |
| 65 | 3-F—Ph | PhCO | 4-SH-Pipd |
| 66 | 4-F—Ph | 4-F-PhCO | 4-SH-Pipd |
| 67 | 2-Cl—Ph | c-PrCO | 4-SH-Pipd |
| 68 | 3-Cl—Ph | 2,2-diF-c-PhCO | 4-SH-Pipd |
| 69 | 4-Cl—Ph | i-Bur | 4-SH-Pipd |
| 70 | 2-Br—Ph | FCH₂CO | 4-SH-Pipd |
| 71 | 4-I—Ph | 3-Cl-Prop | 4-SH-Pipd |
| 72 | 2-NO₂—Ph | c-PrCO | 4-SH-Pipd |

TABLE 1-continued

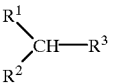

(I)

| Comp. No. | R¹ | R² | R³ |
|---|---|---|---|
| 73 | 2-F—Ph | 2,2-diF-c-PrCO | 4-SH-Pipd |
| 74 | 2-CN—Ph | c-PrCO | 4-SH-Pipd |
| 75 | 4-CN—Ph | Prop | 4-SH-Pipd |
| 76 | 2-F-4-Me—Ph | NCCH$_2$CO | 4-SH-Pipd |
| 77 | 2-CF$_3$—Ph | c-PrCO | 4-SH-Pipd |
| 78 | 2-F-4-OMe—Ph | MeOCH$_2$CO | 4-SH-Pipd |
| 79 | 2-F—Ph | 2-F-c-PrCO | 4-SH-Pipd |
| 80 | Pent-F—Ph | Ac | 4-SH-Pipd |
| 81 | 2,6-di-F—Ph | 3-F-Prop | 4-SH-Pipd |
| 82 | 2-F—Ph | c-PrCO | 4-SH-Pipd |
| 83 | 2,4-di-F—Ph | c-BuCO | 4-SH-Pipd |
| 84 | 2-F-6-Cl—Ph | Bur | 4-SH-Pipd |
| 85 | 2-F-6-CN—Ph | HOCH$_2$CO | 4-SH-Pipd |
| 86 | 2-F-6-NO$_2$—Ph | CF$_3$CO | 4-SH-Pipd |
| 87 | Ph | BuOCO | 4-SH-Pipd |
| 88 | 2-F—Ph | MeOCO | 4-SH-Pipd |
| 89 | 3-F—Ph | EtOCO | 4-SH-Pipd |
| 90 | 4-F—Ph | PrOCO | 4-SH-Pipd |
| 91 | 2-Cl—Ph | MeOCO | 4-SH-Pipd |
| 92 | 3-Cl—Ph | i-PrOCO | 4-SH-Pipd |
| 93 | 4-Cl—Ph | i-BuOCO | 4-SH-Pipd |
| 94 | Ph | CHO | 4-(CH$_2$SH)-Pipd |
| 95 | 2-F—Ph | Ac | 4-(CH$_2$SH)-Pipd |
| 96 | 3-F—Ph | PhCO | 4-(CH$_2$SH)-Pipd |
| 97 | 4-F—Ph | 4-F—PhCO | 4-(CH$_2$SH)-Pipd |
| 98 | 2-Cl—Ph | c-PrCO | 4-(CH$_2$SH)-Pipd |
| 99 | 3-Cl—Ph | 2,4-diF—PhCO | 4-(CH$_2$SH)-Pipd |
| 100 | 4-Cl—Ph | i-Bur | 4-(CH$_2$SH)-Pipd |
| 101 | 2-Br—Ph | FCH$_2$CO | 4-(CH$_2$SH)-Pipd |
| 102 | 4-I—Ph | 3-Cl-Prop | 4-(CH$_2$SH)-Pipd |
| 103 | 2-NO$_2$—Ph | c-PrCO | 4-(CH$_2$SH)-Pipd |
| 104 | 2-F—Ph | 2,2-diF-c-PrCO | 4-(CH$_2$SH)-Pipd |
| 105 | 2-CN—Ph | c-PrCO | 4-(CH$_2$SH)-Pipd |
| 106 | 4-CN—Ph | Prop | 4-(CH$_2$SH)-Pipd |
| 107 | 2-F-4-Me—Ph | NCCH$_2$CO | 4-(CH$_2$SH)-Pipd |
| 108 | 2-CF$_3$—Ph | c-PrCO | 4-(CH$_2$SH)-Pipd |
| 109 | 2-F-4-OMe—Ph | MeOCH$_2$CO | 4-(CH$_2$SH)-Pipd |
| 110 | 2-F—Ph | 2-F-c-PrCO | 4-(CH$_2$SH)-Pipd |
| 111 | Pent-F—Ph | Ac | 4-(CH$_2$SH)-Pipd |
| 112 | 2,6-di-F—Ph | 3-F-Prop | 4-(CH$_2$SH)-Pipd |
| 113 | 2-F—Ph | c-PrCO | 4-(CH$_2$SH)-Pipd |
| 114 | 2,4-di-F—Ph | c-BuCO | 4-(CH$_2$SH)-Pipd |
| 115 | 2-F-6-Cl—Ph | Bur | 4-(CH$_2$SH)-Pipd |
| 116 | 2-F-6-CN—Ph | HOCH$_2$CO | 4-(CH$_2$SH)-Pipd |
| 117 | 2-F-6-NO$_2$—Ph | CF$_3$CO | 4-(CH$_2$SH)-Pipd |
| 118 | Ph | BuOCO | 4-(CH$_2$SH)-Pipd |
| 119 | 2-F—Ph | MeOCO | 4-(CH$_2$SH)-Pipd |
| 120 | 3-F—Ph | EtOCO | 4-(CH$_2$SH)-Pipd |
| 121 | 4-F—Ph | PrOCO | 4-(CH$_2$SH)-Pipd |
| 122 | 2-Cl—Ph | MeOCO | 4-(CH$_2$SH)-Pipd |
| 123 | 3-Cl—Ph | i-PrOCO | 4-(CH$_2$SH)-Pipd |
| 124 | 4-Cl—Ph | i-BuOCO | 4-(CH$_2$SH)-Pipd |
| 125 | Ph | CHO | 3-SH-Pipd |
| 126 | 2-F—Ph | Ac | 3-SH-Pipd |
| 127 | 3-F—Ph | PhCO | 3-SH-Pipd |
| 128 | 4-F—Ph | 4-F—PhCO | 3-SH-Pipd |
| 129 | 2-Cl—Ph | c-PrCO | 3-SH-Pipd |
| 130 | 3-Cl—Ph | 2,4-diF—PhCO | 3-SH-Pipd |
| 131 | 4-Cl—Ph | i-Bur | 3-SH-Pipd |
| 132 | 2-Br—Ph | FCH$_2$CO | 3-SH-Pipd |
| 133 | 4-I—Ph | 3-Cl—Prop | 3-SH-Pipd |
| 134 | 2-NO$_2$—Ph | c-PrCO | 3-SH-Pipd |
| 135 | 2-F—Ph | 2,2-diF-c-PrCO | 3-SH-Pipd |
| 136 | 2-CN—Ph | c-PrCO | 3-SH-Pipd |
| 137 | 4-CN—Ph | Prop | 3-SH-Pipd |
| 138 | 2-F-4-Me—Ph | NCCH$_2$CO | 3-SH-Pipd |
| 139 | 2-CF$_3$—Ph | c-PrCO | 3-SH-Pipd |
| 140 | 2-F-4-OMe—Ph | MeOCH$_2$CO | 3-SH-Pipd |
| 141 | 2-F—Ph | 2-F-c-PrCO | 3-SH-Pipd |

TABLE 1-continued

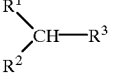

(I)

| Comp. No. | R¹ | R² | R³ |
|---|---|---|---|
| 142 | Pent-F—Ph | Ac | 3-SH-Pipd |
| 143 | 2,6-di-F—Ph | 3-F-Prop | 3-SH-Pipd |
| 144 | 2-F—Ph | c-PrCO | 3-SH-Pipd |
| 145 | 2,4-di-F—Ph | c-BuCO | 3-SH-Pipd |
| 146 | 2-F-6-Cl—Ph | Bur | 3-SH-Pipd |
| 147 | 2-F-6-CN—Ph | HOCH$_2$CO | 3-SH-Pipd |
| 148 | 2-F-6-NO$_2$—Ph | CF$_3$CO | 3-SH-Pipd |
| 149 | Ph | BuOCO | 3-SH-Pipd |
| 150 | 2-F—Ph | MeOCO | 3-SH-Pipd |
| 151 | 3-F—Ph | EtOCO | 3-SH-Pipd |
| 152 | 4-F—Ph | ProCo | 3-SH-Pipd |
| 153 | 2-Cl—Ph | MeOCO | 3-SH-Pipd |
| 154 | 3-Cl—Ph | i-PrOCO | 3-SH-Pipd |
| 155 | 4-Cl—Ph | i-BuOCO | 3-SH-Pipd |
| 156 | Ph | CHO | 3-(CH$_2$SH)-Pipd |
| 157 | 2-F—Ph | Ac | 3-(CH$_2$SH)-Pipd |
| 158 | 3-F—Ph | PhCO | 3-(CH$_2$SH)-Pipd |
| 159 | 4-F—Ph | 4-F—PhCO | 3-(CH$_2$SH)-Pipd |
| 160 | 2-Cl—Ph | c-PrCO | 3-(CH$_2$SH)-Pipd |
| 161 | 3-Cl—Ph | 2,4-diF—PhCO | 3-(CH$_2$SH)-Pipd |
| 162 | 4-Cl—Ph | i-Bur | 3-(CH$_2$SH)-Pipd |
| 163 | 2-Br—Ph | FCH$_2$CO | 3-(CH$_2$SH)Pipd |
| 164 | 4-I—Ph | 3-Cl-Prop | 3-(CH$_2$SH)-Pipd |
| 165 | 2-NO$_2$—Ph | c-PrCO | 3-(CH$_2$SH)-Pipd |
| 166 | 2-F—Ph | 2,2-diF-c-PrCO | 3-(CH$_2$SH)-Pipd |
| 167 | 2-CN—Ph | c-PrCO | 3-(CH$_2$SH)-Pipd |
| 168 | 4-CN—Ph | Prop | 3-(CH$_2$SH)-Pipd |
| 169 | 2-F-4-Me—Ph | NCCH$_2$CO | 3-(CH$_2$SH)-Pipd |
| 170 | 2-CF$_3$—Ph | c-PrCO | 3-(CH$_2$SH)-Pipd |
| 171 | 2-F-4-OMe—Ph | MeOCH$_2$CO | 3-(CH$_2$SH)-Pipd |
| 172 | 2-F—Ph | 2-F-c-PrCO | 3-(CH$_2$SH)-Pipd |
| 173 | Pent-F—Ph | Ac | 3-(CH$_2$SH)-Pipd |
| 174 | 2,6-di-F—Ph | 3-F-Prop | 3-(CH$_2$SH)-Pipd |
| 175 | 2-F—Ph | c-PrCO | 3-(CH$_2$SH)-Pipd |
| 176 | 2,4-di-F—Ph | c-BuCO | 3-(CH$_2$SH)-Pipd |
| 177 | 2-F-6-Cl—Ph | Bur | 3-(CH$_2$SH)-Pipd |
| 178 | 2-F-6-CN—Ph | HOCH$_2$CO | 3-(CH$_2$SH)-Pipd |
| 179 | 2-F-6-NO$_2$—Ph | CF$_3$CO | 3-(CH$_2$SH)-Pipd |
| 180 | Ph | BuOCO | 3-(CH$_2$SH)-Pipd |
| 181 | 2-F—Ph | MeOCO | 3-(CH$_2$SH)-Pipd |
| 182 | 3-F—Ph | EtOCO | 3-(CH$_2$SH)-Pipd |
| 183 | 4-F—Ph | PrOCO | 3-(CH$_2$SH)-Pipd |
| 184 | 2-Cl—Ph | MeOCO | 3-(CH$_2$SH)-Pipd |
| 185 | 3-Cl—Ph | i-PrOCO | 3-(CH$_2$SH)-Pipd |
| 186 | 4-Cl—Ph | i-BuOCO | 3-(CH$_2$SH)-Pipd |
| 187 | Ph | CHO | 3-SH-Azed |
| 188 | 2-F—Ph | Ac | 3-SH-Azed |
| 189 | 3-F—Ph | PhCO | 3-SH-Azed |
| 190 | 4-F—Ph | 4-F—PhCO | 3-SH-Azed |
| 191 | 2-Cl—Ph | c-PrCO | 3-SH-Azed |
| 192 | 3-Cl—Ph | 2,4-diF—PhCO | 3-SH-Azed |
| 193 | 4-Cl—Ph | i-Bur | 3-SH-Azed |
| 194 | 2-Br—Ph | FCH$_2$CO | 3-SH-Azed |
| 195 | 4-I—Ph | 3-Cl-Prop | 3-SH-Azed |
| 196 | 2-NO$_2$—Ph | c-PrCO | 3-SH-Azed |
| 197 | 2-F—Ph | 2,2-diF-c-PrCO | 3-SH-Azed |
| 198 | 2-CN—Ph | c-PrCO | 3-SH-Azed |
| 199 | 4-CN—Ph | Prop | 3-SH-Azed |
| 200 | 2-F-4-Me—Ph | NCCH$_2$CO | 3-SH-Azed |
| 201 | 2-CF$_3$—Ph | c-PrCO | 3-SH-Azed |
| 202 | 2-F-4-OMe—Ph | MeOCH$_2$CO | 3-SH-Azed |
| 203 | 2-F—Ph | 2-F-c-PrCO | 3-SH-Azed |
| 204 | Pent-F—Ph | Ac | 3-SH-Azed |
| 205 | 2,6-di-F—Ph | 3-F-Prop | 3-SH-Azed |
| 206 | 2-F—Ph | c-PrCO | 3-SH-Azed |
| 207 | 2,4-di-F—Ph | c-BuCO | 3-SH-Azed |
| 208 | 2-F-6-Cl—Ph | Bur | 3-SH-Azed |
| 209 | 2-F-6-CN—Ph | HOCH$_2$CO | 3-SH-Azed |
| 210 | 2-F-6-NO$_2$—Ph | CF$_3$CO | 3-SH-Azed |

TABLE 1-continued

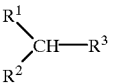

(I)

| Comp. No. | $R^1$ | $R^2$ | $R^3$ |
|---|---|---|---|
| 211 | Ph | BuOCO | 3-SH-Azed |
| 212 | 2-F—Ph | MeOCO | 3-SH-Azed |
| 213 | 3-F—Ph | EtOCO | 3-SH-Azed |
| 214 | 4-F—Ph | PrOCO | 3-SH-Azed |
| 215 | 2-Cl—Ph | MeOCO | 3-SH-Azed |
| 216 | 3-Cl—Ph | i-PrOCO | 3-SH-Azed |
| 217 | 4-Cl—Ph | i-BuOCO | 3-SH-Azed |
| 218 | Ph | CHO | 3-($CH_2SH$)-Azed |
| 219 | 2-F—Ph | Ac | 3-($CH_2SH$)-Azed |
| 220 | 3-F—Ph | PhCO | 3-($CH_2SH$)-Azed |
| 221 | 4-F—Ph | 4-F—PhCO | 3-($CH_2SH$)-Azed |
| 222 | 2-Cl—Ph | c-PrCO | 3-($CH_2SH$)-Azed |
| 223 | 3-Cl—Ph | 2,4-diF—PhCO | 3-($CH_2SH$)-Azed |
| 224 | 4-Cl—Ph | i-Bur | 3-($CH_2SH$)-Azed |
| 225 | 2-Br—Ph | $FCH_2CO$ | 3-($CH_2SH$)-Azed |
| 226 | 4-I—Ph | 3-Cl-Prop | 3-($CH_2SH$)-Azed |
| 227 | 2-$NO_2$—Ph | c-PrCO | 3-($CH_2SH$)-Azed |
| 228 | 2-F—Ph | 2,2-diF-c-PrCO | 3-($CH_2SH$)-Azed |
| 229 | 2-CN—Ph | c-PrCO | 3-($CH_2SH$)-Azed |
| 230 | 4-CN—Ph | Prop | 3-($CH_2SH$)-Azed |
| 231 | 2-F-Me—Ph | $NCCH_2CO$ | 3-($CH_2SH$)-Azed |
| 232 | 2-$CF_3$—Ph | c-PrCO | 3-($CH_2SH$)-Azed |
| 233 | 2-F-4-OMe—Ph | $MeOCH_2CO$ | 3-($CH_2SH$)-Azed |
| 234 | 2-F—Ph | 2-F-c-PrCO | 3-($CH_2SH$)-Azed |
| 235 | Pent-F—Ph | Ac | 3-($CH_2SH$)-Azed |
| 236 | 2,6-di-F—Ph | 3-F-Prop | 3-($CH_2SH$)-Azed |
| 237 | 2-F—Ph | c-PrCO | 3-($CH_2SH$)-Azed |
| 238 | 2,4-di-F—Ph | c-BuCO | 3-($CH_2SH$)-Azed |
| 239 | 2-F-6-Cl—Ph | Bur | 3-($CH_2SH$)-Azed |
| 240 | 2-F-6-CN—Ph | $HOCH_2CO$ | 3-($CH_2SH$)-Azed |
| 241 | 2-F-6-$NO_2$—Ph | $CF_3CO$ | 3-($CH_2SH$)-Azed |
| 242 | Ph | BuOCO | 3-($CH_2SH$)-Azed |
| 243 | 2-F—Ph | MeOCO | 3-($CH_2SH$)-Azed |
| 244 | 3-F—Ph | EtOCO | 3-($CH_2SH$)-Azed |
| 245 | 4-F—Ph | PrOCO | 3-($CH_2SH$)-Azed |
| 246 | 2-Cl—Ph | MeOCO | 3-($CH_2SH$)-Azed |
| 247 | 3-Cl—Ph | i-PrOCO | 3-($CH_2SH$)-Azed |
| 248 | 4-Cl—Ph | i-BuOCO | 3-($CH_2SH$)-Azed |
| 249 | Ph | CHO | 3-SH—ABOc |
| 250 | 2-F—Ph | Ac | 3-SH—ABOc |
| 251 | 3-F—Ph | PhCO | 3-SH—ABOc |
| 252 | 4-F—Ph | 4-F—PhCO | 3-SH—ABOc |
| 253 | 2-Cl—Ph | c-PrCO | 3-SH—ABOc |
| 254 | 3-Cl—Ph | 2,4-diF—PhCO | 3-SH—ABOc |
| 255 | 4-Cl—Ph | i-Bur | 3-SH—ABOc |
| 256 | 2-Br—Ph | $FCH_2CO$ | 3-SH—ABOc |
| 257 | 4-I—Ph | 3-Cl-Prop | 3-SH—ABOc |
| 258 | 2-$NO_2$—Ph | c-PrCO | 3-SH—ABOc |
| 259 | 2-F—Ph | 2,2-diF-c-PrCO | 3-SH—ABOc |
| 260 | 2-CN—Ph | c-PrCO | 3-SH—ABOc |
| 261 | 4-CN—Ph | Prop | 3-SH—ABOc |
| 262 | 2-F-4-Me—Ph | $NCCH_2CO$ | 3-SH—ABOc |
| 263 | 2-$CF_3$—Ph | c-PrCO | 3-SH—ABOc |
| 264 | 2-F-4-OMe—Ph | $MeOCH_2CO$ | 3-SH—ABOc |
| 265 | 2-F—Ph | 2-F-c-PrCO | 3-SH—ABOc |
| 266 | Pent-F—Ph | Ac | 3-SH—ABOc |
| 267 | 2,6-di-F—Ph | 3-F-Prop | 3-SH—ABOc |
| 268 | 2-F—Ph | c-PrCO | 3-SH—ABOc |
| 269 | 2,4-di-F—Ph | c-BuCO | 3-SH—ABOc |
| 270 | 2-F-6-Cl—Ph | Bur | 3-SH—ABOc |
| 271 | 2-F-6-CN—Ph | $HOCH_2CO$ | 3-SH—ABOc |
| 272 | 2-F-6-$NO_2$—Ph | $CF_3CO$ | 3-SH—ABOc |
| 273 | Ph | BuOCO | 3-SH—ABOc |
| 274 | 2-F—Ph | MeOCO | 3-SH—ABOc |
| 275 | 3-F—Ph | EtOCO | 3-SH—ABOc |
| 276 | 4-F—Ph | PrOCO | 3-SH—ABOc |
| 277 | 2-Cl—Ph | MeOCO | 3-SH—ABOc |
| 278 | 3-Cl—Ph | i-PrOCO | 3-SH—ABOc |
| 279 | 4-Cl—Ph | i-BuOCO | 3-SH—ABOc |

TABLE 1-continued

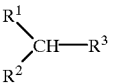

(I)

| Comp. No. | R¹ | R² | R³ |
|---|---|---|---|
| 280 | Ph | CHO | 3-(CH$_2$SH)—ABOc |
| 281 | 2-F—Ph | Ac | 3-(CH$_2$SH)—ABOc |
| 282 | 3-F—Ph | PhCO | 3-(CH$_2$SH)—ABOc |
| 283 | 4-F—Ph | 4-F—PhCO | 3-(CH$_2$SH)—ABOc |
| 284 | 2-Cl—Ph | c-PrCO | 3-(CH$_2$SH)—ABOc |
| 285 | 3-Cl—Ph | 2,4-diF—PhCO | 3-(CH$_2$SH)—ABOc |
| 286 | 4-Cl—Ph | i-Bur | 3-(CH$_2$SH)—ABOc |
| 287 | 2-Br—Ph | FCH$_2$CO | 3-(CH$_2$SH)—ABOc |
| 288 | 4-I—Ph | 3-Cl-Prop | 3-(CH$_2$SH)—ABOc |
| 289 | 2-NO$_2$—Ph | c-PrCO | 3-(CH$_2$SH)—ABOc |
| 290 | 2-F—Ph | 2,2-diF-c-PrCO | 3-(CH$_2$SH)—ABOc |
| 291 | 2-CN—Ph | c-PrCO | 3-(CH$_2$SH)—ABOc |
| 292 | 4-CN—Ph | Prop | 3-(CH$_2$SH)—ABOc |
| 293 | 2-F-4-Me—Ph | NCCH$_2$CO | 3-(CH$_2$SH)—ABOc |
| 294 | 2-CF$_3$—Ph | c-PrCO | 3-(CH$_2$SH)—ABOc |
| 295 | 2-F-4-OMe—Ph | MeOCH$_2$CO | 3-(CH$_2$SH)—ABOc |
| 296 | 2-F—Ph | 2-F-c-PrCO | 3-(CH$_2$SH)—ABOc |
| 297 | Pent-F—Ph | Ac | 3-(CH$_2$SH)—ABOc |
| 298 | 2,6-di-F—Ph | 3-F-Prop | 3-(CH$_2$SH)—ABOc |
| 299 | 2-F—Ph | c-PrCO | 3-(CH$_2$SH)—ABOc |
| 300 | 2,4-di-F—Ph | c-BuCO | 3-(CH$_2$SH)—ABOc |
| 301 | 2-F-6-Cl—Ph | Bur | 3-(CH$_2$SH)—ABOc |
| 302 | 2-F-6-CN—Ph | HOCH$_2$CO | 3-(CH$_2$SH)—ABOc |
| 303 | 2-F-6-NO$_2$—Ph | CF$_3$CO | 3-(CH$_2$SH)—ABOc |
| 304 | Ph | BuOCO | 3-(CH$_2$SH)—ABOc |
| 305 | 2-F—Ph | MeOCO | 3-(CH$_2$SH)—ABOc |
| 306 | 3-F—Ph | EtOCO | 3-(CH$_2$SH)—ABOC |
| 307 | 4-F—Ph | PrOCO | 3-(CH$_2$SH)—ABOC |
| 308 | 2-Cl—Ph | MeOCO | 3-(CH$_2$SH)—ABOc |
| 309 | 3-Cl—Ph | i-PrOCO | 3-(CH$_2$SH)—ABOc |
| 310 | 4-Cl—Ph | i-BuOCO | 3-(CH$_2$SH)—ABOc |
| 311 | Ph | Ac | 4-SH-3-(=CH$_2$)Pipd |
| 312 | 2-F—Ph | Prop | 4-SH-3-(=CH$_2$)Pipd |
| 313 | 2-Cl—Ph | Ac | 4-SH-3-(=CH$_2$)Pipd |
| 314 | 2-F—Ph | c-PrCO | 4-SH-3-(=CH$_2$)Pipd |
| 315 | 2-Cl—Ph | Prop | 4-SH-3-(=CH$_2$)Pipd |
| 316 | 2-F—Ph | Ac | 4-SH-3-(=CH$_2$)Pipd |
| 317 | 2-Cl—Ph | c-PrCO | 4-SH-3-(=CH$_2$)Pipd |
| 318 | 2-F—Ph | c-BuCO | 4-SH-3-(=CH$_2$)Pipd |
| 319 | 2-Cl—Ph | Bur | 4-SH-3-(=CH$_2$)Pipd |
| 320 | 2-F—Ph | PhCO | 4-SH-3-(=CH$_2$)Pipd |
| 321 | 2-Cl—Ph | c-BuCO | 4-SH-3-(=CH$_2$)Pipd |
| 322 | 2,4-di-F—Ph | c-PrCO | 4-SH-3-(=CH$_2$)Pipd |
| 323 | 2,6-di-F—Ph | Ac | 4-SH-3-(=CH$_2$)Pipd |
| 324 | 2-F—Ph | MeOCO | 4-SH-3-(=CH$_2$)Pipd |
| 325 | 2-Cl—Ph | EtOCO | 4-SH-3-(=CH$_2$)Pipd |
| 326 | 2-F—Ph | PrOCO | 4-SH-3-(=CH$_2$)Pipd |
| 327 | 2-Cl—Ph | MeOCO | 4-SH-3-(=CH$_2$)Pipd |
| 328 | 2-F—Ph | EtOCO | 4-SH-3-(=CH$_2$)Pipd |
| 329 | 3-F—Ph | MeOCO | 4-SH-3-(=CH$_2$)Pipd |
| 330 | 3-Cl—Ph | EtOCO | 4-SH-3-(=CH$_2$)Pipd |
| 331 | 3-F—Ph | PrOCO | 4-SH-3-(=CH$_2$)Pipd |
| 332 | 2-F—Ph | BuOCO | 4-SH-3-(=CH$_2$)Pipd |
| 333 | Ph | Ac | 4-SH-3-(=CHMe)Pipd |
| 334 | 2-F—Ph | Prop | 4-SH-3-(=CHMe)Pipd |
| 335 | 2-Cl—Ph | Ac | 4-SH-3-(=CHMe)Pipd |
| 336 | 2-F—Ph | c-PrCO | 4-SH-3-(=CHMe)Pipd |
| 337 | 2-Cl—Ph | Prop | 4-SH-3-(=CHMe)Pipd |
| 338 | 2-F—Ph | Ac | 4-SH-3-(=CHMe)Pipd |
| 339 | 2-Cl—Ph | c-PrCO | 4-SH-3-(=CHMe)Pipd |
| 340 | 2-F—Ph | c-BuCO | 4-SH-3-(=CHMe)Pipd |
| 341 | 2-Cl—Ph | Bur | 4-SH-3-(=CHMe)Pipd |
| 342 | 2-F—Ph | PhCO | 4-SH-3-(=CHMe)Pipd |
| 343 | 2-Cl—Ph | c-BuCO | 4-SH-3-(=CHMe)Pipd |
| 344 | 2,4-di-F—Ph | c-PrCO | 4-SH-3-(=CHMe)Pipd |
| 345 | 2,6-di-F—Ph | Ac | 4-SH-3-(=CHMe)Pipd |
| 346 | 2-F—Ph | MeOCO | 4-SH-3-(=CHMe)Pipd |
| 347 | 2-Cl—Ph | EtOCO | 4-SH-3-(=CHMe)Pipd |
| 348 | 2-F—Ph | PrOCO | 4-SH-3-(=CHMe)Pipd |

TABLE 1-continued

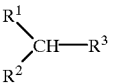

(I)

| Comp. No. | R¹ | R² | R³ |
|---|---|---|---|
| 349 | 2-Cl—Ph | MeOCO | 4-SH-3-(=CHMe)Pipd |
| 350 | 2-F—Ph | EtOCO | 4-SH-3-(=CHMe)Pipd |
| 351 | 3-F—Ph | MeOCO | 4-SH-3-(=CHMe)Pipd |
| 352 | 3-Cl—Ph | EtOCO | 4-SH-3-(=CHMe)Pipd |
| 353 | 3-F—Ph | PrOCO | 4-SH-3-(=CHMe)Pipd |
| 354 | 2-F—Ph | BuOCO | 4-SH-3-(=CHMe)Pipd |
| 355 | Ph | Ac | 4-SH-3-(=CHEt)Pipd |
| 356 | 2-F—Ph | Prop | 4-SH-3-(=CHEt)Pipd |
| 357 | 2-Cl—Ph | Ac | 4-SH-3-(=CHEt)Pipd |
| 358 | 2-F—Ph | c-PrCO | 4-SH-3-(=CHEt)Pipd |
| 359 | 2-Cl—Ph | Prop | 4-SH-3-(=CHEt)Pipd |
| 360 | 2-F—Ph | Ac | 4-SH-3-(=CHEt)Pipd |
| 361 | 2-Cl—Ph | c-PrCO | 4-SH-3-(=CHEt)Pipd |
| 362 | 2-F—Ph | c-BuCO | 4-SH-3-(=CHEt)Pipd |
| 363 | 2-Cl—Ph | Bur | 4-SH-3-(=CHEt)Pipd |
| 364 | 2-F—Ph | PhCO | 4-SH-3-(=CHEt)Pipd |
| 365 | 2-Cl—Ph | c-BuCO | 4-SH-3-(=CHEt)Pipd |
| 366 | 2,4-di-F—Ph | c-PrCO | 4-SH-3-(=CHEt)Pipd |
| 367 | 2,6-di-F—Ph | Ac | 4-SH-3-(=CHEt)Pipd |
| 368 | 2-F—Ph | MeOCO | 4-SH-3-(=CHEt)Pipd |
| 369 | 2-Cl—Ph | EtOCO | 4-SH-3-(=CHEt)Pipd |
| 370 | 2-F—Ph | PrOCO | 4-SH-3-(=CHEt)Pipd |
| 371 | 2-Cl—Ph | MeOCO | 4-SH-3-(=CHEt)Pipd |
| 372 | 2-F—Ph | EtOCO | 4-SH-3-(=CHEt)Pipd |
| 373 | 3-F—Ph | MeOCO | 4-SH-3-(=CHEt)Pipd |
| 374 | 3-Cl—Ph | EtOCO | 4-SH-3-(=CHEt)Pipd |
| 375 | 3-F—Ph | PrOCO | 4-SH-3-(=CHEt)Pipd |
| 376 | 2-F—Ph | BuOCO | 4-SH-3-(=CHEt)Pipd |
| 377 | 2-Cl—Ph | PhCO | 4-SH-3-(=CHPr)Pipd |
| 378 | 2-F—Ph | Prop | 4-SH-3-(=CHPr)Pipd |
| 379 | 2-Cl—Ph | Ac | 4-SH-3-(=CHPr)Pipd |
| 380 | 2-F—Ph | c-PrCO | 4-SH-3-(=CHPr)Pipd |
| 381 | 2-Cl—Ph | c-BuCO | 4-SH-3-(=CHPr)Pipd |
| 382 | 2-F—Ph | MeOCO | 4-SH-3-(=CHPr)Pipd |
| 383 | 2-Cl—Ph | c-PrCO | 4-SH-3-(=CHPr)Pipd |
| 384 | 2-F—Ph | EtOCO | 4-SH-3-(=CHPr)Pipd |
| 385 | 2-Cl—Ph | MeOCO | 4-SH-3-(=CHPr)Pipd |
| 386 | 2-F—Ph | PrOCO | 4-SH-3-(=CHPr)Pipd |
| 387 | 2-Cl—Ph | PhCO | 4-SH-3-(=CHBu)Pipd |
| 388 | 2-F—Ph | Prop | 4-SH-3-(=CHBu)Pipd |
| 389 | 2-Cl—Ph | Ac | 4-SH-3-(=CHBu)Pipd |
| 390 | 2-F—Ph | c-PrCO | 4-SH-3-(=CHBu)Pipd |
| 391 | 2-Cl—Ph | c-BuCO | 4-SH-3-(=CHBu)Pipd |
| 392 | 2-F—Ph | MeOCO | 4-SH-3-(=CHBu)Pipd |
| 393 | 2-Cl—Ph | c-PrCO | 4-SH-3-(=CHBu)Pipd |
| 394 | 2-F—Ph | EtOCO | 4-SH-3-(=CHBu)Pipd |
| 395 | 2-Cl—Ph | MeOCO | 4-SH-3-(=CHBu)Pipd |
| 396 | 2-F—Ph | PrOCO | 4-SH-3-(=CHBu)Pipd |
| 397 | Ph | Ac | 4-SH-3-(=CHCO$_2$Me)Pipd |
| 398 | 2-F—Ph | Prop | 4-SH-3-(=CHCO$_2$Me)Pipd |
| 399 | 2-Cl—Ph | Ac | 4-SH-3-(=CHCO$_2$Me)Pipd |
| 400 | 2-F—Ph | c-PrCO | 4-SH-3-(=CHCO$_2$Me)Pipd |
| 401 | 2-Cl—Ph | Prop | 4-SH-3-(=CHCO$_2$Me)Pipd |
| 402 | 2-F—Ph | Ac | 4-SH-3-(=CHCO$_2$Me)Pipd |
| 403 | 2-Cl—Ph | c-PrCO | 4-SH-3-(=CHCO$_2$Me)Pipd |
| 404 | 2-F—Ph | c-BuCO | 4-SH-3-(=CHCO$_2$Me)Pipd |
| 405 | 2-Cl—Ph | Bur | 4-SH-3-(=CHCO$_2$Me)Pipd |
| 406 | 2-F—Ph | PhCO | 4-SH-3-(=CHCO$_2$Me)Pipd |
| 407 | 2-Cl—Ph | c-BuCO | 4-SH-3-(=CHCO$_2$Me)Pipd |
| 408 | 2,4-di-F—Ph | c-PrCO | 4-SH-3-(=CHCO$_2$Me)Pipd |
| 409 | 2,6-di-F—Ph | Ac | 4-SH-3-(=CHCO$_2$Me)Pipd |
| 410 | 2-F—Ph | MeOCO | 4-SH-3-(=CHCO$_2$Me)Pipd |
| 411 | 2-Cl—Ph | EtOCO | 4-SH-3-(=CHCO$_2$Me)Pipd |
| 412 | 2-F—Ph | PrOCO | 4-SH-3-(=CHCO$_2$Me)Pipd |
| 413 | 2-Cl—Ph | MeOCO | 4-SH-3-(=CHCO$_2$Me)Pipd |
| 414 | 2-F—Ph | EtOCO | 4-SH-3-(=CHCO$_2$Me)Pipd |
| 415 | 3-F—Ph | MeOCO | 4-SH-3-(=CHCO$_2$Me)Pipd |
| 416 | 3-Cl—Ph | EtOCO | 4-SH-3-(=CHCO$_2$Me)Pipd |
| 417 | 3-F—Ph | PrOCO | 4-SH-3-(=CHCO$_2$Me)Pipd |

TABLE 1-continued

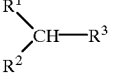

(I)

| Comp. No. | R¹ | R² | R³ |
|---|---|---|---|
| 418 | 2-F—Ph | BuOCO | 4-SH-3-(=CHCO₂Me)Pipd |
| 419 | Ph | Ac | 4-SH-3-(=CHCO₂Et)Pipd |
| 420 | 2-F—Ph | Prop | 4-SH-3-(=CHCO₂Et)Pipd |
| 421 | 2-Cl—Ph | Ac | 4-SH-3-(=CHCO₂Et)Pipd |
| 422 | 2-F—Ph | c-PrCO | 4-SH-3-(=CHCO₂Et)Pipd |
| 423 | 2-Cl—Ph | Prop | 4-SH-3-(=CHCO₂Et)Pipd |
| 424 | 2-F—Ph | Ac | 4-SH-3-(=CHCO₂Et)Pipd |
| 425 | 2-Cl—Ph | c-PrCO | 4-SH-3-(=CHCO₂Et)Pipd |
| 426 | 2-F—Ph | c-BuCO | 4-SH-3-(=CHCO₂Et)Pipd |
| 427 | 2-Cl—Ph | Bur | 4-SH-3-(=CHCO₂Et)Pipd |
| 428 | 2-F—Ph | PhCO | 4-SH-3-(=CHCO₂Et)Pipd |
| 429 | 2-Cl—Ph | c-BuCO | 4-SH-3-(=CHCO₂Et)Pipd |
| 430 | 2,4-di-F—Ph | c-PrCO | 4-SH-3-(=CHCO₂Et)Pipd |
| 431 | 2,6-di-F—Ph | Ac | 4-SH-3-(=CHCO₂Et)Pipd |
| 432 | 2-F—Ph | MeOCO | 4-SH-3-(=CHCO₂Et)Pipd |
| 433 | 2-Cl—Ph | EtOCO | 4-SH-3-(=CHCO₂Et)Pipd |
| 434 | 2-F—Ph | PrOCO | 4-SH-3-(=CHCO₂Et)Pipd |
| 435 | 2-Cl—Ph | MeOCO | 4-SH-3-(=CHCO₂Et)Pipd |
| 436 | 2-F—Ph | EtOCO | 4-SH-3-(=CHCO₂Et)Pipd |
| 437 | 3-F—Ph | MeOCO | 4-SH-3-(=CHCO₂Et)Pipd |
| 438 | 3-Cl—Ph | EtOCO | 4-SH-3-(=CHCO₂Et)Pipd |
| 439 | 3-F—Ph | PrOCO | 4-SH-3-(=CHCO₂Et)Pipd |
| 440 | 2-F—Ph | BuOCO | 4-SH-3-(=CHCO₂Et)Pipd |
| 441 | 2-Cl—Ph | PhCO | 4-SH-3-(=CHCO₂Pr)Pipd |
| 442 | 2-F—Ph | Prop | 4-SH-3-(=CHCO₂Pr)Pipd |
| 443 | 2-Cl—Ph | Ac | 4-SH-3-(=CHCO₂Pr)Pipd |
| 444 | 2-F—Ph | c-PrCO | 4-SH-3-(=CHCO₂Pr)Pipd |
| 445 | 2-Cl—Ph | c-BuCO | 4-SH-3-(=CHCO₂Pr)Pipd |
| 446 | 2-F—Ph | MeOCO | 4-SH-3-(=CHCO₂Pr)Pipd |
| 447 | 2-Cl—Ph | c-PrCO | 4-SH-3-(=CHCO₂Pr)Pipd |
| 448 | 2-F—Ph | EtOCO | 4-SH-3-(=CHCO₂Pr)Pipd |
| 449 | 2-Cl—Ph | MeOCO | 4-SH-3-(=CHCO₂Pr)Pipd |
| 450 | 2-F—Ph | PrOCO | 4-SH-3-(=CHCO₂Pr)Pipd |
| 451 | 2-Cl—Ph | PhCO | 4-SH-3-(=CHCO₂Bu)Pipd |
| 452 | 2-F—Ph | Prop | 4-SH-3-(=CHCO₂Bu)Pipd |
| 453 | 2-Cl—Ph | Ac | 4-SH-3-(=CHCO₂Bu)Pipd |
| 454 | 2-F—Ph | c-PrCO | 4-SH-3-(=CHCO₂Bu)Pipd |
| 455 | 2-Cl—Ph | c-BuCO | 4-SH-3-(=CHCO₂Bu)Pipd |
| 456 | 2-F—Ph | MeOCO | 4-SH-3-(=CHCO₂Bu)Pipd |
| 457 | 2-Cl—Ph | c-PrCO | 4-SH-3-(=CHCO₂Bu)Pipd |
| 458 | 2-F—Ph | EtOCO | 4-SH-3-(=CHCO₂Bu)Pipd |
| 459 | 2-Cl—Ph | MeOCO | 4-SH-3-(=CHCO₂Bu)Pipd |
| 460 | 2-F—Ph | PrOCO | 4-SH-3-(=CHCO₂Bu)Pipd |
| 461 | Ph | Ac | 4-SH-3-(=CHCOOH)Pipd |
| 462 | 2-F—Ph | Prop | 4-SH-3-(=CHCOOH)Pipd |
| 463 | 2-Cl—Ph | Ac | 4-SH-3-(=CHCOOH)Pipd |
| 464 | 2-F—Ph | c-PrCO | 4-SH-3-(=CHCOOH)Pipd |
| 465 | 2-Cl—Ph | Prop | 4-SH-3-(=CHCOOH)Pipd |
| 466 | 2-F—Ph | Ac | 4-SH-3-(=CHCOOH)Pipd |
| 467 | 2-Cl—Ph | c-PrCO | 4-SH-3-(=CHCOOH)Pipd |
| 468 | 2-F—Ph | c-BuCO | 4-SH-3-(=CHCOOH)Pipd |
| 469 | 2-Cl—Ph | Bur | 4-SH-3-(=CHCOOH)Pipd |
| 470 | 2-F—Ph | PhCO | 4-SH-3-(=CHCOOH)Pipd |
| 471 | 2-Cl—Ph | c-BuCO | 4-SH-3-(=CHCOOH)Pipd |
| 472 | 2,4-di-F—Ph | c-PrCO | 4-SH-3-(=CHCOOH)Pipd |
| 473 | 2,6-di-F—Ph | Ac | 4-SH-3-(=CHCOOH)Pipd |
| 474 | 2-F—Ph | MeOCO | 4-SH-3-(=CHCOOH)Pipd |
| 475 | 2-Cl—Ph | EtOCO | 4-SH-3-(=CHCOOH)Pipd |
| 476 | 2-F—Ph | PrOCO | 4-SH-3-(=CHCOOH)Pipd |
| 477 | 2-Cl—Ph | MeOCO | 4-SH-3-(=CHCOOH)Pipd |
| 478 | 2-F—Ph | EtOCO | 4-SH-3-(=CHCOOH)Pipd |
| 479 | 3-F—Ph | MeOCO | 4-SH-3-(=CHCOOH)Pipd |
| 480 | 3-Cl—Ph | EtOCO | 4-SH-3-(=CHCOOH)Pipd |
| 481 | 3-F—Ph | PrOCO | 4-SH-3-(=CHCOOH)Pipd |
| 482 | 2-F—Ph | BuOCO | 4-SH-3-(=CHCOOH)Pipd |
| 483 | Ph | Ac | 4-SH-3-(=CHCONMe₂)Pipd |
| 484 | 2-F—Ph | Prop | 4-SH-3-(=CHCONMe₂)Pipd |
| 485 | 2-Cl—Ph | Ac | 4-SH-3-(=CHCONMe₂)Pipd |
| 486 | 2-F—Ph | c-PrCO | 4-SH-3-(=CHCONMe₂)Pipd |

TABLE 1-continued

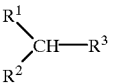

(I)

| Comp. No. | $R^1$ | $R^2$ | $R^3$ |
|---|---|---|---|
| 487 | 2-Cl—Ph | Prop | 4-SH-3-(=CHCONMe$_2$)Pipd |
| 488 | 2-F—Ph | Ac | 4-SH-3-(=CHCONMe$_2$)Pipd |
| 489 | 2-Cl—Ph | c-PrCO | 4-SH-3-(=CHCONMe$_2$)Pipd |
| 490 | 2-F—Ph | c-BuCO | 4-SH-3-(=CHCONMe$_2$)Pipd |
| 491 | 2-Cl—Ph | Bur | 4-SH-3-(=CHCONMe$_2$)Pipd |
| 492 | 2-F—Ph | PhCO | 4-SH-3-(=CHCONMe$_2$)Pipd |
| 493 | 2-Cl—Ph | c-BuCO | 4-SH-3-(=CHCONMe$_2$)Pipd |
| 494 | 2,4-di-F—Ph | c-PrCO | 4-SH-3-(=CHCONMe$_2$)Pipd |
| 495 | 2,6-di-F—Ph | Ac | 4-SH-3-(=CHCONMe$_2$)Pipd |
| 496 | 2-F—Ph | MeOCO | 4-SH-3-(=CHCONMe$_2$)Pipd |
| 497 | 2-Cl—Ph | EtOCO | 4-SH-3-(=CHCONMe$_2$)Pipd |
| 498 | 2-F—Ph | PrOCO | 4-SH-3-(=CHCONMe$_2$)Pipd |
| 499 | 2-Cl—Ph | MeOCO | 4-SH-3-(=CHCONMe$_2$)Pipd |
| 500 | 2-F—Ph | EtOCO | 4-SH-3-(=CHCONMe$_2$)Pipd |
| 501 | 3-F—Ph | MeOCO | 4-SH-3-(=CHCONMe$_2$)Pipd |
| 502 | 3-Cl—Ph | EtOCO | 4-SH-3-(=CHCONMe$_2$)Pipd |
| 503 | 3-F—Ph | PrOCO | 4-SH-3-(=CHCONMe2)Pipd |
| 504 | 2-F—Ph | BuOCO | 4-SH-3-(=CHCONMe$_2$)Pipd |
| 503 | Ph | Ac | 4-SH-3-(=CHCONHMe)Pipd |
| 506 | 2-F—Ph | Prop | 4-SH-3-(=CHCONHMe)Pipd |
| 507 | 2-Cl—Ph | Ac | 4-SH-3-(=CHCONHMe)Pipd |
| 508 | 2-F—Ph | c-PrCO | 4-SH-3-(=CHCONHMe)Pipd |
| 509 | 2-Cl—Ph | Prop | 4-SH-3-(=CHCONHMe)Pipd |
| 510 | 2-F—Ph | Ac | 4-SH-3-(=CHCONHMe)Pipd |
| 511 | 2-Cl—Ph | c-PrCO | 4-SH-3-(=CHCONHMe)Pipd |
| 512 | 2-F—Ph | c-BuCO | 4-SH-3-(=CHCONHMe)Pipd |
| 513 | 2-Cl—Ph | Bur | 4-SH-3-(=CHCONMe$_2$)Pipd |
| 514 | 2-F—Ph | PhCO | 4-SH-3-(=CHCONHMe)Pipd |
| 515 | 2-Cl—Ph | c-BuCO | 4-SH-3-(=CHCONHMe)Pipd |
| 516 | 2,4-di-F—Ph | c-PrCO | 4-SH-3-(=CHCONHMe)Pipd |
| 517 | 2,6-di-F—Ph | Ac | 4-SH-3-(=CHCONHMe)Pipd |
| 518 | 2-F—Ph | MeOCO | 4-SH-3-(=CHCONHMe)Pipd |
| 519 | 2-Cl—Ph | EtOCO | 4-SH-3-(=CHCONHMe)Pipd |
| 520 | 2-F—Ph | PrOCO | 4-SH-3-(=CHCONHMe)Pipd |
| 521 | 2-Cl—Ph | MeOCO | 4-SH-3-(=CHCONHMe)Pipd |
| 522 | 2-F—Ph | EtOCO | 4-SH-3-(=CHCONHMe)Pipd |
| 523 | 3-F—Ph | MeOCO | 4-SH-3-(=CHCONHMe)Pipd |
| 524 | 3-Cl—Ph | EtOCO | 4-SH-3-(=CHCONHMe)Pipd |
| 525 | 3-F—Ph | PrOCO | 4-SH-3-(=CHCONHMe)Pipd |
| 526 | 2-F—Ph | BuOCO | 4-SH-3-(=CHCONHMe)Pipd |
| 527 | 2-Cl—Ph | PhCO | 4-SH-3-(=CHCONH$_2$)Pipd |
| 528 | 2-F—Ph | Prop | 4-SH-3-(=CHCONH$_2$)Pipd |
| 529 | 2-Cl—Ph | Ac | 4-SH-3-(=CHCONH$_2$)Pipd |
| 530 | 2-F—Ph | c-PrCO | 4-SH-3-(=CHCONH$_2$)Pipd |
| 531 | 2-Cl—Ph | c-BuCO | 4-SH-3-(=CHCONH$_2$)Pipd |
| 532 | 2-F—Ph | MeOCO | 4-SH-3-(=CHCONH$_2$)Pipd |
| 533 | 2-Cl—Ph | c-PrCO | 4-SH-3-(=CHCONH$_2$)Pipd |
| 534 | 2-F—Ph | EtOCO | 4-SH-3-(=CHCONH$_2$)Pipd |
| 535 | 2-Cl—Ph | MeOCO | 4-SH-3-(=CHCONH$_2$)Pipd |
| 536 | 2-F—Ph | PrOCO | 4-SH-3-(=CHCONH$_2$)Pipd |
| 537 | 2-Cl—Ph | PhCO | 4-SH-3-(=CHCONHEt)Pipd |
| 538 | 2-F—Ph | Prop | 4-SH-3-(=CHCONHEt)Pipd |
| 539 | 2-Cl—Ph | Ac | 4-SH-3-(=CHCONHEt)Pipd |
| 540 | 2-F—Ph | c-PrCO | 4-SH-3-(=CHCONHEt)Pipd |
| 541 | 2-Cl—Ph | c-BuCO | 4-SH-3-(=CHCONHEt)Pipd |
| 542 | 2-F—Ph | MeOCO | 4-SH-3-(=CHCONHEt)Pipd |
| 543 | 2-Cl—Ph | c-PrCO | 4-SH-3-(=CHCONHEt)Pipd |
| 544 | 2-F—Ph | EtOCO | 4-SH-3-(=CHCONHEt)Pipd |
| 545 | 2-Cl—Ph | MeOCO | 4-SH-3-(=CHCONHEt)Pipd |
| 546 | 2-F—Ph | PrOCO | 4-SH-3-(=CHCONHEt)Pipd |
| 547 | 2-F—Ph | Prop | 3-SH-Pyrd |
| 548 | 2-F—Ph | Prop | 3-SAc-Pyrd |
| 549 | 2-F—Ph | Prop | 3-SProp-Pyrd |
| 550 | 2-Cl—Ph | Prop | 3-SH-Pyrd |
| 551 | 2-Cl—Ph | Prop | 3-SAc-Pyrd |
| 552 | 2-F—Ph | c-PrCO | 3-SAc-Pyrd |
| 553 | 2-F—Ph | c-PrCO | 3-SProp-Pyrd |
| 554 | 2-Cl—Ph | c-PrCO | 3-SAc-Pyrd |
| 555 | 2-F—Ph | MeOCO | 3-SAc-Pyrd |

TABLE 1-continued

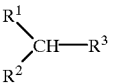

(I)

| Comp. No. | R¹ | R² | R³ |
|---|---|---|---|
| 556 | 2-F—Ph | MeOCO | 3-SProp-Pyrd |
| 557 | 2-F—Ph | EtOCO | 3-SAc-Pyrd |
| 558 | 2-Cl—Ph | MeOCO | 3-SAc-Pyrd |
| 559 | 2-Cl—Ph | EtOCO | 3-SAc-Pyrd |
| 560 | 2-F—Ph | Prop | 3-CH₂SH-Pyrd |
| 561 | 2-F—Ph | Prop | 3-CH₂SAc-Pyrd |
| 562 | 2-F—Ph | Prop | 3-CH₂Prop-Pyrd |
| 563 | 2-Cl—Ph | Prop | 3-CH₂SH-Pyrd |
| 564 | 2-Cl—Ph | Prop | 3-CH₂SAc-Pyrd |
| 565 | 2-F—Ph | c-PrCO | 3-CH₂SAc-Pyrd |
| 566 | 2-F—Ph | c-PrCO | 3-CH₂SProp-Pyrd |
| 567 | 2-Cl—Ph | c-PrCO | 3-CH₂SAc-Pyrd |
| 568 | 2-F—Ph | MeOCO | 3-CH₂SAc-Pyrd |
| 569 | 2-F—Ph | MeOCO | 3-CH₂SProp-Pyrd |
| 570 | 2-F—Ph | EtOCO | 3-CH₂SAc-Pyrd |
| 571 | 2-Cl—Ph | MeOCO | 3-CH₂SAc-Pyrd |
| 572 | 2-Cl—Ph | EtOCO | 3-CH₂SAc-Pyrd |
| 573 | 2-F—Ph | Ac | 4-SAc-Pipd |
| 574 | 2-F—Ph | Prop | 4-SH-Pipd |
| 575 | 2-F—Ph | Prop | 4-SAc-Pipd |
| 576 | 2-F—Ph | Prop | 4-SProp-Pipd |
| 577 | 2-F—Ph | Prop | 4-SBur-Pipd |
| 578 | 2-F—Ph | Prop | 4-SPiv-Pipd |
| 579 | 2-F—Ph | Prop | 4-SHxn-Pipd |
| 580 | 2-F—Ph | Prop | 4-SPal-Pipd |
| 581 | 2-F—Ph | Prop | 4-SStl-Pipd |
| 582 | 2-F—Ph | Prop | 4-SOlo-Pipd |
| 583 | 2-F—Ph | Prop | 4-SCOPh-Pipd |
| 584 | 2-Cl—Ph | Prop | 4-SH-Pipd |
| 585 | 2-Cl—Ph | Prop | 4-SAc-Pipd |
| 586 | 2-Cl—Ph | Prop | 4-SProp-Pipd |
| 587 | 2-Cl—Ph | Prop | 4-SBur-Pipd |
| 588 | 2-Cl—Ph | Prop | 4-SPiv-Pipd |
| 589 | 2-F—Ph | c-PrCO | 4-SAc-Pipd |
| 590 | 2-F—Ph | c-PrCO | 4-SProp-Pipd |
| 591 | 2-F—Ph | c-PrCO | 4-SBur-Pipd |
| 592 | 2-F—Ph | c-PrCO | 4-(S-i-Bur)-Pipd |
| 593 | 2-F—Ph | c-PrCO | 4-SVal-Pipd |
| 594 | 2-F—Ph | c-PrCO | 4-SPiv-Pipd |
| 595 | 2-F—Ph | c-PrCO | 4-SHxn-Pipd |
| 596 | 2-F—Ph | c-PrCO | 4-SLau-Pipd |
| 597 | 2-F—Ph | c-PrCO | 4-SPal-Pipd |
| 598 | 2-F—Ph | c-PrCO | 4-S-Stl-Pipd |
| 599 | 2-F—Ph | c-PrCO | 4-SAcr-Pipd |
| 600 | 2-F—Ph | c-PrCO | 4-SOlo-Pipd |
| 601 | 2-F—Ph | c-PrCO | 4-SCOPh-Pipd |
| 602 | 2-Cl—Ph | c-PrCO | 4-SAc-Pipd |
| 603 | 2-Cl—Ph | c-PrCO | 4-SProp-Pipd |
| 604 | 2-Cl—Ph | c-PrCO | 4-SBur-Pipd |
| 605 | 2-Cl—Ph | c-PrCO | 4-(S-i-Bur)-Pipd |
| 606 | 2-Cl—Ph | c-PrCO | 4-SVal-Pipd |
| 607 | 2-Cl—Ph | c-PrCO | 4-SPiv-Pipd |
| 608 | 2-F—Ph | MeOCO | 4-SAc-Pipd |
| 609 | 2-F—Ph | MeOCO | 4-SProp-Pipd |
| 610 | 2-F—Ph | MeOCO | 4-SBur-Pipd |
| 611 | 2-F—Ph | MeOCO | 4-(S-i-Bur)-Pipd |
| 612 | 2-F—Ph | MeOCO | 4-SVal-Pipd |
| 613 | 2-F—Ph | MeOCO | 4-SPiv-Pipd |
| 614 | 2-F—Ph | MeOCO | 4-SHxn-Pipd |
| 615 | 2-F—Ph | MeOCO | 4-SLau-Pipd |
| 616 | 2-F—Ph | MeOCO | 4-SPal-Pipd |
| 617 | 2-F—Ph | MeOCO | 4-S-Stl-Pipd |
| 618 | 2-F—Ph | MeOCO | 4-SAcr-Pipd |
| 619 | 2-F—Ph | MeOCO | 4-SOlo-Pipd |
| 620 | 2-F—Ph | MeOCO | 4-SCOPh-Pipd |
| 621 | 2-Cl—Ph | MeOCO | 4-SAc-Pipd |
| 622 | 2-Cl—Ph | MeOCO | 4-SProp-Pipd |
| 623 | 2-Cl—Ph | MeOCO | 4-SBur-Pipd |
| 624 | 2-Cl—Ph | MeOCO | 4-(S-i-Bur)-Pipd |

TABLE 1-continued

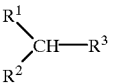
(I)

| Comp. No. | R¹ | R² | R³ |
|---|---|---|---|
| 625 | 2-Cl—Ph | MeOCO | 4-SVal-Pipd |
| 626 | 2-Cl—Ph | MeOCO | 4-SPiv-Pipd |
| 627 | 2-F—Ph | EtOCO | 4-SH-Pipd |
| 628 | 2-F—Ph | EtOCO | 4-SAc-Pipd |
| 629 | 2-F—Ph | EtOCO | 4-SProp-Pipd |
| 630 | 2-F—Ph | EtOCO | 4-SBur-Pipd |
| 631 | 2-F—Ph | EtOCO | 4-SPiv-Pipd |
| 632 | 2-F—Ph | EtOCO | 4-SHxn-Pipd |
| 633 | 2-F—Ph | EtOCO | 4-SPal-Pipd |
| 634 | 2-F—Ph | EtOCO | 4-SStl-Pipd |
| 635 | 2-Cl—Ph | EtOCO | 4-SH-Pipd |
| 636 | 2-Cl—Ph | EtOCO | 4-SAc-Pipd |
| 637 | 2-Cl—Ph | EtOCO | 4-SProp-Pipd |
| 638 | 2-Cl—Ph | EtOCO | 4-SBur-Pipd |
| 639 | 2-Cl—Ph | EtOCO | 4-SPiv-Pipd |
| 640 | 2-F—Ph | Ac | 4-CH₂SAc-Pipd |
| 641 | 2-F—Ph | Prop | 4-CH₂SH-Pipd |
| 642 | 2-F—Ph | Prop | 4-CH₂SAc-Pipd |
| 643 | 2-F—Ph | Prop | 4-CH₂SProp-Pipd |
| 644 | 2-F—Ph | Prop | 4-CH₂SBur-Pipd |
| 645 | 2-F—Ph | Prop | 4-CH₂SPiv-Pipd |
| 646 | 2-F—Ph | Prop | 4-CH₂SHxn-Pipd |
| 647 | 2-F—Ph | Prop | 4-CH₂SPal-Pipd |
| 648 | 2-F—Ph | Prop | 4-CH₂SStl-Pipd |
| 649 | 2-F—Ph | Prop | 4-CH₂SOlo-Pipd |
| 650 | 2-F—Ph | Prop | 4-CH₂SCOPh-Pipd |
| 651 | 2-Cl—Ph | Prop | 4-CH₂SH-Pipd |
| 652 | 2-Cl—Ph | Prop | 4-CH₂SAc-Pipd |
| 653 | 2-Cl—Ph | Prop | 4-CH₂Prop-Pipd |
| 654 | 2-Cl—Ph | Prop | 4-CH₂SBur-Pipd |
| 655 | 2-Cl—Ph | Prop | 4-CH₂SPiv-Pipd |
| 656 | 2-F—Ph | c-PrCO | 4-CH₂SAc-Pipd |
| 657 | 2-F—Ph | c-PrCO | 4-CH₂Prop-Pipd |
| 658 | 2-F—Ph | c-PrCO | 4-CH₂SBur-Pipd |
| 659 | 2-F—Ph | c-PrCO | 4-(CH₂S-i-Bur)-Pipd |
| 660 | 2-F—Ph | c-PrCO | 4-CH₂SVal-Pipd |
| 661 | 2-F—Ph | c-PrCO | 4-CH₂SPiv-Pipd |
| 662 | 2-F—Ph | c-PrCO | 4-CH₂SHxn-Pipd |
| 663 | 2-F—Ph | c-PrCO | 4-CH₂SLau-Pipd |
| 664 | 2-F—Ph | c-PrCO | 4-CH₂SPal-Pipd |
| 665 | 2-F—Ph | c-PrCO | 4-CH₂S-Stl-Pipd |
| 666 | 2-F—Ph | c-PrCO | 4-CH₂SAcr-Pipd |
| 667 | 2-F—Ph | c-PrCO | 4-CH₂SOlo-Pipd |
| 668 | 2-F—Ph | c-PrCO | 4-CH₂SCOPh-Pipd |
| 669 | 2-Cl—Ph | c-PrCO | 4-CH₂SAc-Pipd |
| 670 | 2-Cl—Ph | c-PrCO | 4-CH₂SProp-Pipd |
| 671 | 2-Cl—Ph | c-PrCO | 4-CH₂SBur-Pipd |
| 672 | 2-Cl—Ph | c-PrCO | 4-(CH₂S-i-Bur)-Pipd |
| 673 | 2-Cl—Ph | c-PrCO | 4-CH₂SVal-Pipd |
| 674 | 2-Cl—Ph | c-PrCO | 4-CH₂SPiv-Pipd |
| 675 | 2-F—Ph | MeOCO | 4-CH₂SAc-Pipd |
| 676 | 2-F—Ph | MeOCO | 4-CH₂SProp-Pipd |
| 677 | 2-F—Ph | MeOCO | 4-CH₂SBur-Pipd |
| 678 | 2-F—Ph | MeOCO | 4-(CH₂S-i-Bur)-Pipd |
| 679 | 2-F—Ph | MeOCO | 4-CH₂SVal-Pipd |
| 680 | 2-F—Ph | MeOCO | 4-CH₂SPiv-Pipd |
| 681 | 2-F—Ph | MeOCO | 4-CH₂SHxn-Pipd |
| 682 | 2-F—Ph | MeOCO | 4-CH₂SLau-Pipd |
| 683 | 2-F—Ph | MeOCO | 4-CH₂SPal-Pipd |
| 684 | 2-F—Ph | MeOCO | 4-CH₂S-Stl-Pipd |
| 685 | 2-F—Ph | MeOCO | 4-CH₂SAcr-Pipd |
| 686 | 2-F—Ph | MeOCO | 4-CH₂SOlo-Pipd |
| 687 | 2-F—Ph | MeOCO | 4-CH₂SCOPh-Pipd |
| 688 | 2-Cl—Ph | MeOCO | 4-CH₂SAc-Pipd |
| 689 | 2-Cl—Ph | MeOCO | 4-CH₂SProp-Pipd |
| 690 | 2-Cl—Ph | MeOCO | 4-CH₂SBur-Pipd |
| 691 | 2-Cl—Ph | MeOCO | 4-(CH₂S-i-Bur)-Pipd |
| 692 | 2-Cl—Ph | MeOCO | 4-CH₂SVal-Pipd |
| 693 | 2-Cl—Ph | MeOCO | 4-CH₂SPiv-Pipd |

TABLE 1-continued

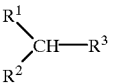

(I)

| Comp. No. | R¹ | R² | R³ |
|---|---|---|---|
| 694 | 2-F—Ph | EtOCO | 4-CH₂SH-Pipd |
| 695 | 2-F—Ph | EtOCO | 4-CH₂SAc-Pipd |
| 696 | 2-F—Ph | EtOCO | 4-CH₂SProp-Pipd |
| 697 | 2-F—Ph | EtOCO | 4-CH₂SBur-Pipd |
| 698 | 2-F—Ph | EtOCO | 4-CH₂SPiv-Pipd |
| 699 | 2-F—Ph | EtOCO | 4-CH₂SHxn-Pipd |
| 700 | 2-F—Ph | EtOCO | 4-CH₂SPal-Pipd |
| 701 | 2-F—Ph | EtOCO | 4-CH₂SStl-Pipd |
| 702 | 2-Cl—Ph | EtOCO | 4-CH₂SH-Pipd |
| 703 | 2-Cl—Ph | EtOCO | 4-CH₂SAc-Pipd |
| 704 | 2-Cl—Ph | EtOCO | 4-CH₂SProp-Pipd |
| 705 | 2-Cl—Ph | EtOCO | 4-CH₂SBur-Pipd |
| 706 | 2-Cl—Ph | EtOCO | 4-CH₂SPiv-Pipd |
| 707 | 2-F—Ph | Ac | 3-SAc-Pipd |
| 708 | 2-F—Ph | Prop | 3-SH-Pipd |
| 709 | 2-F—Ph | Prop | 3-SAc-Pipd |
| 710 | 2-F—Ph | Prop | 3-SProp-Pipd |
| 711 | 2-F—Ph | Prop | 3-SBur-Pipd |
| 712 | 2-F—Ph | Prop | 3-SPiv-Pipd |
| 713 | 2-Cl—Ph | Prop | 3-SH-Pipd |
| 714 | 2-Cl—Ph | Prop | 3-SAc-Pipd |
| 715 | 2-Cl—Ph | Prop | 3-SProp-Pipd |
| 716 | 2-F—Ph | c-PrCO | 3-SAc-Pipd |
| 717 | 2-F—Ph | c-PrCO | 3-SProp-Pipd |
| 718 | 2-F—Ph | c-PrCO | 3-SBur-Pipd |
| 719 | 2-F—Ph | c-PrCO | 3-(S-i-Bur)-Pipd |
| 720 | 2-F—Ph | c-PrCO | 3-SVal-Pipd |
| 721 | 2-F—Ph | c-PrCO | 3-SPiv-Pipd |
| 722 | 2-F—Ph | c-PrCO | 3-SCOPh-Pipd |
| 723 | 2-Cl—Ph | c-PrCO | 3-SAc-Pipd |
| 724 | 2-Cl—Ph | c-PrCO | 3-SProp-Pipd |
| 725 | 2-Cl—Ph | c-PrCO | 3-SBur-Pipd |
| 726 | 2-Cl—Ph | c-PrCO | 3-SVal-Pipd |
| 727 | 2-Cl—Ph | c-PrCO | 3-SPiv-Pipd |
| 728 | 2-F—Ph | MeOCO | 3-SAc-Pipd |
| 729 | 2-F—Ph | MeOCO | 3-SProp-Pipd |
| 730 | 2-F—Ph | MeOCO | 3-SBur-Pipd |
| 731 | 2-F—Ph | MeOCO | 3-(S-i-Bur)-Pipd |
| 732 | 2-F—Ph | MeOCO | 3-SVal-Pipd |
| 733 | 2-F—Ph | MeOCO | 3-SPiv-Pipd |
| 734 | 2-F—Ph | MeOCO | 3-SCOPh-Pipd |
| 735 | 2-Cl—Ph | MeOCO | 3-SAc-Pipd |
| 736 | 2-Cl—Ph | MeOCO | 3-SProp-Pipd |
| 737 | 2-Cl—Ph | MeOCO | 3-SBur-Pipd |
| 738 | 2-Cl—Ph | MeOCO | 3-SVal-Pipd |
| 739 | 2-Cl—Ph | MeOCO | 3-SPiv-Pipd |
| 740 | 2-F—Ph | EtOCO | 3-SH-Pipd |
| 741 | 2-F—Ph | EtOCO | 3-SAc-Pipd |
| 742 | 2-F—Ph | EtOCO | 3-SProp-Pipd |
| 743 | 2-F—Ph | EtOCO | 3-SBur-Pipd |
| 744 | 2-F—Ph | EtOCO | 3-SPiv-Pipd |
| 745 | 2-Cl—Ph | EtOCO | 3-SH-Pipd |
| 746 | 2-Cl—Ph | EtOCO | 3-SAc-Pipd |
| 747 | 2-Cl—Ph | EtOCO | 3-SProp-Pipd |
| 748 | 2-Cl—Ph | EtOCO | 3-SBur-Pipd |
| 749 | 2-Cl—Ph | EtOCO | 3-SPiv-Pipd |
| 750 | 2-F—Ph | Ac | 3-CH₂SAc-Pipd |
| 751 | 2-F—Ph | Prop | 3-CH₂SH-Pipd |
| 752 | 2-F—Ph | Prop | 3-CH₂SAc-Pipd |
| 753 | 2-F—Ph | Prop | 3-CH₂SProp-Pipd |
| 754 | 2-F—Ph | Prop | 3-CH₂SBur-Pipd |
| 755 | 2-F—Ph | Prop | 3-CH₂SPiv-Pipd |
| 756 | 2-Cl—Ph | Prop | 3-CH₂SH-Pipd |
| 757 | 2-Cl—Ph | Prop | 3-CH₂SAc-Pipd |
| 758 | 2-Cl—Ph | Prop | 3-CH₂SProp-Pipd |
| 759 | 2-Cl—Ph | Prop | 3-CH₂SBur-Pipd |
| 760 | 2-Cl—Ph | Prop | 3-CH₂SPiv-Pipd |
| 761 | 2-F—Ph | c-PrCO | 3-CH₂SAc-Pipd |
| 762 | 2-F—Ph | c-PrCO | 3-CH₂SProp-Pipd |

TABLE 1-continued

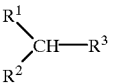
(I)

| Comp. No. | R[1] | R[2] | R[3] |
|---|---|---|---|
| 763 | 2-F—Ph | c-PrCO | 3-CH$_2$SBur-Pipd |
| 764 | 2-F—Ph | c-PrCO | 3-(CH$_2$S-i-Bur)-Pipd |
| 765 | 2-F—Ph | c-PrCO | 3-CH$_2$SVal-Pipd |
| 766 | 2-F—Ph | c-PrCO | 3-CH$_2$SPiv-Pipd |
| 767 | 2-F—Ph | c-PrCO | 3-CH$_2$SCOPh-Pipd |
| 768 | 2-Cl—Ph | c-PrCO | 3-CH$_2$SAc-Pipd |
| 769 | 2-Cl—Ph | c-PrCO | 3-CH$_2$SProp-Pipd |
| 770 | 2-Cl—Ph | c-PrCO | 3-CH$_2$SBur-Pipd |
| 771 | 2-Cl—Ph | c-PrCO | 3-CH$_2$SVal-Pipd |
| 772 | 2-Cl—Ph | c-PrCO | 3-CH$_2$SPiv-Pipd |
| 773 | 2-F—Ph | MeOCO | 3-CH$_2$SAc-Pipd |
| 774 | 2-F—Ph | MeOCO | 3-CH$_2$SProp-Pipd |
| 775 | 2-F—Ph | MeOCO | 3-CH$_2$SBur)-Pipd |
| 776 | 2-F—Ph | MeOCO | 3-(CH$_2$S-i-Bur)-Pipd |
| 777 | 2-F—Ph | MeOCO | 3-CH$_2$SVal-Pipd |
| 778 | 2-F—Ph | MeOCO | 3-CH$_2$SPiv-Pipd |
| 779 | 2-F—Ph | MeOCO | 3-CH$_2$SCOPh-Pipd |
| 780 | 2-Cl—Ph | MeOCO | 3-CH$_2$SAc-Pipd |
| 781 | 2-Cl—Ph | MeOCO | 3-CH$_2$SProp-Pipd |
| 782 | 2-Cl—Ph | MeOCO | 3-CH$_2$SBur-Pipd |
| 783 | 2-Cl—Ph | MeOCO | 3-CH$_2$SVal-Pipd |
| 784 | 2-Cl—Ph | MeOCO | 3-CH$_2$SPiv-Pipd |
| 785 | 2-F—Ph | EtOCO | 3-CH$_2$SH-Pipd |
| 786 | 2-F—Ph | EtOCO | 3-CH$_2$SAc-Pipd |
| 787 | 2-F—Ph | EtOCO | 3-CH$_2$SProp-Pipd |
| 788 | 2-F—Ph | EtOCO | 3-CH$_2$SBur-Pipd |
| 789 | 2-F—Ph | EtOCO | 3-CH$_2$SPiv-Pipd |
| 790 | 2-Cl—Ph | EtOCO | 3-CH$_2$SH-Pipd |
| 791 | 2-Cl—Ph | EtOCO | 3-CH$_2$SAc-Pipd |
| 792 | 2-Cl—Ph | EtOCO | 3-CH$_2$SProp-Pipd |
| 793 | 2-Cl—Ph | EtOCO | 3-CH$_2$SBur-Pipd |
| 794 | 2-Cl—Ph | EtOCO | 3-CH$_2$SPiv-Pipd |
| 795 | 2-F—Ph | Prop | 3-SH-Azed |
| 796 | 2-F—Ph | Prop | 3-SAc-Azed |
| 797 | 2-F—Ph | Prop | 3-SProp-Azed |
| 798 | 2-Cl—Ph | Prop | 3-SH-Azed |
| 799 | 2-Cl—Ph | Prop | 3-SAc-Azed |
| 800 | 2-F—Ph | c-PrCO | 3-SAc-Azed |
| 801 | 2-F—Ph | c-PrCO | 3-SProp-Azed |
| 802 | 2-Cl—Ph | c-PrCO | 3-SAc-Azed |
| 803 | 2-F—Ph | MeOCO | 3-SAc-Azed |
| 804 | 2-F—Ph | MeOCO | 3-SProp-Azed |
| 805 | 2-F—Ph | EtOCO | 3-SAc-Azed |
| 806 | 2-Cl—Ph | MeOCO | 3-SAc-Azed |
| 807 | 2-Cl—Ph | EtOCO | 3-SAc-Azed |
| 808 | 2-F—Ph | Prop | 3-CH$_2$SH-Azed |
| 809 | 2-F—Ph | Prop | 3-CH$_2$SAc-Azed |
| 810 | 2-F—Ph | Prop | 3-CH$_2$SPro-Azed |
| 811 | 2-Cl—Ph | Prop | 3-CH$_2$SH-Azed |
| 812 | 2-Cl—Ph | Prop | 3-CH$_2$SAc-Azed |
| 813 | 2-F—Ph | c-PrCO | 3-CH$_2$SAc-Azed |
| 814 | 2-F—Ph | c-PrCO | 3-CH$_2$SProp-Azed |
| 815 | 2-Cl—Ph | c-PrCO | 3-CH$_2$SAc-Azed |
| 816 | 2-F—Ph | MeOCO | 3-CH$_2$SAc-Azed |
| 817 | 2-F—Ph | MeOCO | 3-CH$_2$SProp-Azed |
| 818 | 2-F—Ph | EtOCO | 3-CH$_2$SAc-Azed |
| 819 | 2-Cl—Ph | MeOCO | 3-CH$_2$SAc-Azed |
| 820 | 2-Cl—Ph | EtOCO | 3-CH$_2$SAc-Azed |
| 821 | 2-F—Ph | Prop | 3-SH—ABOc |
| 822 | 2-F—Ph | Prop | 3-SAc-ABOc |
| 823 | 2-F—Ph | Prop | 3-SProp-ABOc |
| 824 | 2-Cl—Ph | Prop | 3-SH—ABOc |
| 825 | 2-Cl—Ph | Prop | 3-SAc-ABOc |
| 826 | 2-F—Ph | c-PrCO | 3-SAc-ABOc |
| 827 | 2-F—Ph | c-PrCO | 3-SProp-ABOc |
| 828 | 2-Cl—Ph | c-PrCO | 3-SAc-ABOc |
| 829 | 2-F—Ph | MeOCO | 3-SAc-ABOc |
| 830 | 2-F—Ph | MeOCO | 3-SProp-ABOc |
| 831 | 2-F—Ph | EtOCO | 3-SAc-ABOc |

TABLE 1-continued

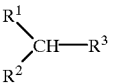

(I)

| Comp. No. | R¹ | R² | R³ |
|---|---|---|---|
| 832 | 2-Cl—Ph | MeOCO | 3-SAc-ABOc |
| 833 | 2-Cl—Ph | EtOCO | 3-SAc-ABOc |
| 834 | 2-F—Ph | Prop | 3-CH$_2$SH—ABOc |
| 835 | 2-F—Ph | Prop | 3-CH$_2$SAc-ABOc |
| 836 | 2-F—Ph | Prop | 3-CH$_2$SProp-ABOc |
| 837 | 2-Cl—Ph | Prop | 3-CH$_2$SH—ABOc |
| 838 | 2-Cl—Ph | Prop | 3-CH$_2$SAc-ABOc |
| 839 | 2-F—Ph | c-PrCO | 3-CH$_2$SAc-ABOc |
| 840 | 2-F—Ph | c-PrCO | 3-CH$_2$SProp-ABOc |
| 841 | 2-Cl—Ph | c-PrCO | 3-CH$_2$SAc-ABOc |
| 842 | 2-F—Ph | MeOCO | 3-CH$_2$SAc-ABOc |
| 843 | 2-F—Ph | MeOCO | 3-CH$_2$SProp-ABOc |
| 844 | 2-F—Ph | EtOCO | 3-CH$_2$SAc-ABOc |
| 845 | 2-Cl—Ph | MeOCO | 3-CH$_2$SAc-ABOc |
| 846 | 2-Cl—Ph | EtOCO | 3-CH$_2$SAc-ABOc |
| 847 | 2-F—Ph | Prop | 4-SAc-3-(=CH$_2$)Pipd |
| 848 | 2-F—Ph | Prop | 4-SProp-3-(=CH$_2$)Pipd |
| 849 | 2-F—Ph | Prop | 4-SBur-3-(=CH$_2$)Pipd |
| 850 | 2-F—Ph | Prop | 4-SVal-3-(=CH$_2$)Pipd |
| 851 | 2-F—Ph | Prop | 4-SPiv-3-(=CH$_2$)Pipd |
| 852 | 2-Cl—Ph | Prop | 4-SAc-3-(=CH$_2$)Pipd |
| 853 | 2-Cl—Ph | Prop | 4-SProp-3-(=CH$_2$)Pipd |
| 854 | 2-F—Ph | c-PrCO | 4-SAc-3-(=CH$_2$)Pipd |
| 855 | 2-F—Ph | c-PrCO | 4-SProp-3-(=CH$_2$)Pipd |
| 856 | 2-F—Ph | c-PrCO | 4-SBur-3-(=CH$_2$)Pipd |
| 857 | 2-F—Ph | c-PrCO | 4-S-i-Bur-3-(=CH$_2$)Pipd |
| 858 | 2-F—Ph | c-PrCO | 4-SVal-3-(=CH$_2$)Pipd |
| 859 | 2-F—Ph | c-PrCO | 4-SPiv-3-(=CH$_2$)Pipd |
| 860 | 2-Cl—Ph | c-PrCO | 4-SAc-3-(=CH$_2$)Pipd |
| 861 | 2-Cl—Ph | c-PrCO | 4-SProp-3-(=CH$_2$)Pipd |
| 862 | 2-Cl—Ph | c-PrCO | 4-SBur-3-(=CH$_2$)Pipd |
| 863 | 2-Cl—Ph | c-PrCO | 4-SVal-3-(=CH$_2$)Pipd |
| 864 | 2-Cl—Ph | c-PrCO | 4-SPiv-3-(=CH$_2$)Pipd |
| 865 | 2-F—Ph | MeOCO | 4-SAc-3-(=CH$_2$)Pipd |
| 866 | 2-F—Ph | MeOCO | 4-SProp-3-(=CH$_2$)Pipd |
| 867 | 2-F—Ph | MeOCO | 4-SBur-3-(=CH$_2$)Pipd |
| 868 | 2-F—Ph | MeOCO | 4-S-i-Bur-3-(=CH$_2$)Pipd |
| 869 | 2-F—Ph | MeOCO | 4-SVal-3-(=CH$_2$)Pipd |
| 870 | 2-F—Ph | MeOCO | 4-SPiv-3-(=CH$_2$)Pipd |
| 871 | 2-Cl—Ph | MeOCO | 4-SAc-3-(=CH$_2$)Pipd |
| 872 | 2-Cl—Ph | MeOCO | 4-SProp-3-(=CH$_2$)Pipd |
| 873 | 2-Cl—Ph | MeOCO | 4-SBur-3-(=CH$_2$)Pipd |
| 874 | 2-Cl—Ph | MeOCO | 4-SVal-3-(=CH$_2$)Pipd |
| 875 | 2-Cl—Ph | MeOCO | 4-SPiv-3-(=CH$_2$)Pipd |
| 876 | 2-F—Ph | EtOCO | 4-SAc-3-(=CH$_2$)Pipd |
| 877 | 2-F—Ph | EtOCO | 4-SProp-3-(=CH$_2$)Pipd |
| 878 | 2-F—Ph | EtOCO | 4-SBur-3-(=CH$_2$)Pipd |
| 879 | 2-F—Ph | EtOCO | 4-SVal-3-(=CH$_2$)Pipd |
| 880 | 2-F—Ph | EtOCO | 4-SPiv-3-(=CH$_2$)Pipd |
| 881 | 2-Cl—Ph | EtOCO | 4-SAc-3-(=CH$_2$)Pipd |
| 882 | 2-Cl—Ph | EtOCO | 4-SProp-3-(=CH$_2$)Pipd |
| 883 | 2-F—Ph | Prop | 4-SAc-3-(=CHMe)Pipd |
| 884 | 2-F—Ph | Prop | 4-SProp-3-(=CHMe)Pipd |
| 885 | 2-F—Ph | Prop | 4-SBur-3-(=CHMe)Pipd |
| 886 | 2-F—Ph | Prop | 4-SVal-3-(=CHMe)Pipd |
| 887 | 2-F—Ph | Prop | 4-SPiv-3-(=CHMe)Pipd |
| 888 | 2-Cl—Ph | Prop | 4-SAc-3-(=CHMe)Pipd |
| 889 | 2-Cl—Ph | Prop | 4-SProp-3-(=CHMe)Pipd |
| 890 | 2-F—Ph | c-PrCO | 4-SAc-3-(=CHMe)Pipd |
| 891 | 2-F—Ph | c-PrCO | 4-SProp-3-(=CHMe)Pipd |
| 892 | 2-F—Ph | c-PrCO | 4-SBur-3-(=CHMe)Pipd |
| 893 | 2-F—Ph | c-PrCO | 4-S-i-Bur-3-(=CHMe)Pipd |
| 894 | 2-F—Ph | c-PrCO | 4-SVal-3-(=CHMe)Pipd |
| 895 | 2-F—Ph | c-PrCO | 4-SPiv-3-(=CHMe)Pipd |
| 896 | 2-Cl—Ph | c-PrCO | 4-SAc-3-(=CHMe)Pipd |
| 897 | 2-Cl—Ph | c-PrCO | 4-SProp-3-(=CHMe)Pipd |
| 898 | 2-Cl—Ph | c-PrCO | 4-SBur-3-(=CHMe)Pipd |
| 899 | 2-Cl—Ph | c-PrCO | 4-SVal-3-(=CHMe)Pipd |
| 900 | 2-Cl—Ph | c-PrCO | 4-SPiv-3-(=CHMe)Pipd |

TABLE 1-continued

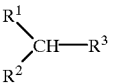
(I)

| Comp. No. | R¹ | R² | R³ |
|---|---|---|---|
| 901 | 2-F—Ph | MeOCO | 4-SAc-3-(═CHMe)Pipd |
| 902 | 2-F—Ph | MeOCO | 4-SProp-3-(═CHMe)Pipd |
| 903 | 2-F—Ph | MeOCO | 4-SBur-3-(═CHMe)Pipd |
| 904 | 2-F—Ph | MeOCO | 4-S-i-Bur-3-(═CHMe)Pipd |
| 905 | 2-F—Ph | MeOCO | 4-SVal-3-(═CHMe)Pipd |
| 906 | 2-F—Ph | MeOCO | 4-SPiv-3-(═CHMe)Pipd |
| 907 | 2-Cl—Ph | MeOCO | 4-SAc-3-(═CHMe)Pipd |
| 908 | 2-Cl—Ph | MeOCO | 4-SProp-3-(═CHMe)Pipd |
| 909 | 2-Cl—Ph | MeOCO | 4-SBur-3-(═CHMe)Pipd |
| 910 | 2-Cl—Ph | MeOCO | 4-SVal-3-(═CHMe)Pipd |
| 911 | 2-Cl—Ph | MeOCO | 4-SPiv-3-(═CHMe)Pipd |
| 912 | 2-F—Ph | EtOCO | 4-SAc-3-(═CHMe)Pipd |
| 913 | 2-F—Ph | EtOCO | 4-SProp-3-(═CHMe)Pipd |
| 914 | 2-F—Ph | EtOCO | 4-SBur-3-(═CHMe)Pipd |
| 915 | 2-F—Ph | EtOCO | 4-SVal-3-(═CHMe)Pipd |
| 916 | 2-F—Ph | EtOCO | 4-SPiv-3-(═CHMe)Pipd |
| 917 | 2-Cl—Ph | EtOCO | 4-SAc-3-(═CHMe)Pipd |
| 918 | 2-Cl—Ph | EtOCO | 4-SProp-3-(═CHMe)Pipd |
| 919 | 2-F—Ph | Prop | 4-SAc-3-(═CHEt)Pipd |
| 920 | 2-F—Ph | Prop | 4-SProp-3-(═CHEt)Pipd |
| 921 | 2-Cl—Ph | Prop | 4-SAc-3-(═CHEt)Pipd |
| 922 | 2-F—Ph | c-PrCO | 4-SAc-3-(═CHEt)Pipd |
| 923 | 2-F—Ph | c-PrCO | 4-SProp-3-(═CHEt)Pipd |
| 924 | 2-F—Ph | c-PrCO | 4-SBur-3-(═CHEt)Pipd |
| 925 | 2-F—Ph | c-PrCO | 4-S-i-Bur-3-(═CHEt)Pipd |
| 926 | 2-F—Ph | c-PrCO | 4-SVal-3-(═CHEt)Pipd |
| 927 | 2-F—Ph | c-PrCO | 4-SPiv-3-(═CHEt)Pipd |
| 928 | 2-Cl—Ph | c-PrCO | 4-SAc-3-(═CHEt)Pipd |
| 929 | 2-Cl—Ph | c-PrCO | 4-SProp-3-(═CHEt)Pipd |
| 930 | 2-F—Ph | MeOCO | 4-SAc-3-(═CHEt)Pipd |
| 931 | 2-F—Ph | MeOCO | 4-SProp-3-(═CHEt)Pipd |
| 932 | 2-F—Ph | MeOCO | 4-SBur-3-(═CHEt)Pipd |
| 933 | 2-F—Ph | MeOCO | 4-S-i-Bur-3-(═CHEt)Pipd |
| 934 | 2-F—Ph | MeOCO | 4-SVal-3-(═CHEt)Pipd |
| 935 | 2-F—Ph | MeOCO | 4-SPiv-3-(═CHEt)Pipd |
| 936 | 2-Cl—Ph | MeOCO | 4-SAc-3-(═CHEt)Pipd |
| 937 | 2-Cl—Ph | MeOCO | 4-SProp-3-(═CHEt)Pipd |
| 938 | 2-F—Ph | EtOCO | 4-SAc-3-(═CHEt)Pipd |
| 939 | 2-F—Ph | EtOCO | 4-SProp-3-(═CHEt)Pipd |
| 940 | 2-Cl—Ph | EtOCO | 4-SAc-3-(═CHEt)Pipd |
| 941 | 2-F—Ph | Prop | 4-SAc-3-(═CHPr)Pipd |
| 942 | 2-Cl—Ph | Prop | 4-SH-3-(═CHPr)Pipd |
| 943 | 2-Cl—Ph | Prop | 4-SAc-3-(═CHPr)Pipd |
| 944 | 2-F—Ph | c-PrCO | 4-SAc-3-(═CHPr)Pipd |
| 945 | 2-F—Ph | c-PrCO | 4-SProp-3-(═CHPr)Pipd |
| 946 | 2-F—Ph | c-PrCO | 4-SBur-3-(═CHPr)Pipd |
| 947 | 2-F—Ph | c-PrCO | 4-SVal-3-(═CHPr)Pipd |
| 948 | 2-F—Ph | c-PrCO | 4-SPiv-3-(═CHPr)Pipd |
| 949 | 2-Cl—Ph | c-PrCO | 4-SProp-3-(═CHPr)Pipd |
| 950 | 2-Cl—Ph | c-PrCO | 4-SAc-3-(═CHPr)Pipd |
| 951 | 2-F—Ph | MeOCO | 4-SAc-3-(═CHPr)Pipd |
| 952 | 2-F—Ph | MeOCO | 4-SProp-3-(CHPr-)Pipd |
| 953 | 2-F—Ph | MeOCO | 4-SBur-3-(═CHPr)Pipd |
| 954 | 2-F—Ph | MeOCO | 4-SVal-3-(═CHPr)Pipd |
| 955 | 2-F—Ph | MeOCO | 4-SPiv-3-(═CHPr)Pipd |
| 956 | 2-Cl—Ph | MeOCO | 4-SAc-3-(═CHPr)Pipd |
| 957 | 2-F—Ph | EtOCO | 4-SAc-3-(═CHPr)Pipd |
| 958 | 2-Cl—Ph | EtOCO | 4-SAc-3-(═CHPr)Pipd |
| 959 | 2-Cl—Ph | EtOCO | 4-SH-3-(═CHPr)Pipd |
| 960 | 2-F—Ph | Prop | 4-SAc-3-(═CHBu)Pipd |
| 961 | 2-Cl—Ph | Prop | 4-SH-3-(═CHBu)Pipd |
| 962 | 2-Cl—Ph | Prop | 4-SAc-3-(═CHBu)Pipd |
| 963 | 2-F—Ph | c-PrCO | 4-SAc-3-(═CHBu)Pipd |
| 964 | 2-F—Ph | c-PrCO | 4-SProp-3-(═CHBu)Pipd |
| 965 | 2-F—Ph | c-PrCO | 4-SBur-3-(═CHBu)Pipd |
| 966 | 2-F—Ph | c-PrCO | 4-SVal-3-(═CHBu)Pipd |
| 967 | 2-F—Ph | c-PrCO | 4-SPiv-3-(═CHBu)Pipd |
| 968 | 2-Cl—Ph | c-PrCO | 4-SProp-3-(═CHBu)Pipd |
| 969 | 2-Cl—Ph | c-PrCO | 4-SAc-3-(═CHBu)Pipd |

TABLE 1-continued

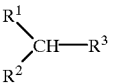
(I)

| Comp. No. | R¹ | R² | R³ |
|---|---|---|---|
| 970 | 2-F—Ph | MeOCO | 4-SAc-3-(=CHBu)Pipd |
| 971 | 2-F—Ph | MeOCO | 4-SProp-3-(=CHBu)Pipd |
| 972 | 2-F—Ph | MeOCO | 4-SBur-3-(=CHBu)Pipd |
| 973 | 2-F—Ph | MeOCO | 4-SVal-3-(=CHBu)Pipd |
| 974 | 2-F—Ph | MeOCO | 4-SPiv-3-(=CHBu)Pipd |
| 975 | 2-Cl—Ph | MeOCO | 4-SAc-3-(=CHBu)Pipd |
| 976 | 2-F—Ph | EtOCO | 4-SAc-3-(=CHBu)Pipd |
| 977 | 2-Cl—Ph | EtOCO | 4-SH-3-(=CHBu)Pipd |
| 978 | 2-Cl—Ph | EtOCO | 4-SAc-3-(=CHBu)Pipd |
| 979 | 2-F—Ph | Prop | 4-SAc-3-(=CHCO$_2$Me)Pipd |
| 980 | 2-F—Ph | Prop | 4-SProp-3-(=CHCO$_2$Me)Pipd |
| 981 | 2-F—Ph | Prop | 4-SBur-3-(=CHCO$_2$Me)Pipd |
| 982 | 2-F—Ph | Prop | 4-SVal-3-(=CHCO$_2$Me)Pipd |
| 983 | 2-F—Ph | Prop | 4-SPiv-3-(=CHCO$_2$Me)Pipd |
| 984 | 2-Cl—Ph | Prop | 4-SAc-3-(=CHCO$_2$Me)Pipd |
| 985 | 2-Cl—Ph | Prop | 4-SProp-3-(=CHCO$_2$Me)Pipd |
| 986 | 2-F—Ph | c-PrCO | 4-SAc-3-(=CHCO$_2$Me)Pipd |
| 987 | 2-F—Ph | c-PrCO | 4-SProp-3-(=CHCO$_2$Me)Pipd |
| 988 | 2-F—Ph | c-PrCO | 4-SBur-3-(=CHCO$_2$Me)Pipd |
| 989 | 2-F—Ph | c-PrCO | 4-S-i-Bur-3-(=CHCO$_2$Me)Pipd |
| 990 | 2-F—Ph | c-PrCO | 4-SVal-3-(=CHCO$_2$Me)Pipd |
| 991 | 2-F—Ph | c-PrCO | 4-SPiv-3-(=CHCO$_2$Me)Pipd |
| 992 | 2-Cl—Ph | c-PrCO | 4-SAc-3-(=CHCO$_2$Me)Pipd |
| 993 | 2-Cl—Ph | c-PrCO | 4-SProp-3-(=CHCO$_2$Me)Pipd |
| 994 | 2-Cl—Ph | c-PrCO | 4-SBur-3-(=CHCO$_2$Me)Pipd |
| 995 | 2-Cl—Ph | c-PrCO | 4-SVal-3-(=CHCO$_2$Me)Pipd |
| 996 | 2-Cl—Ph | c-PrCO | 4-SPiv-3-(=CHCO$_2$Me)Pipd |
| 997 | 2-F—Ph | MeOCO | 4-SAc-3-(=CHCO$_2$Me)Pipd |
| 998 | 2-F—Ph | MeOCO | 4-SProp-3-(=CHCO$_2$Me)Pipd |
| 999 | 2-F—Ph | MeOCO | 4-SBur-3-(=CHCO$_2$Me)Pipd |
| 1000 | 2-F—Ph | MeOCO | 4-S-i-Bur-3-(=CHCO$_2$Me)Pipd |
| 1001 | 2-F—Ph | MeOCO | 4-SVal-3-(=CHCO$_2$Me)Pipd |
| 1002 | 2-F—Ph | MeOCO | 4-SPiv-3-(=CHCO$_2$Me)Pipd |
| 1003 | 2-Cl—Ph | MeOCO | 4-SAc-3-(=CHCO$_2$Me)Pipd |
| 1004 | 2-Cl—Ph | MeOCO | 4-SProp-3-(=CHCO$_2$Me)Pipd |
| 1005 | 2-Cl—Ph | MeOCO | 4-SBur-3-(=CHCO$_2$Me)Pipd |
| 1006 | 2-Cl—Ph | MeOCO | 4-SVal-3-(=CHCO$_2$Me)Pipd |
| 1007 | 2-Cl—Ph | MeOCO | 4-SPiv-3-(=CHCO$_2$Me)Pipd |
| 1008 | 2-F—Ph | EtOCO | 4-SAc-3-(=CHCO$_2$Me)Pipd |
| 1009 | 2-F—Ph | EtOCO | 4-SProp-3-(=CHCO$_2$Me)Pipd |
| 1010 | 2-F—Ph | EtOCO | 4-SBur-3-(=CHCO$_2$Me)Pipd |
| 1011 | 2-F—Ph | EtOCO | 4-SVal-3-(=CHCO$_2$Me)Pipd |
| 1012 | 2-F—Ph | EtOCO | 4-SPiv-3-(=CHCO$_2$Me)Pipd |
| 1013 | 2-Cl—Ph | EtOCO | 4-SAc-3-(=CHCO$_2$Me)Pipd |
| 1014 | 2-Cl—Ph | EtOCO | 4-SProp-3-(=CHCO$_2$Me)Pipd |
| 1015 | 2-F—Ph | Prop | 4-SAc-3-(=CHCO$_2$Et)Pipd |
| 1016 | 2-F—Ph | Prop | 4-SProp-3-(=CHCO$_2$Et)Pipd |
| 1017 | 2-F—Ph | Prop | 4-SBur-3-(=CHCO$_2$Et)Pipd |
| 1018 | 2-F—Ph | Prop | 4-SVal-3-(=CHCO$_2$Et)Pipd |
| 1019 | 2-F—Ph | Prop | 4-SPiv-3-(=CHCO$_2$Et)Pipd |
| 1020 | 2-Cl—Ph | Prop | 4-SAc-3-(=CHCO$_2$Et)Pipd |
| 1021 | 2-Cl—Ph | Prop | 4-SProp-3-(=CHCO$_2$Et)Pipd |
| 1022 | 2-F—Ph | c-PrCO | 4-SAc-3-(=CHCO$_2$Et)Pipd |
| 1023 | 2-F—Ph | c-PrCO | 4-SProp-3-(=CHCO$_2$Et)Pipd |
| 1024 | 2-F—Ph | c-PrCO | 4-SBur-3-(=CHCO$_2$Et)Pipd |
| 1025 | 2-F—Ph | c-PrCO | 4-S-i-Bur-3-(=CHCO$_2$Et)Pipd |
| 1026 | 2-F—Ph | c-PrCO | 4-SVal-3-(=CHCO$_2$Et)Pipd |
| 1027 | 2-F—Ph | c-PrCO | 4-SPiv-3-(=CHCO$_2$Et)Pipd |
| 1028 | 2-Cl—Ph | c-PrCO | 4-SAc-3-(=CHCO$_2$Et)Pipd |
| 1029 | 2-Cl—Ph | c-PrCO | 4-SProp-3-(=CHCO$_2$Et)Pipd |
| 1030 | 2-Cl—Ph | c-PrCO | 4-SBur-3-(=CHCO$_2$Et)Pipd |
| 1031 | 2-Cl—Ph | c-PrCO | 4-SVal-3-(=CHCO$_2$Et)Pipd |
| 1032 | 2-Cl—Ph | c-PrCO | 4-SPiv-3-(=CHCO$_2$Et)Pipd |
| 1033 | 2-F—Ph | MeOCO | 4-SAc-3-(=CHCO$_2$Et)Pipd |
| 1034 | 2-F—Ph | MeOCO | 4-SProp-3-(=CHCO$_2$Et)Pipd |
| 1035 | 2-F—Ph | MeOCO | 4-SBur-3-(=CHCO$_2$Et)Pipd |
| 1036 | 2-F—Ph | MeOCO | 4-S-i-Bur-3-(=CHCO$_2$Et)Pipd |
| 1037 | 2-F—Ph | MeOCO | 4-SVal-3-(=CHCO$_2$Et)Pipd |
| 1038 | 2-F—Ph | MeOCO | 4-SPiv-3-(=CHCO$_2$Et)Pipd |

TABLE 1-continued $$\begin{array}{c} R^1 \\ \phantom{R^2}\diagdown \\ \phantom{R^2}CH-R^3 \\ R^2 \diagup \end{array} \qquad (I)$$

| Comp. No. | R¹ | R² | R³ |
|---|---|---|---|
| 1039 | 2-Cl—Ph | MeOCO | 4-SAc-3-(=CHCO₂Et)Pipd |
| 1040 | 2-Cl—Ph | MeOCO | 4-SProp-3-(=CHCO₂Et)Pipd |
| 1041 | 2-Cl—Ph | MeOCO | 4-SBur-3-(=CHCO₂Et)Pipd |
| 1042 | 2-Cl—Ph | MeOCO | 4-SVal-3-(=CHCO₂Et)Pipd |
| 1043 | 2-Cl—Ph | MeOCO | 4-SPiv-3-(=CHCO₂Et)Pipd |
| 1044 | 2-F—Ph | EtOCO | 4-SAc-3-(=CHCO₂Et)Pipd |
| 1045 | 2-F—Ph | EtOCO | 4-SProp-3-(=CHCO₂Et)Pipd |
| 1046 | 2-F—Ph | EtOCO | 4-SBur-3-(=CHCO₂Et)Pipd |
| 1047 | 2-F—Ph | EtOCO | 4-SVal-3-(=CHCO₂Et)Pipd |
| 1048 | 2-F—Ph | EtOCO | 4-SPiv-3-(=CHCO₂Et)Pipd |
| 1049 | 2-Cl—Ph | EtOCO | 4-SAc-3-(=CHCO₂Et)Pipd |
| 1050 | 2-Cl—Ph | EtOCO | 4-SProp-3-(=CHCO₂Et)Pipd |
| 1051 | 2-F—Ph | Prop | 4-SAc-3-(=CHCO₂Pr)Pipd |
| 1052 | 2-Cl—Ph | Prop | 4-SH-3-(=CHCO₂Pr)Pipd |
| 1053 | 2-Cl—Ph | Prop | 4-SAc-3-(=CHCO₂Pr)Pipd |
| 1054 | 2-F—Ph | c-PrCO | 4-SAc-3-(=CHCO₂Pr)Pipd |
| 1055 | 2-F—Ph | c-PrCO | 4-SProp-3-(=CHCO₂Pr)Pipd |
| 1056 | 2-F—Ph | c-PrCO | 4-SBur-3-(=CHCO₂Pr)Pipd |
| 1057 | 2-F—Ph | c-PrCO | 4-SVal-3-(=CHCO₂Pr)Pipd |
| 1058 | 2-F—Ph | c-PrCO | 4-SPiv-3-(=CHCO₂Pr)Pipd |
| 1059 | 2-Cl—Ph | c-PrCO | 4-SProp-3-(=CHCO₂Pr)Pipd |
| 1060 | 2-Cl—Ph | c-PrCO | 4-SAc-3-(=CHCO₂Pr)Pipd |
| 1061 | 2-F—Ph | MeOCO | 4-SAc-3-(=CHCO₂Pr)Pipd |
| 1062 | 2-F—Ph | MeOCO | 4-SProp-3-(=CHCO₂Pr)Pipd |
| 1063 | 2-F—Ph | MeOCO | 4-SBur-3-(=CHCO₂Pr)Pipd |
| 1064 | 2-F—Ph | MeOCO | 4-SVal-3-(=CHCO₂Pr)Pipd |
| 1065 | 2-F—Ph | MeOCO | 4-SPiv-3-(=CHCO₂Pr)Pipd |
| 1066 | 2-Cl—Ph | MeOCO | 4-SAc-3-(=CHCO₂Pr)Pipd |
| 1067 | 2-F—Ph | EtOCO | 4-SAc-3-(=CHCO₂Pr)Pipd |
| 1068 | 2-Cl—Ph | EtOCO | 4-SAc-3-(=CHCO₂Pr)Pipd |
| 1069 | 2-Cl—Ph | EtOCO | 4-SH-3-(=CHCO₂Pr)Pipd |
| 1070 | 2-F—Ph | Prop | 4-SAc-3-(=CHCO₂Bu)Pipd |
| 1071 | 2-Cl—Ph | Prop | 4-SH-3-(=CHCO₂Bu)Pipd |
| 1072 | 2-Cl—Ph | Prop | 4-SAc-3-(=CHCO₂Bu)Pipd |
| 1073 | 2-F—Ph | c-PrCO | 4-SAc-3-(=CHCO₂Bu)Pipd |
| 1074 | 2-F—Ph | c-PrCO | 4-SProp-3-(=CHCO₂Bu)Pipd |
| 1075 | 2-F—Ph | c-PrCO | 4-SBur-3-(=CHCO₂Bu)Pipd |
| 1076 | 2-F—Ph | c-PrCO | 4-SVal-3-(=CHCO₂Bu)Pipd |
| 1077 | 2-F—Ph | c-PrCO | 4-SPiv-3-(=CHCO₂Bu)Pipd |
| 1078 | 2-Cl—Ph | c-PrCO | 4-SProp-3-(=CHCO₂Bu)Pipd |
| 1079 | 2-Cl—Ph | c-PrCO | 4-SAc-3-(=CHCO₂Bu)Pipd |
| 1080 | 2-F—Ph | MeOCO | 4-SAc-3-(=CHCO₂Bu)Pipd |
| 1081 | 2-F—Ph | MeOCO | 4-SProp-3-(=CHCO₂Bu)Pipd |
| 1082 | 2-F—Ph | MeOCO | 4-SBur-3-(=CHCO₂Bu)Pipd |
| 1083 | 2-F—Ph | MeOCO | 4-SVal-3-(=CHCO₂Bu)Pipd |
| 1084 | 2-F—Ph | MeOCO | 4-SPiv-3-(=CHCO₂Bu)Pipd |
| 1085 | 2-Cl—Ph | MeOCO | 4-SAc-3-(=CHCO₂Bu)Pipd |
| 1086 | 2-F—Ph | EtOCO | 4-SAc-3-(=CHCO₂Bu)Pipd |
| 1087 | 2-Cl—Ph | EtOCO | 4-SH-3-(=CHCO₂Bu)Pipd |
| 1088 | 2-Cl—Ph | EtOCO | 4-SAc-3-(=CHCO₂Bu)Pipd |
| 1089 | 2-F—Ph | Prop | 4-SAc-3-(=CHCO₂H)Pipd |
| 1090 | 2-F—Ph | Prop | 4-SProp-3-(=CHCO₂H)Pipd |
| 1091 | 2-F—Ph | Prop | 4-SBur-3-(=CHCO₂H)Pipd |
| 1092 | 2-F—Ph | Prop | 4-SVal-3-(=CHCO₂H)Pipd |
| 1093 | 2-F—Ph | Prop | 4-SPiv-3-(=CHCO₂H)Pipd |
| 1094 | 2-Cl—Ph | Prop | 4-SAc-3-(=CHCO₂H)Pipd |
| 1095 | 2-Cl—Ph | Prop | 4-SProp-3-(=CHCO₂H)Pipd |
| 1096 | 2-F—Ph | c-PrCO | 4-SAc-3-(=CHCO₂H)Pipd |
| 1097 | 2-F—Ph | c-PrCO | 4-SProp-3-(=CHCO₂H)Pipd |
| 1098 | 2-F—Ph | c-PrCO | 4-SBur-3-(=CHCO₂H)Pipd |
| 1099 | 2-F—Ph | c-PrCO | 4-S-i-Bur-3-(=CHCO₂H)Pipd |
| 1100 | 2-F—Ph | c-PrCO | 4-SVal-3-(=CHCO₂H)Pipd |
| 1101 | 2-F—Ph | c-PrCO | 4-SPiv-3-(=CHCO₂H)Pipd |
| 1102 | 2-Cl—Ph | c-PrCO | 4-SAc-3-(=CHCO₂H)Pipd |
| 1103 | 2-Cl—Ph | c-PrCO | 4-SProp-3-(=CHCO₂H)Pipd |
| 1104 | 2-Cl—Ph | c-PrCO | 4-SBur-3-(=CHCO₂H)Pipd |
| 1105 | 2-Cl—Ph | c-PrCO | 4-SVal-3-(=CHCO₂H)Pipd |
| 1106 | 2-Cl—Ph | c-PrCO | 4-SPiv-3-(=CHCO₂H)Pipd |
| 1107 | 2-F—Ph | MeOCO | 4-SAc-3-(=CHCO₂H)Pipd |

TABLE 1-continued

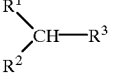

(I)

| Comp. No. | $R^1$ | $R^2$ | $R^3$ |
|---|---|---|---|
| 1108 | 2-F—Ph | MeOCO | 4-SProp-3-(=CHCO$_2$H)Pipd |
| 1109 | 2-F—Ph | MeOCO | 4-SBur-3-(=CHCO$_2$H)Pipd |
| 1110 | 2-F—Ph | MeOCO | 4-S-i-Bur-3-(=CHCO$_2$H)Pipd |
| 1111 | 2-F—Ph | MeOCO | 4-SVal-3-(=CHCO$_2$H)Pipd |
| 1112 | 2-F—Ph | MeOCO | 4-SPiv-3-(=CHCO$_2$H)Pipd |
| 1113 | 2-Cl—Ph | MeOCO | 4-SAc-3-(=CHCO$_2$H)Pipd |
| 1114 | 2-Cl—Ph | MeOCO | 4-SProp-3-(=CHCO$_2$H)Pipd |
| 1115 | 2-Cl—Ph | MeOCO | 4-SBur-3-(=CHCO$_2$H)Pipd |
| 1116 | 2-Cl—Ph | MeOCO | 4-SVal-3-(=CHCO$_2$H)Pipd |
| 1117 | 2-Cl—Ph | MeOCO | 4-SPiv-3-(=CHCO$_2$H)Pipd |
| 1118 | 2-F—Ph | EtOCO | 4-SAc-3-(=CHCO$_2$H)Pipd |
| 1119 | 2-F—Ph | EtOCO | 4-SProp-3-(=CHCO$_2$H)Pipd |
| 1120 | 2-F—Ph | EtOCO | 4-SBur-3-(=CHCO$_2$H)Pipd |
| 1121 | 2-F—Ph | EtOCO | 4-SVal-3-(=CHCO$_2$H)Pipd |
| 1122 | 2-F—Ph | EtOCO | 4-SPiv-3-(=CHCO$_2$H)Pipd |
| 1123 | 2-Cl—Ph | EtOCO | 4-SAc-3-(=CHCO$_2$H)Pipd |
| 1124 | 2-Cl—Ph | EtOCO | 4-SProp-3-(=CHCO$_2$H)Pipd |
| 1125 | 2-F—Ph | Prop | 4-SAc-3-(=CHCONMe$_2$)Pipd |
| 1126 | 2-F—Ph | Prop | 4-SProp-3-(=CHCONMe$_2$)Pipd |
| 1127 | 2-F—Ph | Prop | 4-SBur-3-(=CHCONMe$_2$)Pipd |
| 1128 | 2-F—Ph | Prop | 4-SVal-3-(=CHCONMe$_2$)Pipd |
| 1129 | 2-F—Ph | Prop | 4-SPiv-3-(=CHCONMe$_2$)Pipd |
| 1130 | 2-Cl—Ph | Prop | 4-SAc-3-(=CHCONMe$_2$)Pipd |
| 1131 | 2-Cl—Ph | Prop | 4-SProp-3-(=CHCONMe$_2$)Pipd |
| 1132 | 2-F—Ph | c-PrCO | 4-SAc-3-(=CHCONMe$_2$)Pipd |
| 1133 | 2-F—Ph | c-PrCO | 4-SProp-3-(=CHCONMe$_2$)Pipd |
| 1134 | 2-F—Ph | c-PrCO | 4-SBur-3-(=CHCONMe$_2$)Pipd |
| 1135 | 2-F—Ph | c-PrCO | 4-S-i-Bur-3-(=CHCONMe$_2$)Pipd |
| 1136 | 2-F—Ph | c-PrCO | 4-SVal-3-(=CHCONMe$_2$)Pipd |
| 1137 | 2-F—Ph | c-PrCO | 4-SPiv-3-(=CHCONMe$_2$)Pipd |
| 1138 | 2-Cl—Ph | c-PrCO | 4-SAc-3-(=CHCONMe$_2$)Pipd |
| 1139 | 2-Cl—Ph | c-PrCO | 4-SProp-3-(=CHCONMe$_2$)Pipd |
| 1140 | 2-Cl—Ph | c-PrCO | 4-SBur-3-(=CHCONMe$_2$)Pipd |
| 1141 | 2-Cl—Ph | c-PrCO | 4-SVal-3-(=CHCONMe$_2$)Pipd |
| 1142 | 2-Cl—Ph | c-PrCO | 4-SPiv-3-(=CHCONMe$_2$)Pipd |
| 1143 | 2-F—Ph | MeOCO | 4-SAc-3-(=CHCONMe$_2$)Pipd |
| 1144 | 2-F—Ph | MeOCO | 4-SProp-3-(=CHCONMe$_2$)Pipd |
| 1145 | 2-F—Ph | MeOCO | 4-SBur-3-(=CHCONMe$_2$)Pipd |
| 1146 | 2-F—Ph | MeOCO | 4-S-i-Bur-3-(=CHCONMe$_2$)Pipd |
| 1147 | 2-F—Ph | MeOCO | 4-SVal-3-(=CHCONMe$_2$)Pipd |
| 1148 | 2-F—Ph | MeOCO | 4-SPiv-3-(=CHCONMe$_2$)Pipd |
| 1149 | 2-Cl—Ph | MeOCO | 4-SAc-3-(=CHCONMe$_2$)Pipd |
| 1150 | 2-Cl—Ph | MeOCO | 4-SProp-3-(=CHCONMe$_2$)Pipd |
| 1151 | 2-Cl—Ph | MeOCO | 4-SBur-3-(=CHCONMe$_2$)Pipd |
| 1152 | 2-Cl—Ph | MeOCO | 4-SVal-3-(=CHCONMe$_2$)Pipd |
| 1153 | 2-Cl—Ph | MeOCO | 4-SPiv-3-(=CHCONMe$_2$)Pipd |
| 1154 | 2-F—Ph | EtOCO | 4-SAc-3-(=CHCONMe$_2$)Pipd |
| 1155 | 2-F—Ph | EtOCO | 4-SProp-3-(=CHCONMe$_2$)Pipd |
| 1156 | 2-F—Ph | EtOCO | 4-SBur-3-(=CHCONMe$_2$)Pipd |
| 1157 | 2-F—Ph | EtOCO | 4-SVal-3-(=CHCONMe$_2$)Pipd |
| 1158 | 2-F—Ph | EtOCO | 4-SPiv-3-(=CHCONMe$_2$)Pipd |
| 1159 | 2-Cl—Ph | EtOCO | 4-SAc-3-(=CHCONMe$_2$)Pipd |
| 1160 | 2-Cl—Ph | EtOCO | 4-SProp-3-(=CHCONMe$_2$)Pipd |
| 1161 | 2-F—Ph | Prop | 4-SAc-3-(=CHCONHMe)Pipd |
| 1162 | 2-F—Ph | Prop | 4-SProp-3-(=CHCOHNMe)Pipd |
| 1163 | 2-F—Ph | Prop | 4-SBur-3-(=CHCONHMe)Pipd |
| 1164 | 2-F—Ph | Prop | 4-SVal-3-(=CHCONHMe)Pipd |
| 1165 | 2-F—Ph | Prop | 4-SPiv-3-(=CHCONHMe)Pipd |
| 1166 | 2-Cl—Ph | Prop | 4-SAc-3-(=CHCONHMe)Pipd |
| 1167 | 2-Cl—Ph | Prop | 4-SProp-3-(=CHCONHMe)Pipd |
| 1168 | 2-F—Ph | c-PrCO | 4-SAc-3-(=CHCONHMe)Pipd |
| 1169 | 2-F—Ph | c-PrCO | 4-SProp-3-(=CHCONHMe)Pipd |
| 1170 | 2-F—Ph | c-PrCO | 4-SBur-3-(=CHCONHMe)Pipd |
| 1171 | 2-F—Ph | c-PrCO | 4-S-i-Bur-3-(=CHCONHMe)Pipd |
| 1172 | 2-F—Ph | c-PrCO | 4-SVal-3-(=CHCONHMe)Pipd |
| 1173 | 2-F—Ph | c-PrCO | 4-SPiv-3-(=CHCONHMe)Pipd |
| 1174 | 2-Cl—Ph | c-PrCO | 4-SAc-3-(=CHCONHMe)Hpipd |
| 1175 | 2-Cl—Ph | c-PrCO | 4-SProp-3-(=CHCONHMe)Pipd |
| 1176 | 2-Cl—Ph | c-PrCO | 4-SBur-3-(=CHCONHMe)Pipd |

TABLE 1-continued

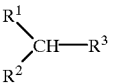

(I)

| Comp. No. | R¹ | R² | R³ |
| --- | --- | --- | --- |
| 1177 | 2-Cl—Ph | c-PrCO | 4-SVal-3-(=CHCONHMe)Pipd |
| 1178 | 2-Cl—Ph | c-PrCO | 4-SPiv-3-(=CHCONHMe)Pipd |
| 1179 | 2-F—Ph | MeOCO | 4-SAc-3-(=CHCONHMe)Pipd |
| 1180 | 2-F—Ph | MeOCO | 4-SProp-3-(=CHCONHMe)Pipd |
| 1181 | 2-F—Ph | MeOCO | 4-SBur-3-(=CHCONHMe)Pipd |
| 1182 | 2-F—Ph | MeOCO | 4-S-i-Bur-3-(=CHCONHMe)Pipd |
| 1183 | 2-F—Ph | MeOCO | 4-SVal-3-(=CHCONHMe)Pipd |
| 1184 | 2-F—Ph | MeOCO | 4-SPiv-3-(=CHCONHMe)Pipd |
| 1185 | 2-Cl—Ph | MeOCO | 4-SAc-3-(=CHCONHMe)Pipd |
| 1186 | 2-Cl—Ph | MeOCO | 4-SProp-3-(=CHCONHMe)Pipd |
| 1187 | 2-Cl—Ph | MeOCO | 4-SBur-3-(=CHCONHMe)Pipd |
| 1188 | 2-Cl—Ph | MeOCO | 4-SVal-3-(=CHCONHMe)Pipd |
| 1189 | 2-Cl—Ph | MeOCO | 4-SPiv-3-(=CHCONHMe)Pipd |
| 1190 | 2-F—Ph | EtOCO | 4-SAc-3-(=CHCONHMe)Pipd |
| 1191 | 2-F—Ph | EtOCO | 4-SProp-3-(=CHCONHMe)Pipd |
| 1192 | 2-F—Ph | EtOCO | 4-SBur-3-(=CHCONHMe)Pipd |
| 1193 | 2-F—Ph | EtOCO | 4-SVal-3-(=CHCONHMe)Pipd |
| 1194 | 2-F—Ph | EtOCO | 4-SPiv-3-(=CHCONHMe)Pipd |
| 1195 | 2-Cl—Ph | EtOCO | 4-SAc-3-(=CHCONHMe)Pipd |
| 1196 | 2-Cl—Ph | EtOCO | 4-SProp-3-(=CHCONHMe)Pipd |
| 1197 | 2-F—Ph | Prop | 4-SAc-3-(=CHCONH₂)Pipd |
| 1198 | 2-Cl—Ph | Prop | 4-SH-3-(=CHCONH₂)Pipd |
| 1199 | 2-Cl—Ph | Prop | 4-SAc-3-(=CHCONH₂)Pipd |
| 1200 | 2-F—Ph | c-PrCO | 4-SAc-3-(=CHCONH₂)Pipd |
| 1201 | 2-F—Ph | c-PrCO | 4-SProp-3-(=CHCONH₂)Pipd |
| 1202 | 2-F—Ph | c-PrCO | 4-SBur-3-(=CHCONH₂)Pipd |
| 1203 | 2-F—Ph | c-PrCO | 4-SVal-3-(=CHCONH₂)Pipd |
| 1204 | 2-F—Ph | c-PrCO | 4-SPiv-3-(=CHCONH₂)Pipd |
| 1205 | 2-Cl—Ph | c-PrCO | 4-SProp-3-(=CHCONH₂)Pipd |
| 1206 | 2-Cl—Ph | c-PrCO | 4-SAc-3-(=CHCONH₂)Pipd |
| 1207 | 2-F—Ph | MeOCO | 4-SAc-3-(=CHCONH₂)Pipd |
| 1208 | 2-F—Ph | MeOCO | 4-SProp-3-(=CHCONH₂)Pipd |
| 1209 | 2-F—Ph | MeOCO | 4-SBur-3-(=CHCONH₂)Pipd |
| 1210 | 2-F—Ph | MeOCO | 4-SVal-3-(=CHCONH₂)Pipd |
| 1211 | 2-F—Ph | MeOCO | 4-SPiv-3-(=CHCONH₂)Pipd |
| 1212 | 2-Cl—Ph | MeOCO | 4-SAc-3-(=CHCONH₂)Pipd |
| 1213 | 2-F—Ph | EtOCO | 4-SAc-3-(=CHCONH₂)Pipd |
| 1214 | 2-Cl—Ph | EtOCO | 4-SH-3-(=CHCONH₂)Pipd |
| 1215 | 2-Cl—Ph | EtOCO | 4-SAc-3-(=CHCONH₂)Pipd |
| 1216 | 2-F—Ph | Prop | 4-SAc-3-(=CHCONHEt)Pipd |
| 1217 | 2-Cl—Ph | Prop | 4-SH-3-(=CHCONHEt)Pipd |
| 1218 | 2-Cl—Ph | Prop | 4-SAc-3-(=CHCONHEt)Pipd |
| 1219 | 2-F—Ph | c-PrCO | 4-SAc-3-(=CHCONHEt)Pipd |
| 1220 | 2-F—Ph | c-PrCO | 4-SProp-3-(=CHCONHEt)Pipd |
| 1221 | 2-F—Ph | c-PrCO | 4-SBur-3-(=CHCONHEt)Pipd |
| 1222 | 2-F—Ph | c-PrCO | 4-SVal-3-(=CHCONHEt)Pipd |
| 1223 | 2-F—Ph | c-PrCO | 4-SPiv-3-(=CHCONHEt)Pipd |
| 1224 | 2-Cl—Ph | c-PrCO | 4-SProp-3-(=CHCONHEt)Pipd |
| 1225 | 2-Cl—Ph | c-PrCO | 4-SAc-3-(=CHCONHEt)Pipd |
| 1226 | 2-F—Ph | MeOCO | 4-SAc-3-(=CHCONHEt)Pipd |
| 1227 | 2-F—Ph | MeOCO | 4-SProp-3-(=CHCONHEt)Pipd |
| 1228 | 2-F—Ph | MeOCO | 4-SBur-3-(=CHCONHEt)Pipd |
| 1229 | 2-F—Ph | MeOCO | 4-SVal-3-(=CHCONHEt)Pipd |
| 1230 | 2-F—Ph | MeOCO | 4-SPiv-3-(=CHCONHEt)Pipd |
| 1231 | 2-Cl—Ph | MeOCO | 4-SAc-3-(=CHCONHEt)Pipd |
| 1232 | 2-F—Ph | EtOCO | 4-SAc-3-(=CHCONHEt)Pipd |
| 1233 | 2-Cl—Ph | EtOCO | 4-SH-3-(=CHCONHEt)Pipd |
| 1234 | 2-Cl—Ph | EtOCO | 4-SAc-3-(=CHCONHEt)Pipd |
| 1235 | 2-F—Ph | c-PrCO | 4-SCO₂Me-Pipd |
| 1236 | 2-F—Ph | c-PrCO | 4-SCO₂Et-Pipd |
| 1237 | 2-F—Ph | c-PrCO | 4-SCO₂Pr-Pipd |
| 1238 | 2-F—Ph | c-PrCO | 4-SCO₂-i-Pr-Pipd |
| 1239 | 2-F—Ph | c-PrCO | 4-SCO₂Bu-Pipd |
| 1240 | 2-F—Ph | c-PrCO | 4-SCO₂-i-Bu-Pipd |
| 1241 | 2-Cl—Ph | c-PrCO | 4-SCO₂Me-Pipd |
| 1242 | 2-Cl—Ph | c-PrCO | 4-SCO₂Et-Pipd |
| 1243 | 2-Cl—Ph | c-PrCO | 4-SCO₂Pr-Pipd |
| 1244 | 2-Cl—Ph | c-PrCO | 4-SCO₂-i-Pr-Pipd |
| 1245 | 2-Cl—Ph | c-PrCO | 4-SCO₂Bu-Pipd |

TABLE 1-continued

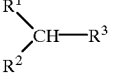

| Comp. No. | $R^1$ | $R^2$ | $R^3$ |
|---|---|---|---|
| 1246 | 2-Cl—Ph | c-PrCO | 4-SCO$_2$-i-Bu-Pipd |
| 1247 | 2-F—Ph | MeOCO | 4-SCO$_2$Me-Pipd |
| 1248 | 2-F—Ph | MeOCO | 4-SCO$_2$Et-Pipd |
| 1249 | 2-Cl—Ph | MeOCO | 4-SCO$_2$Me-Pipd |
| 1250 | 2-Cl—Ph | MeOCO | 4-SCO$_2$Et-Pipd |
| 1251 | 2-F—Ph | Prop | 4-SCO$_2$Me-Pipd |
| 1252 | 2-F—Ph | Prop | 4-SCO$_2$Et-Pipd |
| 1253 | 2-Cl—Ph | Prop | 4-SCO$_2$Me-Pipd |
| 1254 | 2-Cl—Ph | Prop | 4-SCO$_2$Et-Pipd |
| 1255 | 2-F—Ph | c-PrCO | 3-SCO$_2$Me-Azed |
| 1256 | 2-F—Ph | c-PrCO | 3-SCO$_2$Et-Azed |
| 1257 | 2-Cl—Ph | c-PrCO | 3-SCO$_2$Me-Azed |
| 1258 | 2-Cl—Ph | c-PrCO | 3-SCO$_2$Et-Azed |
| 1259 | 2-F—Ph | MeOCO | 3-SCO$_2$Me-Azed |
| 1260 | 2-F—Ph | MeOCO | 3-SCO$_2$Et-Azed |
| 1261 | 2-Cl—Ph | MeOCO | 3-SCO$_2$Me-Azed |
| 1262 | 2-Cl—Ph | MeOCO | 3-SCO$_2$Et-Azed |
| 1263 | 2-F—Ph | c-PrCO | 3-CH$_2$SCO$_2$Et-Azed |
| 1264 | 2-Cl—Ph | c-PrCO | 3-CH$_2$SCO$_2$Et-Azed |
| 1265 | 2-F—Ph | MeOCO | 3-CH$_2$SCO$_2$Et-Azed |
| 1266 | 2-Cl—Ph | MeOCO | 3-CH$_2$SCO$_2$Et-Azed |
| 1267 | 2-F—Ph | c-PrCO | 3-SCO$_2$Et-Pyrd |
| 1268 | 2-Cl—Ph | c-PrCO | 3-SCO$_2$Et-Pyrd |
| 1269 | 2-F—Ph | MeOCO | 3-SCO$_2$Et-Pyrd |
| 1270 | 2-Cl—Ph | MeOCO | 3-SCO$_2$Et-Pyrd |
| 1271 | 2-F—Ph | c-PrCO | 3-SCO$_2$Et-Pipd |
| 1272 | 2-Cl—Ph | c-PrCO | 3-SCO$_2$Et-Pipd |
| 1273 | 2-F—Ph | MeOCO | 3-SCO$_2$Et-Pipd |
| 1274 | 2-Cl—Ph | MeOCO | 3-SCO$_2$Et-Pipd |
| 1275 | 2-F—Ph | c-PrCO | 4-CH$_2$SCO$_2$Et-Pipd |
| 1276 | 2-Cl—Ph | c-PrCO | 4-CH$_2$SCO$_2$Et-Pipd |
| 1277 | 2-F—Ph | MeOCO | 4-CH$_2$SCO$_2$Et-Pipd |
| 1278 | 2-Cl—Ph | MeOCO | 4-CH$_2$SCO$_2$Et-Pipd |
| 1279 | 2-F—Ph | c-PrCO | 4-SCO$_2$Et-ABOc |
| 1280 | 2-Cl—Ph | c-PrCO | 4-SCO$_2$Et-ABOc |
| 1281 | 2-F—Ph | MeOCO | 4-SCO$_2$Et-ABOc |
| 1282 | 2-Cl—Ph | MeOCO | 4-SCO$_2$Et-ABOc |
| 1283 | 2-F—Ph | c-PrCO | 4-CH$_2$SCO$_2$Et-ABOc |
| 1284 | 2-Cl—Ph | c-PrCO | 4-CH$_2$SCO$_2$Et-ABOc |
| 1285 | 2-F—Ph | c-PrCO | 4-SCO$_2$Et-3-(=CHMe)Pipd |
| 1286 | 2-Cl—Ph | c-PrCO | 4-SCO$_2$Et-3-(=CHMe)Pipd |
| 1287 | 2-F—Ph | MeOCO | 4-SCO$_2$Et-3-(=CHMe)Pipd |
| 1288 | 2-Cl—Ph | MeOCO | 4-SCO$_2$Et-3-(=CHMe)Pipd |
| 1289 | 2-F—Ph | c-PrCO | 4-SCO$_2$Et-3-(=CHEt)Pipd |
| 1290 | 2-Cl—Ph | c-PrCO | 4-SCO$_2$Et-3-(=CHPr)Pipd |
| 1291 | 2-F—Ph | c-PrCO | 4-SCO$_2$Me-3-(=CHCO$_2$Me)Pipd |
| 1292 | 2-Cl—Ph | c-PrCO | 4-SCO$_2$Me-3-(=CHCO$_2$Me)Pipd |
| 1293 | 2-F—Ph | MeOCO | 4-SCO$_2$Et-3-(=CHCO$_2$Me)Pipd |
| 1294 | 2-Cl—Ph | MeOCO | 4-SCO$_2$Et-3-(=CHCO$_2$Me)Pipd |
| 1295 | 2-F—Ph | c-PrCO | 4-SCO$_2$Me-3-(=CHCO$_2$Et)Pipd |
| 1296 | 2-F—Ph | c-PrCO | 4-SCO$_2$Et-3-(=CHCO$_2$Et)Pipd |
| 1297 | 2-F—Ph | c-PrCO | 4-SCO$_2$Pr-3-(=CHCO$_2$Et)Pipd |
| 1298 | 2-F—Ph | c-PrCO | 4-SCO$_2$Bu-3-(=CHCO$_2$Et)Pipd |
| 1299 | 2-Cl—Ph | c-PrCO | 4-SCO$_2$Me-3-(=CHCO$_2$Et)Pipd |
| 1300 | 2-Cl—Ph | c-PrCO | 4-SCO$_2$Et-3-(=CHCO$_2$Et)Pipd |
| 1301 | 2-F—Ph | MeOCO | 4-SCO$_2$Me-3-(=CHCO$_2$Et)Pipd |
| 1302 | 2-F—Ph | MeOCO | 4-SCO$_2$Et-3-(=CHCO$_2$Et)Pipd |
| 1303 | 2-Cl—Ph | MeOCO | 4-SCO$_2$Me-3-(=CHCO$_2$Et)Pipd |
| 1304 | 2-Cl—Ph | MeOCO | 4-SCO$_2$Et-3-(=CHCO$_2$Et)Pipd |
| 1305 | 2-F—Ph | c-PrCO | 4-SCO$_2$Et-3-(=CHCO$_2$Pr)Pipd |
| 1306 | 2-F—Ph | c-PrCO | 4-SCO$_2$Et-3-(=CHCO$_2$Bu)Pipd |
| 1307 | 2-F—Ph | c-PrCO | 4-SCO$_2$Me-3-(=CHCO$_2$H)Pipd |
| 1308 | 2-F—Ph | c-PrCO | 4-SCO$_2$Et-3-(=CHCO$_2$H)Pipd |
| 1309 | 2-Cl—Ph | c-PrCO | 4-SCO$_2$Et-3-(=CHCO$_2$H)Pipd |
| 1310 | 2-F—Ph | MeOCO | 4-SCO$_2$Et-3-(=CHCO$_2$H)Pipd |
| 1311 | 2-Cl—Ph | MeOCO | 4-SCO$_2$Et-3-(=CHCO$_2$H)Pipd |
| 1312 | 2-F—Ph | c-PrCO | 4-SCO$_2$Et-3-(=CHCONMe$_2$)Pipd |
| 1313 | 2-Cl—Ph | c-PrCO | 4-SCO$_2$Et-3-(=CHCONMe$_2$)Pipd |
| 1314 | 2-F—Ph | MeOCO | 4-SCO$_2$Et-3-(=CHCONMe$_2$)Pipd |

TABLE 1-continued $$\underset{R^2}{\overset{R^1}{\diagdown}}CH-R^3 \quad (I)$$

| Comp. No. | $R^1$ | $R^2$ | $R^3$ |
|---|---|---|---|
| 1315 | 2-Cl—Ph | MeOCO | 4-SCO$_2$Et-3-(=CHCONMe$_2$)Pipd |
| 1316 | 2-F—Ph | c-PrCO | 4-SCO$_2$Et-3-(=CHCONHMe)Pipd |
| 1317 | 2-Cl—Ph | c-PrCO | 4-SCO$_2$Et-3-(=CHCONHMe)Pipd |
| 1318 | 2-F—Ph | MeOCO | 4-SCO$_2$Et-3-(=CHCONHMe)Pipd |
| 1319 | 2-F—Ph | c-PrCO | 4-SCO$_2$Et-3-(=CHCONHEt)Pipd |
| 1320 | 2-F—Ph | MeOCO | 4-SCO$_2$Et-3-(=CHCONHEt)Pipd |
| 1321 | 2-Cl—Ph | c-PrCO | 4-SCO$_2$Et-3-(=CHCONHEt)Pipd |
| 1322 | 2-F—Ph | c-PrCO | 4-SCO$_2$Et-3-(=CHCONH$_2$)Pipd |
| 1323 | 2-F—Ph | MeOCO | 4-SCO$_2$Et-3-(=CHCONH$_2$)Pipd |

In the above Table, abbreviations indicate the following groups. ABOc: 8-azabicyclo[3.2.1]octan-8-yl Ac: acetyl
Acr: acroyl
Azed: 1-azetidinyl
Bu: butyl
i-Bu: isobutyl
c-Bu: cyclobutyl
Bur: butyryl
i-Bur: isobutyryl
Et: ethyl
Hxn: hexanoyl
Lau: lauroyl
Me: methyl
Olo: oleoyl
Pal: palmitoyl
Ph: phenyl
Pr: propyl
c-Pr: cyclopropyl
i-Pr: isopropyl
Pipd: 1-piperidinyl
Piv: pivaloyl
Prop: propionyl
Pyrd: 1-pyrrolidinyl
Stl: stearoyl
Val: valeryl In the above Table, preferred are the compounds of Compound Nos. 5, 10, 11, 12, 15, 17, 20, 21, 26, 29, 36, 41, 42, 43, 46, 48, 50, 51, 52, 57, 60, 67, 72, 73, 74, 77, 79, 81, 82, 83, 86, 88, 91, 98, 103, 104, 105, 108, 110, 113, 114, 117, 119, 122, 129, 134, 135, 136, 139, 141, 144, 148, 150, 153, 160, 165, 166, 167, 170, 172, 174, 175, 181, 184, 191, 196, 197, 198, 201, 203, 205, 206, 207, 208, 210, 212, 215, 222, 227, 228, 229, 232, 234, 236, 237, 241, 243, 246, 250, 253, 258, 259, 260, 263, 265, 267, 268, 272, 274, 277, 284, 287, 289, 290, 291, 294, 296, 299, 305, 308, 312, 314, 317, 318, 320, 324, 327, 334, 336, 337, 339, 340, 342, 343, 346, 349, 356, 358, 360, 361, 362, 364, 368, 371, 380, 382, 383, 385, 390, 392, 393, 395, 400, 403, 404, 407, 410, 413, 420, 422, 424, 425, 426, 428, 429, 432, 435, 444, 446, 447, 449, 454, 456, 457, 459, 462, 463, 464, 465, 466, 467, 468, 470, 471, 474, 477, 484, 486, 487, 489, 490, 492, 496, 499, 506, 508, 510, 511, 512, 514, 515, 518, 521, 528, 530, 532, 533, 535, 540, 542, 543, 545, 547, 548, 552, 553, 554, 555, 558, 560, 565, 568, 571, 574, 575, 584, 585, 589, 590, 591, 592, 593, 594, 595, 596, 597, 598, 599, 600, 601, 602, 603, 607, 608, 609, 610, 613, 616, 617, 618, 619, 620, 621, 622, 627, 628, 641, 642, 651, 652, 656, 657, 658, 659, 660, 661, 668, 669, 670, 675, 676, 688, 689, 708, 709, 713, 714, 716, 717, 723, 724, 728, 729, 735, 736, 751, 752, 761, 762, 768, 769, 773, 774, 780, 781, 795, 796, 800, 801, 802, 803, 804, 806, 808, 809, 813, 814, 815, 816, 817, 819, 821, 822, 826, 827, 828, 829, 832, 834, 835, 839, 840, 841, 842, 845, 847, 854, 855, 860, 861, 865, 866, 871, 872, 876, 883, 890, 891, 896, 897, 901, 902, 907, 908, 912, 922, 923, 928, 929, 930, 931, 936, 937, 944, 945, 949, 950, 951, 952, 956, 963, 964, 968, 969, 970, 971, 975, 979, 984, 986, 987, 992, 993, 997, 998, 1003, 1004, 1008, 1013, 1015, 1022, 1023, 1024, 1025, 1026, 1027, 1028, 1029, 1033, 1034, 1039, 1040, 1044, 1049, 1054, 1055, 1059, 1060, 1061, 1062, 1066, 1073, 1074, 1078, 1079, 1080, 1081, 1085, 1089, 1090, 1094, 1095, 1096, 1097, 1098, 1099, 1100, 1101, 1102, 1103, 1107, 1108, 1109, 1110, 1111, 1112, 1113, 1114, 1118, 1125, 1130, 1132, 1133, 1138, 1139, 1143, 1144, 1149, 1150, 1154, 1161, 1166, 1168, 1169, 1174, 1175, 1179, 1180, 1185, 1186, 1190, 1200, 1201, 1205, 1206, 1207, 1208, 1212, 1219, 1220, 1224, 1225, 1226, 1227, 1231, 1235, 1236, 1241, 1242, 1247, 1248, 1250, 1256, 1258, 1260, 1279, 1280, 1281, 1285, 1291, 1293, 1295, 1296, 1300, 1301, 1302, 1304, 1308, 1309, 1310, 1311, 1312, 1314, 1316 and 1318, more preferred are the compounds of Compound Nos. 5, 10, 20, 26, 29, 36, 41, 51, 57, 60, 67, 74, 82, 88, 91, 98, 113, 119, 122, 129, 134, 141, 144, 150, 153, 160, 175, 181, 184, 191, 198, 203, 206, 212, 215, 222, 237, 243, 246, 253, 258, 268, 274, 277, 284, 299, 305, 308, 314, 317, 324, 336, 339, 346, 349, 358, 361, 368, 371, 380, 382, 383, 390, 392, 400, 403, 410, 413, 422, 425, 432, 435, 444, 446, 447, 449, 454, 456, 462, 464, 467, 471, 474, 477, 486, 489, 496, 499, 508, 511, 518, 521, 530, 532, 533, 540, 542, 543, 552, 553, 554, 555, 558, 565, 568, 574, 589, 590, 591, 594, 595, 597, 598, 600, 601, 602, 603, 608, 609, 610, 613, 616, 617, 619, 620, 621, 651, 656, 658, 668, 669, 675, 688, 716, 717, 723, 728, 735, 761, 768, 773, 780, 800, 802, 803, 806, 813, 816, 826, 828, 829, 832, 839, 841, 854, 860, 865, 890, 896, 901, 922, 930, 944, 951, 963, 986, 987, 992, 997, 1003, 1022, 1023, 1028, 1033, 1039, 1054, 1060, 1061, 1073, 1079, 1089, 1094, 1096, 1098, 1102, 1107, 1109, 1113, 1114, 1132, 1138, 1143, 1149, 1168, 1174, 1179, 1185, 1200, 1207, 1219, 1226, 1236, 1242, 1248, 1250, 1256, 1279, 1281, 1296, 1300, 1302, 1304, 1308, 1309, 1310, 1312 and 1316, still more preferred are the compounds of Compound Nos. 5, 20, 26, 29, 36, 67, 82, 88, 91, 113, 119, 129, 144, 150, 175, 191, 206, 212, 253, 268, 274, 277, 336, 358, 400, 403, 410, 422, 425, 432, 435, 464, 467, 474, 477, 486, 496, 508, 518, 530, 540, 552, 554, 589, 590, 591, 594, 595, 600, 601, 602, 608, 610, 616, 617, 619, 620, 621, 656, 658, 716, 717, 728, 761, 773, 800, 803, 826, 890, 1022, 1023, 1039, 1096, 1098, 1102, 1107, 1109, 1132, 1143, 1168, 1179, 1200, 1236, 1242, 1248, 1296, 1302, 1308, 1312 and 1316, and particularly preferred are the compounds of:
Compound No. 82: 1-(α-cyclopropylcarbonyl-2-fluorobenzyl)-4-mercaptopiperidine,
Compound No. 88: 1-(2-fluoro-α-methoxycarbonylbenzyl)-4-mercaptopiperidine,
Compound No. 91: 1-(2-chloro-α-methoxycarbonylbenzyl)-4-mercaptopiperidine,
Compound No. 422: 1-(α-cyclopropylcarbonyl-2-fluorobenzyl)-3-ethoxycarbonylmethylidene-4-mercaptopiperidine,
Compound No. 435: 1-(2-chloro-α-methoxycarbonylbenzyl)-3-ethoxycarbonylmethylidene-4-mercaptopiperidine,
Compound No. 464: 1-(α-cyclopropylcarbonyl-2-fluorobenzyl)-3-carboxymethylidene-4-mercaptopiperidine,
Compound No. 477: 1-(2-chloro-α-methoxycarbonylbenzyl)-3-carboxymethylidene-4-mercaptopiperidine,
Compound No. 486: 1-(α-cyclopropylcarbonyl-2-fluorobenzyl)-3-(N,N-dimethylcarbamoyl)methylidene-4-mercaptopiperidine,
Compound No. 508: 1-(α-cyclopropylcarbonyl-2-fluorobenzyl)-3-(N-methylcarbarnoyl)methylidene-4-mercaptopiperidine,
Compound No. 589: 4-acetylthio-1-(α-cyclopropylcarbonyl-2-fluorobenzyl)piperidine,
Compound No. 591: 4-butyrylthio-1-(α-cyclopropylcarbonyl-2-fluorobenzyl)piperidine,
Compound No. 594: 1-(α-cyclopropylcarbonyl-2-fluorobenzyl)-4-pivaloylthiopiperidine,
Compound No. 601: 4-benzoylthio-1-(α-cyclopropylcarbonyl-2-fluorobenzyl)piperidine,
Compound No. 608: 4-acetylthio-1-(2-fluoro-α-methoxycarbonylbenzyl)piperidine,
Compound No. 620: 4-benzoylthio-1-(2-fluoro-α-methoxycarbonylbenzyl)piperidine,
Compound No. 621: 4-acetylthio-1-(2-chloro-α-methoxycarbonylbenzyl)piperidine,
Compound No. 800: 3-acetylthio-1-(α-cyclopropylcarbonyl-2-fluorobenzyl)azetidine,
Compound No. 1022: 4-acetylthio-1-(α-cyclopropylcarbonyl-2-fluorobenzyl)-3-ethoxycarbonylmethylidenepiperidine,
Compound No. 1039: 4-acetylthio-1-(2-chloro-α-methoxycarbonylbenzyl)-3-ethoxycarbonylmethylidenepiperidine,
Compound No. 1132: 4-acetylthio-1-(α-cyclopropylcarbonyl-2-fluorobenzyl)-3-(N,N-dimethylcarbamoyl)methylidenepiperidine, and
Compound No. 1168: 4-acetylthio-1-(α-cyclopropylcarbonyl-2-fluorobenzyl)-3-(N-methylcarbamoyl)methylidenepiperidine.

The compound of the formula (I) according to the present invention can be prepared easily by the following method:

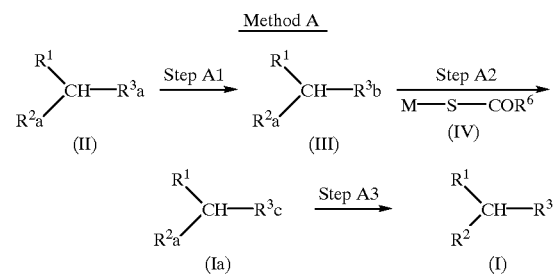

Method A

In the above formulae, $R^1$, $R^2$ and $R^3$ have the same meanings as described above, $R^2a$ has a similar meaning to $R^2$ except that the hydroxyl group contained in $R^2$ has been protected, $R^3a$ represents a substituted, 3 to 7 membered saturated cyclic amino group which may form a fused ring [the non-optional substituent of said group being a hydroxyl group or a hydroxy-($C_1$-$C_4$ alkyl) group, said cyclic amino group being further preferably substituted with a group of the formula $=CR^4aR^5a$ (in which $R^4a$ and $R^5a$ have similar meanings to $R^4$ and $R^5$, respectively, except that a carboxyl group is omitted)], $R^3b$ has a similar meaning to $R^3a$ except that the hydroxyl group or hydroxy moiety contained in $R^3a$ has been converted to a halogen atom (preferably, a chlorine or bromine atom), a $C_1$-$C_4$ alkanesulfonyloxy group (preferably, a methanesulfonyloxy group) which may be substituted with a halogen atom, or a substituted or unsubstituted benzenesulfonyloxy group (the substituent of said group being $C_1$-$C_4$ alkyl, halogen, $C_1$-$C_4$ alkoxy or nitro, of which methyl, chlorine, methoxy or nitro is preferred and p-methyl or p-nitro is particularly preferred), $R^3c$ has a similar meaning to $R^3a$ except that the hydroxyl group or hydroxy moiety contained in $R^3a$ has been converted to a group of the formula —S—$COR^6$ (in which $R^6$ has the same meaning as described later), $R^6$ represents a $C_1$-$C_4$ alkyl group (a methyl group is particularly preferred) and M represents an alkali metal atom (which may be, for example, lithium, sodium or potassium, of which sodium or potassium is preferred).

Examples of the protecting group for a hydroxyl group may be, for example, cyclic ether groups such as tetrahydrofuranyl or tetrahydropyranyl, a methoxymethyl group, a methoxymethoxymethyl group, a substituted or unsubstituted benzyl group (the substituent of said group being $C_1$-$C_4$ alkyl, halogen, $C_1$-$C_4$ alkoxy or nitro, of which methyl, chloro, methoxy or nitro is preferred and p-chloro or p-methoxy is particularly preferred), or a substituted or unsubstituted benzyloxycarbonyl group (the substituent of said group being $C_1$-$C_4$ alkyl, halogen, $C_1$-$C_4$ alkoxy or nitro, of which methyl, chloro, methoxy or nitro is preferred and p-chloro or p-methoxy is particularly preferred), of which a tetrahydropyranyl, methoxymethyl, benzyl, p-methoxybenzyl, p-chlorobenzyl, benzyloxycarbonyl, p-methoxybenzyloxycarbonyl or p-chlorobenzyloxycarbonyl group is preferred and a benzyl, p-methoxybenzyl, benzyloxycarbonyl or p-methoxybenzyloxycarbonyl group is particularly preferred.

Method A is a method for synthesizing the Compound (I). Step A1 is a step for synthesizing the compound of the formula (III) and is accomplished by reacting the compound of the formula (II) with a halogenating agent or sulfonylating agent.

Examples of the halogenating agent to be used in this step may be, for example, thionyl halides such as thionyl chloride or thionyl bromide, phosphorus trihalides such as phosphorus trichloride or phosphorus tribromide, phosphorus pentahalides such as phosphorus pentachloride or phosphorus pentabromide, phosphorus oxyhalides such as phosphorus oxychloride or phosphorus oxybromide, or tri(phenyl, unsubstituted or substituted with $C_1$–$C_4$ alkyl)phosphine—carbon tetrahalides such as triphenylphosphine—carbon tetrachloride, tritolylphosphine—carbon tetrachloride or triphenylphosphine—carbon tetrabromide, of which thionyl chloride, phosphorus trichloride, phosphorus tribromide, phosphorus pentachloride, triphenylphosphine—carbon tetrachloride, tritolylphosphine—carbon tetrachloride or triphenylphosphine—carbon tetrabromide is preferred, and thionyl chloride, triphenylphosphine—carbon tetrachloride or triphenylphosphine—carbon tetrabromide is particularly preferred.

Examples of the sulfonylating agent to be used in this step may be, for example, $C_1$–$C_4$ alkanesulfonyl halides which may be substituted with halogen, $C_1$–$C_4$ alkanesulfonic anhydrides which may be substituted with halogen and benzenesulfonyl halides which may be substituted, of which preferred are $C_1$–$C_4$ alkanesulfonyl chlorides which may be substituted with fluorine, $C_1$–$C_4$ alkanesulfonyl bromides, $C_1$–$C_4$ alkanesulfonic anhydrides which may be substituted with fluorine, benzenesulfonyl chloride which may be substituted or benzenesulfonyl bromide which may be substituted, more preferred are $C_1$–$C_2$ alkanesulfonyl chlorides, trifluoromethanesulfonyl chloride, $C_1$–$C_2$ alkanesulfonic anhydrides, trifluoromethanesulfonic anhydride, benzenesulfonyl chloride, toluenesulfonyl chloride or nitrobenzenesulfonyl bromide and particularly preferred are methanesulfonyl chloride, trifluoromethanesulfonyl chloride, benzenesulfonyl chloride or p-toluenesulfonyl chloride.

Compound (II) and the halogenating agent are reacted in the presence or absence (preferably, in the presence) of an inert solvent. There is no particular limitation on the nature of the inert solvent to be used in this step insofar as it has no adverse effects on the reaction, and may be, for example, a hydrocarbon such as hexane, benzene or toluene; a halogenated hydrocarbon such as dichloromethane, chloroform, carbon tetrachloride or 1,2-dichloroethane; an ether such as diethylether, tetrahydrofuran or dioxane; a ketone such as acetone or methyl ethyl ketone; a nitrile such as acetonitrile; an amide such as N,N-dimethylformamide, N,N-dimethylacetamide, N-methyl-2-pyrrolidone or hexamethylphosphoramide; a sulfoxide such as dimethylsulfoxide; or a mixture thereof, of which the ethers or halogenated hydrocarbons are preferred.

Although the reaction temperature depends on the nature of the starting material (II), halogenating agent and solvent, it is usually –10° C. to 200° C. (preferably 0° C. to 100° C.). The reaction time depends on the reaction temperature or the like but usually ranges from 30 minutes to 24 hours (preferably ranges from 1 hour to 12 hours).

Compound (II) and the sulfonylating agent are reacted in an inert solvent in the presence or absence (preferably in the presence) of a base. Here, inert solvents similar to those used for the reaction between Compound (II) and the halogenating agent can be used.

Preferred examples of the base to be employed in this step may be, for example, an alkali metal hydroxide such as lithium hydroxide, sodium hydroxide or potassium hydroxide; an alkali metal carbonate such as lithium carbonate, sodium carbonate or potassium carbonate; an alkali metal bicarbonate such as sodium bicarbonate or potassium bicarbonate; an alkali metal alkoxide such as lithium methoxide, sodium methoxide, sodium ethoxide or potassium t-butoxide; or an organic amine such as triethylamine, tributylamine, N-methylmorpholine, pyridine, 4-dimethylaminopyridine, picoline, lutidine, collidine, 1,5-diazabicyclo[4.3.0]-5-nonene or 1,8-diazabicyclo[5.4.0]-7-undecene, of which more preferred are the alkali metal carbonates or organic amines and particularly preferred is sodium carbonate, potassium carbonate, triethylamine, tributylamine, pyridine or lutidine. When organic amines in the liquid form are used, they can be used in a large excess as both the base and solvent.

The reaction temperature depends on the nature of the starting material (II), sulfonylating agent and solvent, however, it usually ranges from –10° C. to 100° C. (preferably from 0° C. to 50° C.). The reaction time depends on the reaction temperature or the like, however, it usually ranges from 30 minutes to 24 hours (preferably from 1 hour to 10 hours).

After the completion of the reaction, the target compound in each reaction is obtained from the reaction mixture in a conventional manner. For example, the target compound can be obtained by filtering off insoluble matter, if any, as desired and distilling off the solvent under reduced pressure, or distilling off the solvent under reduced pressure, adding water to the residue, extracting with a water immiscible organic solvent such as ethyl acetate, drying over anhydrous magnesium sulfate or the like and then distilling off the solvent. If necessary, purification can be carried out further in a conventional manner such as recrystallization or column chromatography.

Step A2 is a step for synthesising the compound of the formula (Ia) and is accomplished by reacting Compound (III) with the compound of the formula (IV) in an inert solvent.

There is no particular limitation on the nature of the inert solvent to be used in this step insofar as it has no adverse effects on the reaction, and may be, for example, an ether such as diethylether, tetrahydrofuran or dioxane; a ketone such as acetone or methyl ethyl ketone; an ester such as ethyl acetate or butyl acetate; an alcohol such as methanol, ethanol, propyl alcohol, isopropyl alcohol or butyl alcohol; a nitrile such as acetonitrile; an amide such as N,N-dimethylformamide, N,N-dimethylacetamide, N-methyl-2-pyrrolidone or hexamethylphosphoramide; a sulfoxide such as dimethylsulfoxide, or a mixture thereof, of which the amides or sulfoxides are preferred.

The reaction temperature depends on the nature of the starting material (III), starting material (IV) and solvent, however, it usually ranges from 0° C. to 200° C. (preferably from 20° C. to 150° C.). The reaction time depends on the reaction temperature or the like, however, it usually ranges from 30 minutes to 24 hours (preferably from 1 hour to 12 hours).

After the completion of the reaction, the target compound in this reaction is obtained from the reaction mixture in a conventional manner. For example, the target compound can be obtained by filtering off insoluble matter, if any, as desired and distilling off the solvent under reduced pressure, or distilling off the solvent under reduced pressure, adding water to the residue, extracting with a water immiscible organic solvent such as ethyl acetate, drying over anhydrous magnesium sulfate or the like and then distilling off the solvent. If necessary, purification can be carried out further in a conventional manner such as recrystallization or column chromatography.

Step A3 is a step conducted if necessary and it comprises:

Reaction (a): reaction for converting a group of —S—$COR^6$ (in which $R^6$ has the same meaning as described above) contained in $R^3c$ into a mercapto group, Reaction (b): reaction for acylating the mercapto group formed in Reaction (a), Reaction (c): reaction for removing the protecting group of the hydroxyl group contained in $R^2a$, Reaction (d): reaction for converting the alkoxycarbonyl group contained in $R^3c$ into a carboxy group, and Reaction (e): reaction for isomerizing a double-bond-based cis/trans form contained in $R^3c$.

The order of these steps can be changed as desired.

Reaction (a):

The reaction to convert the group of —S—COR$^6$ (in which $R^6$ has the same meaning as described above) into a mercapto group in Reaction (a) is accomplished by hydrolyzing the corresponding compound with an acid or alkali (preferably, acid) or decomposing it by the addition of an alcohol. This reaction is carried out in accordance with a manner well known in organic synthetic chemistry. When hydrolysis is carried out with an acid, the methoxymethyl group, methoxymethoxymethyl group or cyclic ether group, which is one of the protecting groups of the hydroxyl group contained in $R^2a$, is removed at the same time, while when hydrolysis is carried out with an alkali, the alkoxycarbonyl group contained in $R^3c$ is converted into a carboxy group at the same time.

Examples of the acid to be used in this reaction may be, for example, inorganic acids such as hydrogen chloride, nitric acid, hydrochloric acid or sulfuric acid, or organic acids such as acetic acid, trifluoroacetic acid, methanesulfonic acid or p-toluenesulfonic acid, of which hydrogen chloride, hydrochloric acid, sulfuric acid or trifluoroacetic acid is preferred and hydrogen chloride or hydrochloric acid is particularly preferred.

Examples of the alkali to be used in this reaction may be, for example, an alkali metal hydroxide such as sodium hydroxide or potassium hydroxide; alkali metal carbonate such as sodium carbonate or potassium carbonate; or alkali metal bicarbonate such as sodium bicarbonate or potassium bicarbonate, of which alkali metal hydroxides (particularly, sodium hydroxide) are preferred.

There is no particular limitation on the nature of the inert solvent to be used in this reaction insofar as it has no adverse effects on the reaction, and may be, for example, a hydrocarbon such as hexane, benzene or toluene; a halogenated hydrocarbon such as dichloromethane, chloroform, carbon tetrachloride or 1,2-dichloroethane; an ether such as diethylether, tetrahydrofuran or dioxane; a ketone such as acetone or methyl ethyl ketone; an alcohol such as methanol, ethanol, propyl alcohol, isopropyl alcohol or butyl alcohol; a carboxylic acid such as formic acid, acetic acid, propionic acid or butanoic acid; water, or a mixture thereof, of which an alcohol, a carboxylic acid, water, or a mixture thereof is preferred in the case of hydrolysis with an acid and an alcohol or water is preferred in the case of hydrolysis with a base.

The reaction temperature depends on the nature of the starting material (Ia), acid, base and solvent, however, it usually ranges from $-10°$ C. to $70°$ C. (preferably from $0°$ C. to $50°$ C.).

The reaction time depends on the reaction temperature or the like, however, it usually ranges from 30 minutes to 48 hours (preferably from 1 hour to 20 hours).

After the completion of the reaction, the target compound in this reaction is obtained from the reaction mixture in a conventional manner. For example, the target compound can be obtained by filtering off insoluble matter, if any, as desired and neutralizing the reaction mixture as desired if the reaction mixture is acidic or basic and distilling off the solvent under reduced pressure, or distilling off the solvent under reduced pressure, adding water to the residue, extracting with a water immiscible organic solvent such as ethyl acetate, drying over anhydrous magnesium sulfate or the like and then distilling off the solvent. If necessary, purification can be carried out further in a conventional manner such as recrystallization or column chromatography.

Reaction (b)

The reaction to acylate the mercapto group in Reaction (b) is carried out by reacting the corresponding compound with an acylating agent in an inert solvent in the presence or absence (preferably, in the presence) of a base. This reaction is conducted in a similar manner to that described in the sulfonylating reaction in Step A1 except for the use of the below-described acylating agent instead of the sulfonylating agent.

Examples of the acylating agent to be used in this reaction may be, for example, $C_2$–$C_{20}$ alkanoyl halides, mixed acid anhydrides of formic acid and acetic acid, $C_2$–$C_{20}$ alkanecarboxylic anhydrides, $C_3$–$C_{20}$ alkenoyl halides, $C_3$–$C_{20}$ alkenecarboxylic anhydrides, substituted or unsubstituted benzoyl halides, substituted or unsubstituted benzoic anhydrides or $C_1$–$C_4$ alkyl halogenocarbonates, of which preferred are $C_2$–$C_{20}$ alkanoyl chlorides or bromides, mixed acid anhydrides of formic acid and acetic acid, $C_2$–$C_{20}$ alkanecarboxylic anhydrides, $C_3$–$C_{20}$ alkenoyl chloride or bromide, $C_3$–$C_{20}$ alkenecarboxylic anhydrides, substituted or unsubstituted benzoyl chloride or bromide, substituted or unsubstituted benzoic anhydrides, or $C_1$–$C_4$ alkyl chloro- or bromo-carbonates, more preferred are $C_2$–$C_{20}$ alkanoyl chlorides, mixed acid anhydrides of formic acid and acetic acid, $C_2$–$C_6$ alkanecarboxylic anhydrides, $C_3$–$C_{20}$ alkenoyl chlorides, substituted or unsubstituted benzoyl chloride or $C_1$–$C_4$ alkyl chlorocarbonates and particularly preferred are $C_2$–$C_{20}$ alkanoyl chlorides, mixed acid anhydrides of formic acid and acetic acid, $C_3$–$C_{20}$ alkenoyl chlorides, substituted or unsubstituted benzoyl chloride or $C_1$–$C_4$ alkyl chlorocarbonates.

Reaction (c)

The reaction to remove the protecting group of the hydroxyl group contained in $R^2a$ in Reaction (c) depends on the nature of the protecting group and is carried out in a manner well known in organic synthetic chemistry.

When the protecting group of the hydroxyl group is a substituted or unsubstituted benzyl group or substituted or unsubstituted benzyloxycarbonyl group, the removal is carried out by reacting the corresponding compound with hydrogen (usually at 1 to 10 atmospheric pressure, preferably 1 to 3 atmospheric pressure) in an inert solvent (preferably, an alcohol such as methanol, ethanol or isopropanol, an ether such as diethyl ether, tetrahydrofuran or dioxane, an aromatic hydrocarbon such as toluene, benzene or xylene, an aliphatic hydrocarbon such as hexane or cyclohexane, an ester such as ethyl acetate or butyl acetate, a fatty acid such as acetic acid, or a mixture of the above exemplified organic solvent and water) in the presence of a catalytic hydrogenating catalyst (preferably, palladium-carbon, platinum oxide, platinum black, rhodium-aluminum oxide, triphenylphosphine-rhodium chloride, palladium-barium sulfate or the like).

The reaction temperature usually ranges from $0°$ C. to $100°$ C. (preferably from $20°$ C. to $80°$ C.). The reaction time depends on the reaction temperature or the like, however, it usually ranges from 30 minutes to 48 hours (preferably from 1 hour to 24 hours).

When the protecting group of the hydroxyl group is a methoxymethyl group, methoxymethoxymethyl group or cyclic ether group, the removal is carried out, for example, by reacting the corresponding compound with an acid (for example, an inorganic acid such as hydrogen chloride, nitric acid, hydrochloric acid or sulfuric acid, an organic acid such as acetic acid, trifluoroacetic acid, methanesulfonic acid or p-toluenesulfonic acid, or a Lewis acid such as boron trifluoride, of which an inorganic acid or organic acid is preferred and hydrochloric acid, sulfuric acid or trifluoroacetic acid is more preferred) in an inert solvent (a hydrocarbon such as hexane or benzene, a halogenated hydrocarbon such as methylene chloride, chloroform or carbon tetrachloride, an ester such as ethyl acetate, a ketone such as acetone or methyl ethyl ketone, an alcohol such as methanol or ethanol, an ether such as diethylether, tetrahydrofuran or dioxane, or a mixture of the above-exemplified solvent with water, of which an ester, ether or halogenated hydrocarbon is preferred).

The reaction temperature usually ranges from −10° C. to 100° C. (preferably from −5° C. to 50° C.). The reaction time depends on the reaction temperature or the like, however, it usually ranges from 5 minutes to 48 hours (preferably from 30 minutes to 10hours).

Alternatively, the protecting group of the hydroxyl group can be removed selectively by changing the nature of the protecting group of the hydroxyl group and selecting the reaction conditions, thereby distinguishing this reaction from the reaction for converting the group of the formula —S—COR$^6$ (in which R$^6$ has the same meaning as described above) contained in R$^3$c into a mercapto group or the reaction for converting the alkoxycarbonyl group contained in R$^3$c into a carboxyl group.

After the completion of the reaction, the target compound in this reaction is obtained from the reaction mixture in a conventional manner. For example, the target compound can be obtained by neutralizing the reaction mixture as desired, filtering off insoluble matter, if any, adding a water immiscible organic solvent such as ethyl acetate, washing with water and then distilling off the solvent. If necessary, the target compound so obtained can be purified further in a conventional manner such as recrystallization, reprecipitation or column chromatography.

Reaction (d):

The reaction to convert the alkoxycarbonyl group contained in R$^3$c into a carboxy group in Reaction (d) is carried out in similar manner to that described in the reaction of converting the group of the formula —S—COR$^6$ (in which R$^6$ has the same meaning as described above) into a mercapto group in Reaction (a). Alternatively, the alkoxycarbonyl group of R$^3$c can be hydrolyzed, distinguished from that of R$^2$a, by reacting with a strong acid (ex. concentrated hydrochloric acid, concentrated sulfuric acid, concentrated nitric acid or the like) in an inert solvent (ex. an aliphatic carboxylic acid such as acetic acid).

Reaction (e):

The reaction to isomerize the double-bond-based cis/trans form contained in R$^3$c in Reaction (e) is carried out by exposing the corresponding compound to light in an inert solvent in the presence or absence (preferably in the absence) of a sensitizer.

The light source to be used for the exposure to light is a low pressure mercury lamp (20 W to 100 W, preferably 32 W) and as the sensitizer, benzophenone, fluorenone or anthraquinone is employed.

This reaction can also be effected by adding an organic sulfur compound such as dimethyl disulfide, diethyl disulfide or diphenyl disulfide with a view to promoting the reaction and/or suppressing the side reaction.

There is no particular limitation on the nature of the inert solvent to be used in this reaction insofar as it has no adverse effects on the reaction, and may, for example, include an ether such as diethylether, tetrahydrofuran or dioxane; an ester such as ethyl acetate or butyl acetate; an alcohol such as methanol, ethanol, propyl alcohol, isopropyl alcohol or butyl alcohol; a nitrile such as acetonitrile; an amide such as N,N-dimethylformamide, N,N-dimethylacetamide, N-methyl-2-pyrrolidone or hexamethylphosphoramide; a sulfoxide such as dimethylsulfoxide; or a mixture thereof, of which alcohols or nitriles are preferred.

The reaction temperature depends on the nature of the starting material, light source and the solvent, however, it usually ranges from −20° C. to 100° C. (preferably from 0° C. to 50° C.). The reaction time depends on the reaction temperature or the like, however, it usually ranges from 5 minutes to 8 hours (preferably from 10 minutes to 3 hours).

After the completion of the reaction, the target compound in this reaction can be obtained from the reaction mixture in a conventional manner. For example, the target compound can be obtained by filtering off insoluble matter, if any, as desired and distilling off the solvent under reduced pressure, or distilling off the solvent under reduced pressure, adding water to the residue, extracting with a water immiscible organic solvent such as ethyl acetate, drying over anhydrous magnesium sulfate or the like and then distilling off the solvent. If necessary, purification can be carried out further in a conventional manner such as recrystallization or column chromatography.

Compound (I) can be converted into a pharmaceutically acceptable salt thereof by treating with an acid in a conventional manner. For example, it can be obtained by reacting with a corresponding acid at room temperature for 5 minutes to 1 hour in an inert solvent (preferably, an ether such as diethylether, tetrahydrofuran or dioxane, an alcohol such as methanol or ethanol or a halogenated hydrocarbon such as methylene chloride or chloroform) and then distilling off the solvent under reduced pressure.

The starting material (II) of the present invention can be prepared easily in accordance with the below-described methods:

Method B

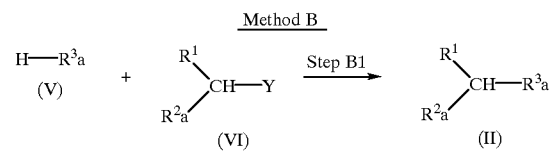

Method C

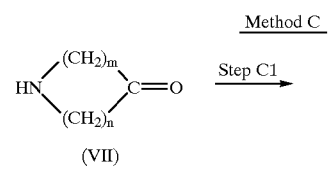

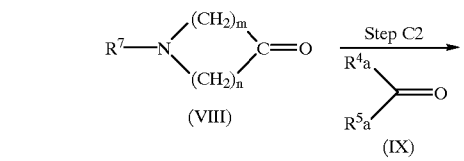

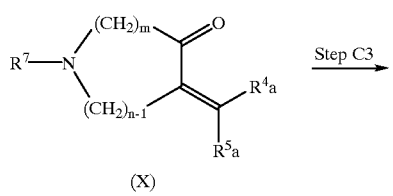

(X)

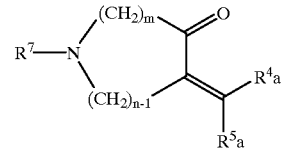

(X)

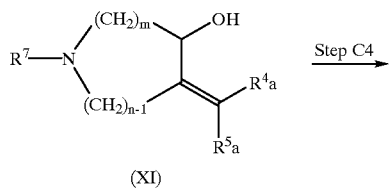

(XI)

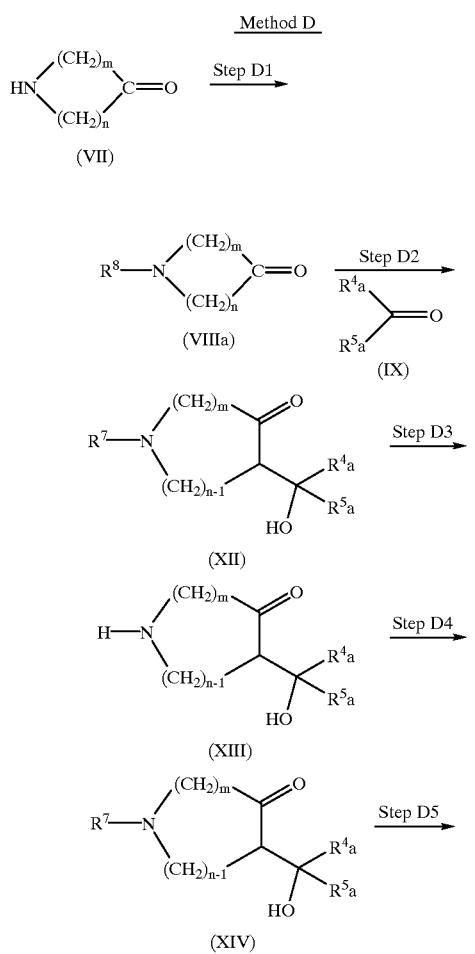

In the above formula, $R^1$, $R^2a$, $R^3a$, $R^4a$ and $R^5a$ have the same meanings as described above, $R^7$ represents a protecting group for the amino group removable under acid conditions, $R^8$ represents a protecting group for the amino group removable under reducing conditions, Y represents a halogen atom (preferably, a chlorine or bromine atom), m stands for 0 to 3 and n stands for 1 or 2.

The protecting group for the amino group removable under acid conditions of $R^7$, may be, for example, a trityl group or a t-butoxycarbonyl group, while the protecting group for the amino group removable under reducing conditions of $R^8$, may be, for example, a substituted or unsubstituted benzyl group or a substituted or unsubstituted benzyloxycarbonyl group similar to the above-described protecting group of the hydroxyl group, of which benzyl, p-methoxybenzyl, p-chlorobenzyl, benzyloxycarbonyl, p-methoxybenzyloxycarbonyl or p-chlorobenzyloxycarbonyl group is preferred and benzyl or p-methoxybenzyl group is particularly preferred.

Method B is a method for synthesizing the Compound (II).

Step B1 is a step for synthesizing the Compound (II) and it comprises reacting a compound of the formula (V) with a compound of the formula (VI) at 0° C. to 200° C. (preferably, 20° C. to 150° C.) for 1 to 24 hours (preferably, 2 to 15 hours) in an inert solvent (preferably, an amide such as N,N-dimethylacetamide, N,N-dimethylformamide, N-methylpyrrolidone or hexamethylphosphoramide or a sulfoxide such as dimethylsulfoxide) in the presence or absence of a base (preferably in the presence of an alkali metal carbonate such as sodium carbonate or potassium carbonate).

A corresponding amide derivative can be prepared by hydrolyzing Compound (II) having as $R^3a$ an alkoxycarbonyl group in a similar manner to that described in Reaction (d) in the above-described Step A3 of Method A to prepare the corresponding carboxy derivative, reacting the resulting carboxy derivative with a $C_1$–$C_4$ alkyl halogenocarbonate such as methyl chlorocarbonate, ethyl chlorocarbonate, ethyl bromocarbonate, propyl chlorocarbonate, butyl chlorocarbonate or isobutyl chlorocarbonate in a similar manner to that described in Reaction (b) of Step A3 of Method A to prepare the corresponding active ester derivative, and then reacting the resulting active ester derivative with ammonia or a mono- or di-($C_1$–$C_4$ alkyl)amine at –10° C. to 100° C. (preferably, 10° C. to 50° C.) for 1 to 24 hours (preferably, 2 to 10 hours) in an inert solvent (preferably, a halogenated hydrocarbon such as dichloromethane, chloroform, carbon tetrachloride or 1,2-dichloroethane).

Method C is a method for synthesizing the Compound (Va), that is, the starting material (V) in Method B having a substituent represented by the formula $=CR^4aR^5a$ (in which $R^4a$ and $R^5a$ have the same meanings as described above).

Step C1 is a step for synthesizing the compound represented by the formula (VIII) and it comprises reacting a compound represented by the formula (VII) with a trityl halide such as trityl chloride or trityl bromide, a t-butoxycarbonyl halide such as t-butoxycarbonyl chloride or t-butoxycarbonyl bromide or di-t-butyl dicarbonate at 0° C. to 150° C. (preferably, 20° C. to 100° C.) for 1 to 24 hours (preferably 2 to 10 hours) in an inert solvent (preferably, a halogenated hydrocarbon such as dichloromethane, chloroform, carbon tetrachloride or 1,2-dichloroethane, an amide such as N,N-dimethylacetamide, N,N-dimethylformamide, N-methylpyrrolidone or hexamethylphosphoramide or a sulfoxide such as dimethylsulfoxide) in the presence or absence of a base (preferably in the presence of an alkali metal carbonate such as lithium carbonate, sodium carbonate or potassium carbonate).

Step C2 is a step for synthesizing the compound represented by the formula (X) and it comprises reacting Compound (VIII) with a di-($C_1$–$C_4$ alkyl)amine or 3 to 6 membered cyclic amine (preferably, dimethylamine, diethylamine, pyrrolidine, piperidine or morpholine and particularly preferably, pyrrolidine, piperidine or morpholine) at 60° C. to 200° C. (preferably 80° C. to 150° C.) for 30 minutes to 15 hours (preferably 1 hour to 10 hours) in an inert solvent (preferably, an aromatic hydrocarbon such as benzene, toluene or xylene) while carrying out azeotropic dehydration, thereby preparing the corresponding enamine derivative; and then reacting the resulting enamine derivative with a compound of the formula (IX) at 60° C. to 200° C. (preferably 80° C. to 150° C.) for 30 minutes to 10 hours (preferably 1 hour to 5 hours) in an inert solvent (preferably, an aromatic hydrocarbon such as benzene, toluene or xylene) while carrying out azeotropic dehydration.

Step C3 is a step for synthesizing the compound of the formula (XI) and it comprises reacting Compound (X) with a reducing agent (preferably, a borohydride compound such as sodium borohydride or sodium cyanoborohydride) at 0° C. to 100° C. (preferably, 5° C. to 50° C.) for 10 minutes to 6 hours (preferably, for 30 minutes to 3 hours) in an inert solvent (preferably, an alcohol such as methanol or ethanol).

Step C4 is a step for synthesizing Compound (Va) and it is accomplished by the removal of the protecting group from the amino group of Compound (XI). This step is carried out in a similar manner to that described in Reaction (c) of Step A3 of Method A for the removal of the protecting group of the hydroxyl group under acid conditions.

Method D is an alternative method for synthesizing Intermediate (X) of Method C.

Step D1 is a step for synthesizing the compound of the formula (VIIIa). Compound (VII) and a substituted or unsubstituted benzyl halide or a substituted or unsubstituted benzyloxycarbony halide (preferably, chloride) are treated in a similar manner to that described in Step C1 of Method C.

Step D2 is a step for synthesizing the compound of the formula (XII) and it comprises reacting Compound (VIIIa) with a di-($C_1$–$C_4$ alkyl)amine or 3 to 6 membered cyclic amine (preferably, dimethylamine, diethylamine, pyrrolidine, piperidine or morpholine and particularly preferably, pyrrolidine, piperidine or morpholine) in a similar manner to that described in the former stage of Step C2 of Method C, thereby preparing the corresponding enamine derivative; and reacting the resulting enamine derivative with the compound of the formula (IX) at −10° C. to 100° C. (preferably, 10° C. to 50° C.) for 1 to 24 hours (preferably, 2 to 20 hours) in an inert solvent (preferably, a halogenated hydrocarbon such as dichloromethane, chloroform, carbon tetrachloride or 1,2-dichloroethane) in the presence of an acid catalyst (preferably, a Lewis acid such as boron trifluoride—ether complex, aluminum chloride, titanium tetrachloride or tin tetrachloride).

Step D3 is a step for synthesizing the compound of the formula (XIII) and is accomplished by the removal of the protecting group from the amino group of Compound (XII). This step is carried out in a similar manner to that described in Reaction (C) of Step A3 of Method A for the removal of the protecting group from the hydroxyl group under reducing conditions.

Step D4 is a step for synthesizing the compound of the formula (XIV) and is accomplished by the protection of the amino group of Compound (XIII). This step is carried out in a similar manner to that described in Step C1 of Method C.

Step D5 is a step for synthesizing Compound (X) and it comprises sulfonylating of Compound (XIV) in a similar manner to that described in Step A1 of Method A and reacting the resulting sulfonyloxy derivative with a base (preferably, an organic amine such as triethylamine, N-methylmorpholine, pyridine, 4-dimethylaminopyridine, 1,5-diazabicyclo[4.3.0]-5-nonene or 1,8-diazabicyclo [5.4.0]-7-undecene) at −10° C. to 100° C. (preferably 10° C. to 50° C.) for 30 minutes to 10 hours (preferably, for 1 hour to 5 hours) in an inert solvent (preferably, a halogenated hydrocarbon such as dichloromethane, chloroform, carbon tetrachloride or 1,2-dichloroethane).

After the completion of the reaction, the target compound in each reaction is obtained from the reaction mixture in a conventional manner. For example, the target compound can be obtained by filtering off insoluble matter, if any, as desired, neutralizing the reaction mixture when it is acidic or alkaline and distilling off the solvent under reduced pressure, or distilling off the solvent under reduced pressure, adding water to the residue, extracting with a water immiscible organic solvent such as ethyl acetate, drying over anhydrous magnesium sulfate or the like and then distilling off the solvent. If necessary, purification can be carried out further in a conventional manner such as recrystallization or column chromatography.

Starting material (VI) is known or prepared by a known method [for example, Japanese Patent Application Kokai No. Sho 59-27895 (EP 99802) or Japanese Patent Application Kokai No. Hei 6-41139 (EP542411)]. Starting material compound (V) is known or prepared by a known method [for example, *J. Org. Chem.*, 37, 3953 (1972).].

The compound of the formula (I) according to the present invention has excellent platelet aggregation inhibitory action or arteriosclerosis progress inhibitory action and has low toxicity so that it is useful as a therapeutic agent or a preventive agent for thrombosis, embolism or arteriosclerosis.

The present invention will hereinafter be described in further detail by examples, preparations, tests and formulation. It should however be borne in mind that the scope of the present invention is not limited thereto.

EXAMPLE 1

1-(α-Cyclopropylcarbonyl-2-fluorobenzyl)-4-mercaptopiperidine hydrochloride (Exemplified Compound No. 82)

(a) 4-Acetylthio-1-(α-cyclopropylcarbonyl-2-fluorobenzyl) piperidine (Exemplified Compound No. 589)

In 50 ml of dichloromethane, 8.0 g (28.9 mmol) of 1-(α-cyclopropylcarbonyl-2-fluorobenzyl)-4-hydroxypiperidine were dissolved, followed by the addition of 2.92 g (28.9 mmol) of triethylamine. To the resulting mixture, a solution of 3.31 g (28.9 mmol) of methanesulfonyl chloride in 10 ml of dichloromethane was added dropwise under ice cooling, followed by stirring at room temperature for 1 hour. The solvent was distilled off under reduced pressure. Ethyl acetate was added to the residue and triethylamine hydrochloride so precipitated was filtered off. The filtrate was concentrated by evaporation under reduced pressure, whereby crude 1-(α-cyclopropylcarbonyl-2-fluorobenzyl)-4-methylsulfonyloxypiperidine was obtained. To the crude product, 50 ml of dimethylsulfoxide (DMSO) and 19.8 g (170 mmol) of potassium thioacetate were added and the resulting mixture was stirred at 50° C. for 4 hours. After the addition of water, the resulting mixture was extracted with ethyl acetate. The extract was dried over anhydrous sodium sulfate. The solvent was distilled off under reduced pressure and the residue was subjected to chromatography on a silica gel column (eluting solvent: toluene/ethylacetate=19/1), whereby a reddish brown oil was obtained. The resulting oil was crystallized from hexane, whereby 3.6 g of the title compound were obtained as light brown crystals (yield: 37%).

Melting point: 78° C. to 80° C.; NMR spectrum (CDCl$_3$, δ): 0.79–0.87(2H,m), 0.98–1.04(2H,m), 1.66–1.80(2H,m), 1.90–2.00(2H,m), 2.16–2.22(2H,m), 2.28(3H,s), 2.32–2.35 (1H,m), 2.70–2.78(1H,m), 2.80–2.88(1H,m), 3.38–3.47(1H, m), 4.62(1H,s), 7.08–7.38(4H,m); Mass spectrum (CI, m/z): 336 (M$^+$+1); IR spectrum (KBr, ν$_{max}$ cm$^{-1}$): 1689.

(b) 1-(α-Cyclopropylcarbonyl-2-fluorobenzyl)-4-mercaptopiperidine hydrochloride

In 50 ml of ethanol, 2.00 g (5.97 mmol) of 4-acetylthio-1-(α-cyclopropylcarbonyl-2-fluorobenzyl)piperidine were dissolved. An adequate amount of hydrogen chloride gas was blown into this solution and the resulting solution was allowed to stand overnight at room temperature. The solvent was distilled off under reduced pressure. The residue was crystallized from diethyl ether, whereby 1.95 g of the title compound were obtained as slightly brown crystals (yield: 99%).

Melting point: 135 to 140° C.; Anal.Calcd for C$_{16}$H$_{20}$FNOS.HCl.1/4H$_2$O:C,57.48;H,6.48;N,4.19; Found:C,57.33;H,6.43;N,4.15; Mass spectrum (CI, m/z): 294 (M$^+$+1).

EXAMPLE 2

1-(2-Chloro-α-methoxycarbonylbenzyl)-4-mercaptopiperidine hydrochloride (Exemplified Compound No. 91)

(a) 4-Acetylthio-1-(2-chloro-α-methoxycarbonylbenzyl) piperidine (Exemplified Compound No. 621)

In a similar manner to that described in Example 1(a) except for the use of 1-(2-chloro-α-methoxycarbonylbenzyl)-4-hydroxypiperidine instead of 1-(α-cyclopropylcarbonyl-2-fluorobenzyl)-4-hydroxypiperidine, the reaction was effected, whereby the title compound was obtained as a reddish brown oil in a yield of 37%.

NMR spectrum(CDCl$_3$, δ): 1.60–1.80(2H,m), 1.85–2.00 (2H,m), 2.10–2.25(1H,m), 2.30(3H,s), 2.32–2.48(1H,m), 2.55–2.75(1H,m), 2.80–2.90(1H,m), 3.40–3.60(1H,m), 3.70 (3H,s), 4.70(1H,s), 7.20–7.65(4H,m); Mass spectrum(CI, m/z): 342(M$^+$+1).

(b) 1-(2-Chloro-α-methoxycarbonylbenzyl)-4-mercaptopiperidine hydrochloride

In a similar manner to that described in Example 1(b) except for the use of 4-acetylthio-1-(2-chloro-α-methoxycarbonylbenzyl)piperidine instead of 4-acetylthio-1-(α-cyclopropylcarbonyl-2-fluorobenzyl)piperidine, the reaction was effected, whereby the title compound was obtained as slightly brown crystals in a quantitative yield.

Melting point: 134 to 140° C.; Mass spectrum (CI, m/z): 300 (M$^+$+1).

EXAMPLE 3

1-(2-Fluoro-α-methoxycarbonylbenzyl)-4-mercaptopiperidine hydrochloride (Exemplified Compound No. 88)

(a) 4-Acetylthio-1-(2-fluoro-α-methoxycarbonylbenzyl) piperidine (Exemplified Compound No. 608)

In a similar manner to that described in Example 1(a) except for the use of 1-(2-fluoro-α-methoxycarbonylbenzyl)-4-hydroxypiperidine instead of 1-(α-cyclopropylcarbonyl-2-fluorobenzyl)-4-hydroxypiperidine, the reaction was effected, whereby the title compound was obtained as a light yellow solid (amorphous) in a yield of 45.6%.

NMR spectrum (CDCl$_3$, δ): 1.65–1.78(2H,m), 1.88–1.99 (2H,m), 2.20–2.33(4H,m), 2.39(1H,t,J=9.6 Hz), 2.75–2.86 (2H,m), 3.40–3.50(1H,m), 3.71(3H,s), 4.53(1H,s), 7.04–7.49(4H,m); Mass spectrum(CI, m/z): 326 (M$^+$+1).

(b) 1-(2-Fluoro-α-methoxycarbonylbenzyl)-4-mercaptopiperidine hydrochloride

In a similar manner to that described in Example 1(b) except for the use of 4-acetylthio-1-(2-fluoro-α-methoxycarbonylbenzyl)piperidine instead of 4-acetylthio-1-(α-cyclopropylcarbonyl-2-fluorobenzyl)piperidine, the title compound was obtained as a light yellow solid (amorphous) in a yield of 97.1%.

NMR spectrum (CDCl$_3$, δ): 1.70–2.24(3H,m), 2.47–3.13 (3.5H,m), 3.21–3.36(0.5H,m), 3.38–3.72(2.5H,m), 3.83, 3.84(total 3H, each s), 3.92–4.02 (0.5H,m), 5.21,5.24(total 1H, each s), 7.20–7.93(4H,m), 12.91–13.34(1H,m); Mass spectrum (CI, m/z): 284(M$^+$+1).

EXAMPLE 4

3-Acetylthio-1-(α-cyclopropylcarbonyl-2-fluorobenzyl)piperidine (Exemplified Compound No. 716)

In a similar manner to that described in Example 1(a) except for the use of 1-(α-cyclopropylcarbonyl-2-fluorobenzyl)-3-hydroxypiperidine instead of 1-(α-cyclopropylcarbonyl-2-fluorobenzyl)-4-hydroxypiperidine, the reaction was effected, whereby the title compound was obtained as a reddish brown oil in a yield of 69%.

NMR spectrum (CDCl$_3$, δ): 0.75–0.95(2H,m), 1.00–1.10 (2H,m), 1.45–1.68(1H,m), 1.72–1.85(2H,m), 1.90–2.25(2H, m), 2.30,2.32(total 3H, each s), 2.35–2.48(1H,m), 2.80–3.02 (2H,m), 3.05–3.15(1H,m), 3.16–3.30(1H,m), 5.12(1H,s), 7.05–7.45(4H,m); Mass spectrum (CI, m/z): 336 (M$^+$+1).

EXAMPLE 5

1-(α-Cyclopropylcarbonyl-2-fluorobenzyl)-3-mercaptopyrrolidine hydrochloride (Exemplified Compound No. 20)

(a) 3-Acetylthio-1-(α-cyclopropylcarbonyl-2-fluorobenzyl) pyrrolidine (Exemplified Compound No. 552)

In a similar manner to that described in Example 1(a) except for the use of 1-(α-cyclopropylcarbonyl-2-fluorobenzyl)-3-hydroxypyrrolidine instead of 1-(α-cyclopropylcarbonyl-2-fluorobenzyl)-4-hydroxypiperidine, the reaction was effected, whereby the title compound was obtained as a brown oil in a yield of 51%.

NMR spectrum (CDCl$_3$, δ): 0.78–0.85(2H,m), 0.97–1.02 (2H,m), 1.75–1.78(1H,m), 2.09–2.15(1H,m), 2.28(3H,s), 2.32–3.39(1Hm), 2.48–2.61(2H,m), 2.72–2.80(1H,m), 2.97–3.10(1H,m), 3.91–3.97(1H,m), 4.63,4.65 (total 1H, each s), 7.06–7.48(4H,m); Mass spectrum (CI, m/z): 321 (M$^+$+1); IR spectrum (liquid membrane, ν$_{max}$ cm$^{-1}$): 1692.

(b) 1-(α-Cyclopropylcarbonyl-2-fluorobenzyl)-3-mercaptopyrrolidine hydrochloride In a similar manner to that described in Example 1(b) except for the use of 3-acetylthio-1-(α-cyclopropylcarbonyl-2-fluorobenzyl)pyrrolidine instead of 4-acetylthio-1-(α-cyclopropylcarbonyl-2-fluorobenzyl) piperidine, the reaction was effected, whereby the title compound was obtained as a slightly brown solid (amorphous) in a yield of 74%.

Mass spectrum (CI, m/z): 280 (M$^+$+1); IR spectrum (KBr, $\nu_{max}$ cm$^{-1}$): 1710.

EXAMPLE 6

1-(α-Cyclopropylcarbonyl-2-fluorobenzyl)-3-mercaptoazetidine hydrochloride (Exemplified Compound No. 206)

(a) 3-Acetylthio-1-(α-cyclopropylcarbonyl-2-fluorobenzyl)azetidine (Exemplified Compound No. 800)

In a similar manner to that described in Example 1(a) except for the use of 1-(α-cyclopropylcarbonyl-2-fluorobenzyl)-3-hydroxyazetidine instead of 1-(α-cyclopropylcarbonyl-2-fluorobenzyl)-4-hydroxypiperidine, the reaction was effected, whereby the title compound was obtained as light yellow crystals in a yield of 54%.

Melting point: 49 to 52° C.; NMR spectrum (CDCl$_3$, δ): 0.74–0.87(2H,m), 0.94–1.01(2H,m), 1.92–1.98(1H,m), 2.28 (3H,s), 3.06–3.19(2H,m), 3.62(1H,dd,J=7.3,7.9 Hz), 3.91 (1H,dd,J=7.3,7.9 Hz), 4.13–4.21(1H,m), 4.62(1H,s), 7.07–7.42(4H,m); Mass spectrum (CI, m/z): 308(M$^+$+1); IR spectrum (KBr, $\nu_{max}$ cm$^{-1}$): 1695.

(b) 1-(α-Cyclopropylcarbonyl-2-fluorobenzyl-3-mercaptoazetidine hydrochloride

In a similar manner to that described in Example 1(b) except for the use of 3-acetylthio-1-(α-cyclopropylcarbonyl-2-fluorobenzyl)azetidine instead of 4-acetylthio-1-(α-cyclopropylcarbonyl-2-fluorobenzyl) piperidine, the reaction was effected, whereby the title compound was obtained as a white solid (amorphous) in a yield of 83%.

Mass spectrum (CI, m/z): 266 (M$^+$+1); IR spectrum (KBr, $\nu_{max}$ cm$^{-1}$): 1709; Anal.Calcd for C$_{14}$H$_{16}$FNOS.HCl.1/2H$_2$O:C,54.10;H,5.84;N,4.51; Found:C,53.95;H,5.68;N,4.45.

EXAMPLE 7

1-(α-Cyclopropylcarbonyl-2-fluorobenzyl)-4-mercaptomethylpiperidin hydrochloride (Exemplified Compound No. 113)

(a) 4-Acetylthiomethyl-1-(α-cyclopropylcarbonyl-2-fluorobenzyl)piperidine (Exemplified Compound No. 656)

In a similar manner to that described in Example 1(a) except for the use of 1-(α-cyclopropylcarbonyl-2-fluorobenzyl)-4-hydroxymethylpiperidine instead of 1-(α-cyclopropylcarbonyl-2-fluorobenzyl)-4-hydroxypiperidine, the reaction was effected, whereby the title compound was obtained as a brown oil in a yield of 51%.

NMR spectrum (CDCl$_3$, δ): 0.78–0.88(2H,m), 0.92–1.08 (2H,m), 1.28–1.50(3H,m), 1.65–1.90(3H,m), 2.05–2.15(1H, m), 2.20–2.30(1H,m), 2.30(3H,s), 2.80(2H,d,J=7 Hz), 2.82–2.85(1H,m), 2.98–3.02(1H,m), 4.58(1H,s), 7.05–7.45 (4H,m); Mass spectrum (CI, m/z): 350 (M$^+$+1).

(b) 1-(α-Cyclopropylcarbonyl-2-fluorobenzyl)-4-mercaptomethylpiperidine hydrochloride In a similar manner to that described in Example 1(b) except for the use of 4-acetylthiomethyl-1-(α-cyclopropylcarbonyl-2-fluorobenzyl)piperidine instead of 4-acetylthio-1-(α-cyclopropylcarbonyl-2-fluorobenzyl) piperidine, the reaction was effected, whereby the title compound was obtained as light brown crystals in a yield of 88%.

Melting point: 150–155° C.; Mass spectrum (CI, m/z): 308 (M$^+$+1); Anal.Calcd for C$_{17}$H$_{20}$FNOS.HCl.1/4H$_2$O:C,58.61;H,6.80;N,4.02; Found:C,58.70;H,6.85;N,3.98.

EXAMPLE 8

1-(α-Cyclopropylcarbonyl-2-fluorobenzyl)-3-mercaptomethylpiperidine hydrochloride (Exemplified Compound No. 175)

(a) 3-Acetylthiomethyl-1-(α-cyclopropylcarbonyl-2-fluorobenzyl)piperidine (Exemplified Compound No. 761)

In a similar manner to Example 1(a) except for the use of 1-(α-cyclopropylcarbonyl-2-fluorobenzyl)-3-hydroxymethylpiperidine instead of 1-(α-cyclopropylcarbonyl-2-fluorobenzyl)-4-hydroxypiperidine, the reaction was effected, whereby the title compound was obtained as a brown oil in a yield of 75%.

NMR spectrum (CDCl$_3$, δ): 0.81–0.88(2H,m), 0.94–1.07 (3H,m), 1.56–1.96(6H,m), 2.13–2.16(0.5H,m), 2.29(1.5H, s), 2.32(1.5H,s), 2.67–2.70(0.5H,m), 2.77–2.91(4H,m); 4.58 (0.5H,s), 4.59(0.5H,s), 7.06–7.17(2H,m), 7.27–7.38(2H,m); Mass spectrum (CI, m/z): 350 (M$^+$+1); IR spectrum (liquid membrane, $\nu_{max}$ cm$^{-1}$): 1695.

(b) 1-(α-Cyclopropylcarbonyl-2-fluorobenzyl)-3-mercaptomethylpiperidine hydrochloride In a similar manner to that described in Example 1(b) except for the use of 3-acetylthiomethyl-1-(α-cyclopropylcarbonyl-2-fluorobenzyl)piperidine instead of 4-acetylthio-1-(α-cyclopropylcarbonyl-2-fluorobenizyl) piperidine, the reaction was effected, whereby the title compound was obtained as a light brown solid (amorphous) in a yield of 75%.

Mass spectrum (CI, m/z): 308 (M$^+$+1); IR spectrum (KBr, $\nu_{max}$ cm$^{-1}$): 1712, 2504.

EXAMPLE 9

8-(α-Cyclopropylcarbonyl-2-fluorobenzyl)-3-mercapto-8-azabicyclo[3.2.1]octane hydrochloride (Exemplified Compound No. 268)

(a) 3-Acetylthio-8-(α-cyclopropylcarbonyl-2-fluorobenzyl)-8-azabicyclo[3.2.1]octane (Exemplified Compound No. 826)

In a similar manner to that described in Example 1(a) except for the use of Isomer A-1 (Compound of Preparation 8) of 8-(α-cyclopropylcarbonyl-2-fluorobenzyl)-3-hydroxy-8-azabicyclo[3.2.1]octane instead of 1-(α-cyclopropylcarbonyl-2-fluorobenzyl)-4-hydroxypiperidine, the reaction was effected, whereby the title compound (Isomer A-2) was obtained as white crystals in a yield of 23.7%. Similarly, the other isomer (Isomer B-2) of the title compound was obtained as a light yellow solid (amorphous) in a yield of 12.4% by using Isomer B-1 (Compound of Preparation 8). Isomers A-2 and B-2 exhibited retention times of 9.7 minutes and 10.0 minutes respectively as a result of high-performance liquid chromatography (column: TSK-GEL ODS-80TM, mobile phase: acetonitrile/11 mM KH$_2$PO$_4$=70/30, flow rate: 1.0 ml/min, temperature: 35° C.).

Isomer A-2

Melting point: 113 to 114° C.; NMR spectrum (CDCl$_3$, δ): 0.75–1.01(4H,m), 1.67–2.17(8H,m), 2.29(3H,s), 2.42–2.48 (1H,m), 3.09–3.14(1H,m), 3.24–3.30(1H,m), 3.71–3.81(1H, m), 4.65(1H,s), 7.03–7.72(4H,m); Mass spectrum (CI, m/z): 362 (M$^+$+1).

Isomer B-2

NMR spectrum (CDCl$_3$, δ): 0.76–1.01(4H,m), 1.60(1H, d,J=14.0 Hz), 1.70(1H,d,J=14.0 Hz), 1.84–2.04(3H,m), 2.05–2.17(1H,m), 2.29(3H,s), 2.39–2.50(2H,m), 2.50–2.58 (1H,m), 3.03–3.10(1H,m), 3.21–3.29(1H,m), 3.99(1H,t,J= 7.2 Hz), 4.62(1H,s), 7.03–7.73(4H,m); Mass spectrum (CI, m/z): 362 (M$^+$+1).

(b) 8-(α-Cyclopropylcarbonyl-2-fluorobenzyl)-3-mercapto-8-azabicyclo[3.2.1]octane hydrochloride In a similar manner to that described in Example 1(b) except for the use of Isomers A-2 and B-2 of 3-acetylthio-8-(α-cyclopropylcarbonyl-2-fluorobenzyl)-8-azabicyclo[3.2.1]octane in Example 9(a) instead of 4-acetylthio-1-(α-cyclopropylcarbonyl-2-fluorobenzyl)piperidine, the reaction was effected, whereby Isomers A-3 and B-3 of the title compound were obtained in yields of 61.1% and 99.2%, respectively. Isomers A-3 and B-3 exhibited the retention time of 10.0 minutes and 9.3 minutes, respectively, as a result of high-performance liquid chromatography (as measured under the conditions similar to those of Example 9(a)).

Isomer A-3

Appearance: Light yellow crystals; Melting point: 181 to 185° C.; NMR spectrum (CDCl$_3$, δ): 0.84–0.95(1H,m), 0.95–1.07(1H,m), 1.07–1.36(2H,m), 1.80–2.46(8H,m), 2.83–2.98(1H,m), 3.28–3.47(1H,m), 3.54(1H,s), 4.21(1H,s), 5.17(1H,s), 7.18–7.52(4H,m), 8.57(1H,s), 12.40–12.71(1H, m); Mass spectrum (CI, m/z): 320 (M$^+$+1).

Isomer B-3

Appearance: Light gray solid (amorphous); NMR spectrum (CDCl$_3$, δ): 0.84–0.93(1H,m), 0.95–1.05(1H,m), 1.15–1.32(2H,m), 1.72–2.05(3H,m), 2.00–2.45(2H,m), 2.55–2.65(1H,m), 2.76–2.86(1H,m), 3.55(1H,s), 3.70–3.80 (3H,m), 4.23(1H,s), 5.21(1H,s), 7.19–7.50(4H,m), 8.50–8.58(1H,m), 12.28–12.47(1H,m); Mass spectrum (CI, m/z): 320 (M$^+$+1).

EXAMPLE 10

(E)-1-(α-Cyclopropylcarbonyl-2-fluorobenzyl)-3-ethoxycarbonylmethylidene-4-mercaptopiperidine hydrochloride (Exemplified Compound No. 422)

(a) (E)-4-Acetylthio-1-(α-cyclopropylcarbonyl-2-fluorobenzyl)-3-ethoxycarbonylmethylidenepiperidine (Exemplified Compound No. 1022)

In 50 ml of anhydrous methylene chloride, 3.28 g (9.1 mmol) of 1-(α-cyclopropylcarbonyl-2-fluorobenzyl)-3-ethoxycarbonylmethylidene-4-hydroxypiperidine were dissolved, followed by the addition of 6.02 g (18.2 mmol) of carbon tetrabromide at room temperature. To the resulting mixture, 2.62 g (9.9 mmol) of triphenylphosphine were added in one portion and the resulting mixture was stirred at room temperature for one hour. After concentration of the reaction mixture, the residue was purified by chromatography on a silica gel column (eluting solvent: toluene/ethyl acetate=19/1), whereby 2.00 g (yield: 52.1%) of 4-bromo-1-(α-cyclopropylcarbonyl-2-fluoroenzyl)-3-ethoxycarbonylmethylidenepiperidine were obtained as a light yellow oil.

NMR spectrum(CDCl$_3$, δ): 0.75–0.88(2H,m), 0.97–1.11 (2H,m), 1.22,1.25(total 3H, each t,J=6.8 Hz,J=7.3 Hz), 2.05–3.00(6H,m), 4.11,4.13(total 2H, each q,J=6.8 Hz,J=7.3 Hz), 4.45,4.60(total 1H, each d,J=13.6 Hz,J=14.1 Hz), 4.77, 4.78(total 1H, each s), 5.90(1H,s), 7.05–7.43(4H,m); Mass spectrum (CI, m/z): 424 (M$^+$+1).

To 30 ml of anhydrous ethanol, 2.14 g (18.7 mmol) of potassium thioacetate and 1.98 g (4.7 mmol) of 4-bromo-1-(α-cyclopropylcarbonyl-2-fluorobenzyl)-3-ethoxycarbonylmethylidenepipridine, which had been obtained above, were added, followed by stirring at room temperature for 1 hour and then at 50° C. for 5 hours. The reaction mixture was filtered to remove the precipitated salt, followed by concentration. The residue was purified by chromatography on a silica gel column (eluting solvent: toluene/ethyl acetate=19/1), whereby 0.95 g (yield: 48.2%) of the title compound were obtained as a light yellow oil.

NMR spectrum(CDCl$_3$, δ): 0.78–0.90(2H,m), 0.99–1.10 (2H,m), 1.22,1.25(total 3H, each t,J=6.8 Hz,J=7.3 Hz), 1.82–1.94(1H,m), 2.13–2.28(2H,m), 2.30,2.31(total 3H, each s), 2.35–2.90(3H,m), 3.40(1H,br.s), 4.11,4.13(total 2H, each q,J=6.8 Hz,J=7.3 Hz), 4.25–4.40(1H,m), 4.75,4.77 (total 1H, each s), 5.93(1H,s), 7.08–7.38(4H,m); Mass spectrum(CI, m/z): 420 (M$^+$+1), 350.

(b) (E)-1-(α-cyclopropylcarbonyl-2-fluorobenzyl)-3-ethoxycarbonylmethylidene-4-mercaptopiperidine hydrochloride The reaction was effected in a similar manner to that described in Example 1(b) by using 0.57 g (1.3 mmol) of (E)-4-acetylthio-1-(α-cyclopropylcarbonyl-2-fluorobenzyl)-3-ethoxycarbonylmethylidenepiperidine, whereby 0.52 g (yield: 92%) of the title compound was obtained as light yellowish white crystals.

Melting point: 120 to 125° C.; NMR spectrum(CDCl$_3$, δ): 0.80–0.93(1H,m), 0.94–1.06(1H,m), 1.23(3H,t,J=7.3 Hz), 1.70–2.20(5H,m), 2.80–3.06, 3.11–3.39(total 1H, each m), 3.45–3.80(1H,m), 3.90–4.25(2H,m), 4.20(2H,q,J=7.3 Hz), 4.58,5.05(total 1H, each m), 5.49(1H,s), 6.25(1H,s), 7.15–8.10(4H,m); Mass spectrum(CI, m/z): 378(M$^+$+1), 308; IR spectrum(KBr, ν$_{max}$cm$^{-1}$): 1712.

EXAMPLE 11

(E)-1-(α-Cyclopropylcarbonyl-2-fluorobenzyl)-3-carboxymethylidene-4-mercaptopiperidine hydrochloride (Exemplified Compound No. 464)

In a mixed solvent of 15 ml of acetic acid and 10 ml of concentrated hydrochloric acid, 0.44 g (1.1 mmol) of (E)-1-(α-cyclopropylcarbonyl-2-fluorobenzyl)-3-ethoxycarbonylmethylidene-4-mercaptopiperidine were dissolved and the resulting solution was allowed to stand for 12 days at room temperature in a dark place. The reaction mixture was concentrated to dryness, followed by crystallization from ethyl ether. The crystals collected by filtration were purified by chromatography on a silica gel column (eluting solvent: chloroform/methanol=30/1), whereby 0.12 g (yield 27%) of the title compound were obtained as light yellowish white crystals.

Melting point: 109 to 111° C.; NMR spectrum (CDCl$_3$, δ): 0.74–0.92(1H,m), 1.00–1.14(1H,m), 1.62–1.75(1H,m), 1.76–1.90(1H,m), 1.94–2.08(2H,m), 2.20–2.39(1H,m), 2.50–2.70(2H,m), 2.90–3.03, 3.08–3.18 (total 1H, each m), 3.41–3.80(3H,m), 4.11–4.28(1H,m), 4.90,5.03(total 1H, each d,J=17.6 Hz), 5.98,6.12(total 1H, each s), 7.10–7.55 (4H,m); Mass spectrum (CI, m/z): 350(M$^+$+1), 280; IR spectrum (KBr, ν$_{max}$cm$^{-1}$): 1712.

EXAMPLE 12

(Z)-1-(α-Cyclopropylcarbonyl-2-fluorobenzyl)-3-carboxymethylidene-4-mercaptopiperidine trifluoroacetate (Exemplified Compound No. 464)

In 60 ml of a (1:1) mixed solvent of methanol and acetonitrile, 0.50 g (1.3 mmol) of (E)-1-(α-cylopropylcarbonyl-2-fluorobenzyl)-3-carboxymethylidene-4-mercaptopiperidine hydrochloride and 0.05 ml of dimethyl disulfide were dissolved, followed by exposure to light for 90 minutes under cooling by using a low-pressure mercury lamp of 32 W. After the completion of the reaction, the reaction mixture was concentrated by evaporation under reduced pressure. The residue was subjected to high-performance liquid chromatography (column: TSK-GEL ODS-80TS, mobile phase; acetonitrile/water=3/7 (containing 0.016% of trifluoroacetic acid), temperature: room temperature), whereby two diastereomers of the title compound, that is, 14.0 mg (Isomer A) and 13.5 mg (Isomer B) were obtained, each as white powder (amorphous). The retention times of Isomer A and Isomer B in high-performance liquid chromatography (column: Inertsil ODS-2, mobile phase: acetonitrile/water=20/80 (containing 0.02% of trifluoroacetic acid), temperature: 27° C., flow rate: 1.5 ml/min) were 16.5 minutes and 18.5 minutes, respectively.

Isomer A

NMR spectrum ($CD_3CN$, δ): 0.80–1.10(4H,m), 1.82–1.89 (1H,m), 1.92–2.02(1H,m), 2.26–2.46(2H,m), 3.11–3.29(2H, m), 3.46(1H,d,J=13.6 Hz), 3.81(1H,d,J=14.2 Hz), 5.26(1H, s), 5.38(1H,s), 5.73(1H,s), 7.27–7.59(4H,m); Mass spectrum (CI, m/z): 350($M^+$+1), 280.

Isomer B

NMR spectrum ($CD_3CN$, δ): 0.80–1.11(4H,m), 1.79–1.88 (1H,m), 1.95–2.04(1H,m), 2.28–2.43(2H,m), 2.86–3.01(1H, m), 3.03–3.12(1H,m), 3.52(1H,d,J=12.8 Hz), 3.87(1H,d,J=12.8 Hz), 5.24(1H,s), 5.29(1H,s), 5.68(1H,s), 7.25–7.56(4H, m); Mass spectrum(CI, m/z): 350($M^+$+1), 280.

EXAMPLE 13

(E)-4-Acetylthio-1-(2-chloro-α-methoxycarbonylbenzyl)-3-ethoxycarbonylmethylidenepiperidine (Exemplified Compound No. 1039)

In a similar manner to Example 10(a) except for the use of (E)-1-(2-chloro-α-methoxycarbonylbenzyl)-3-ethoxycarbonylmethylidene-4-hdyroxypiperidine instead of (E)-1-(α-cyclopropylcarbonyl-2-fluorobenzyl)-3-ethoxycarbonylmethylidene-4-hydroxypiperidine, the reaction was effected, whereby the title compound was obtained as a light reddish brown oil in a yield of 35.3%.

NMR spectrum ($CDCl_3$, δ): 1.21, 1.23(total 3H, each t, J=7.3 Hz), 1.75–1.92(1H,m), 2.15–2.30(1H,m), 2.32(3H,s), 2.52–2.85(2H,m), 3.48(0.5H,d,J=13.9 Hz), 3.60(0.5H,d,J=13.9 Hz), 3.71,3.72(total 3H, each s), 4.05–4.14(2.5H,m), 4.25(0.5H,d,J=13.9 Hz), 4.31–4.44(1H,m), 4.83,4.85(total 1H, each s), 5.96(1H,s), 7.15–7.70(4H,m); Mass spectrum (CI, m/z): 426 ($M^+$+1).

EXAMPLE 14

(E)-1-(2-Chloro-α-methoxycarbonylbenzyl)-3-carboxymethylidene-4-mercaptopiperidine hydrochloride (Exemplified Compound No. 477)

In a similar manner to Example 11 except for the use of (E)-4-acetylthio-1-(2-chloro-α-methoxycarbonylbenzyl)-3-ethoxycarbonylmethylidenepiperidine instead of (E)-1-(α-cyclopropylcarbonyl-2-fluorobenzyl)-3-ethoxycarbonylmethylidene-4-mercaptopiperidine hydrochloride, the reaction was effected, whereby the title compound was obtained as a light brown oil in a yield of 32.9%.

Melting point: 122 to 130° C.; NMR spectrum ($CDCl_3$, δ): 1.90–2.05(2H,m), 2.70–2.83(1H,m), 3.49–3.60(1H,m), 3.80,3.82 (total 3H, each s), 3.95–4.02(1H,m), 4.08–4.15 (1H,m), 4.70–4.78(1H,m), 5.52(1H,s), 6.51(1H,s), 7.35–7.60(4H,m), 8.03–8.15(1H,m); Mass spectrum (CI, m/z): 338 ($M^+$+1–18($H_2O$)).

The title compound was treated as in Example 12, whereby Isomer Z of the title compound can be prepared.

EXAMPLE 15

(E)-1-(α-Cyclopropylcarbonyl-2-fluorobenzyl)-3-(N, N-dimethylcarbamoyl)methylidene-4-mercaptopiperidine hydrochloride (Exemplified Compound No. 486)

(a) (E)-4-Acetylthio-1-(α-cyclopropylcarbonyl-2-fluorobenzyl)-3-(N,N-dimethylcarbamoyl) methylidenepiperidine (Exemplified Compound No. 1132)

In a similar manner to Example 10(a) except for the use of (E)-1-(α-cyclopropylcarbonyl-2-fluorobenzyl)-4-hydroxy-3-(N,N-dimethylcarbamoyl)methylidenepiperidine instead of (E)-1-(α-cyclopropylcarbonyl-2-fluorobenzyl)-3-ethoxycarbonylmethylidene-4-hydroxypiperidine, the reaction was effected, whereby the title compound was obtained as a light brown oil in a yield of 24.9%.

NMR spectrum ($CDCl_3$, δ): 0.76–0.91(2H,m), 0.95–1.09 (2H,m), 1.70–1.94(2H,m), 2.15–2.50(5H,m), 2.70–3.30(8H, m), 3.55–3.80(1H,m), 4.28–4.40(1H,m), 4.68,4.75 (total 1H, each s), 6.14(1H,s), 7.05–7.80(4H,m); Mass spectrum (CI, m/z): 419 ($M^+$+1).

(b) (E)-1-(α-Cyclopropylcarbonyl-2-fluorobenzyl)-3-(N,N-dimethylcarbamoyl)methylidene-4-mercaptopiperidine hydrochloride In a similar manner to Example 1(b) except for the use of (E)-4-acetylthio-1-(α-cyclopropylcarbonyl-2-fluorobenzyl)-3-(N,N-dimethylcarbamoyl) methylidenepiperidine instead of (E)-4-acetylthio-1-(α-cyclopropylcarbonyl-2-fluorobenzyl)-3-ethoxycarbonylmethylidenepiperidine, the reaction was effected, whereby the title compound was obtained as light brown crystals in a yield of 79.1%.

Melting point: 106 to 111° C.; NMR spectrum ($CDCl_3$, δ): 0.75–1.55(4H,m), 1.60–2.50(4H,m), 2.75–3.35(7H,m), 3.40–4.80(4H,m), 5.53(1H,s), 6.31,6.60(total 1H, each s), 7.10–7.90(4H,m), 12.9(1H,brs); Mass spectrum (CI, m/z): 377($M^+$+1).

EXAMPLE 16

(E)-1-(α-Cyclopropylcarbonyl-2-fluorobenzyl)-3-(N-methylcarbamoyl)methylidene-4-mercaptopiperidine hydrochloride (Exemplified Compound No. 508)

(a) (E)-4-Acetylthio-1-(α-cyclopropylcarbonyl-2-fluorobenzyl)-3-(N-methylcarbamoyl) methylidenepiperidine (Exemplified Compound No. 1168)

In a similar manner to Example 10(a) except for the use of (E)-1-(α-cyclopropylcarbonyl-2-fluorobenzyl)-4-hydroxy-3-(N-methylcarbamoyl)methylidenepiperidine instead of (E)-1-(α-cyclopropylcarbonyl-2-fluorobenzyl)-3-ethoxycarbonylmethylidene-4-hydroxypiperidine, the reaction was effected, whereby the title compound was obtained as light yellow crystals in a yield of 13.5%.

NMR spectrum ($CDCl_3$, δ): 0.75–0.98(2H,m), 0.98–1.13 (2H,m), 1.50–1.72(1H,m), 1.72–1.90(1H,m), 1.91–2.10(1H, m), 2.10–2.45(5H,m), 2.55–3.05(5H,m), 3.05–3.35(1H,m), 3.85–4.10(1H,m), 4.26,4.28 (total 1H, each s), 4.79,4.83 (total 1H, each s), 5.90(1H,s), 6.05(1H,br.s), 7.05–7.50(4H, m); Mass spectrum (CI, m/z): 405($M^+$+1).

(b) (E)-1-(α-Cyclopropylcarbonyl-2-fluorobenzyl)-3-(N-methylcarbamoyl)methylidene-4-mercaptopiperidine hydrochloride In a similar manner to Example 1(b) except for the use of (E)-4-acetylthio-1-(α-cyclopropylcarbonyl-2-fluorobenzyl)-3-(N-methylcarbamoyl)-methylidenepiperidine instead of (E)-4-acetylthio-1-(α-cyclopropylcarbonyl-2-fluorobenzyl)-3-ethoxycarbonylmethylidenepiperidine, the reaction was effected, whereby the title compound was obtained as light brown crystals in a yield of 42.5%.

Melting point: 133 to 141° C.; NMR spectrum (CDCl$_3$, δ): 0.80–1.15(2H,m), 1.13–1.40(2H,m), 1.60–2.08(5H,m), 2.50–3.05(3H,m), 3.06–4.50(5H,m), 5.41,5.42 (total 1H, each s), 6.09,6.18(total 1H, each s), 7.15–7.98(4H,m), 8.61, 8.81 (total 1H, each br.s), 12.9 (1H,br.s); Mass spectrum (CI, m/z): 363(M$^+$+1).

EXAMPLE 17

1-(α-Cyclopropylcarbonyl-2-fluorobenzyl)-3-ethylidene-4-mercaptopiperidine hydrochloride (Exemplified Compound No. 336)

(a) 4-Acetylthio-1-(α-cyclopropylcarbonyl-2-fluorobenzyl)-3-methylidenepiperidine (Exemplified Compound No. 890)

In a similar manner to that described in Example 1(a) except for the use of 1-(α-cyclopropylcarbonyl-2-fluorobenzyl)-3-ethylidene-4-hydroxypiperidine instead of 1-(α-cyclopropylcarbonyl-2-fluorobenzyl)-4-hydroxypiperidine, the reaction was effected, whereby the title compound was obtained as a brown oil in a yield of 44.0%.

NMR spectrum (CDCl$_3$, δ): 0.80–0.89(2H,m), 0.93–1.06 (2H,m), 1.37–1.39(3H,m), 2.08–2.23(2H,m), 2.24–2.26(1H, m), 2.27(1.5H,s), 2.28(1.5H,s), 2.41–2.67(2H,m), 2.89–3.13 (2H,m), 4.00–4.03(1H,m), 4.69(0.5H,s), 4.70(0.5H,s), 5.75 (1H,br.s), 7.07–7.18(2H,m), 7.28–7.33(1H,m), 7.43–7.47 (1H,m); Mass spectrum (CI, m/z): 362 (M$^+$+1).

(b) 1-(α-Cyclopropylcarbonyl-2-fluorobenzyl)-3-ethylidene-4-mercaptopiperidine hydrochloride In a similar manner to Example 1(b) except for the use of 3-acetylthio-1-(α-cyclopropylcarbonyl-2-fluorobenzyl)-3-methylidenepiperidine instead of 4-acetylthio-1-(α-cyclopropylcarbonyl-2-fluorobenzyl)piperidine, the reaction was effected, whereby the title compound was obtained as a light brown solid (amorphous) in a yield of 85.0%.

Mass spectrum (CI, m/z): 320 (M$^+$+1); IR spectrum (KBr, ν$_{max}$ cm$^{-1}$): 1713, 2424.

EXAMPLE 18

4-Butyrylthio-1-(α-cyclopropylcarbonyl-2-fluorobenzyl)piperidine (Exemplified Compound No. 591)

In 5 ml of dichloromethane, 0.50 g (1.5 mmol) of 1-(α-cyclopropylcarbonyl-2-fluorobenzyl)-4-mercaptopiperidine hydrochloride were dissolved, followed by the addition of 0.3 g (3 mmol) of triethylamine. To the resulting mixture, a solution of 0.16 g (1.5 mmol) of butyryl chloride in 1 ml of dichloromethane was added dropwise under ice cooling and the resulting mixture was stirred at room temperature for 1 hour. Water was added to the reaction mixture, followed by extraction with dichloromethane. The extract was dried over anhydrous sodium sulfate. The solvent was concentrated by evaporation under reduced pressure and the residue was subjected to chromatography on a silica gel column (eluting solvent: toluene/ethyl acetate=30/1), whereby 0.32 g (yield: 58%) of the title compound was obtained as white crystals.

Melting point: 97 to 98° C.; NMR spectrum (CDCl$_3$, δ): 0.76–0.86(2H,m), 0.91(3H,t,J=7.3 Hz), 0.95–1.03(2H,m), 1.60–1.79(4H,m), 1.88–1.98(2H,m), 2.14–2.20(2H,m), 2.30–2.34(1H,m), 2.46(2H,t,J=7.3 Hz), 2.70–2.78(1H,m), 2.79–2.85(1H,m), 3.38–3.48(1H,m), 4.61(1H,s), 7.05–7.34 (4H,m); Mass spectrum (CI, m/z): 364 (M$^+$+1); IR spectrum (KBr, ν$_{max}$cm$^{-1}$): 1685.

EXAMPLES 19 to 24

The reaction was effected in a similar manner to that described in Example 18 by using various acid halides or acid anhydrides instead of butyryl chloride, whereby compounds of Examples 19 to 24 were obtained.

EXAMPLE 19

1-(α-Cyclopropylcarbonyl-2-fluorobenzyl)-4-pivaloylthiopiperidine (Exemplified Compound No. 594)

Acid halide or acid anhydride employed: pivaloyl chloride; Yield: 72%; Appearance: Light brown crystals; Melting point: 88 to 89° C.; NMR spectrum (CDCl$_3$, δ): 0.72–0.90 (2H,m), 0.92–1.08(2H,m), 1.20(9H,s), 1.60–1.82(2H,m), 1.83–2.00(2H,m), 2.08–2.38(3H,m), 2.70–2.90(2H,m), 3.28–3.42(1H,m), 4.62(1H,s), 7.06–7.36(4H,m); Mass spectrum (CI, m/z): 378 (M$^+$+1); IR spectrum (KBr, ν$_{max}$cm$^{-1}$): 1677.

EXAMPLE 20

1-(α-Cyclopropylcarbonyl-2-fluorobenzyl)-4-hexanoylthiopiperidine (Exemplified Compound No. 595)

Acid halide or acid anhydride employed: hexanoyl chloride; Yield: 56%; Appearance: White crystals; Melting point: 64 to 65° C.; NMR spectrum (CDCl$_3$, δ): 0.79–0.84(2H,m), 0.88(3H,t,J=7.3 Hz), 0.95–1.05(2H,m), 1.26–1.31(4H,m), 1.60–1.83(4H,m), 1.85–2.02(2H,m), 2.12–2.27(2H,m), 2.32–2.37(1H,m), 2.49(2H,t,J=7.3 Hz), 2.72–2.79(2H,m), 3.40–3.48(1H,m), 4.63(1H,s), 7.06–7.38(4H,m); Mass spectrum (CI, m/z): 392 (M$^+$+1); IR spectrum (KBr, ν$_{max}$cm$^{-1}$): 1690.

EXAMPLE 21

1-(α-Cyclopropylcarbonyl-2-fluorobenzyl)-4-palmitoylthiopiperidine (Exemplified Compound No. 597)

Acid halide or acid anhydride employed: palmitoyl chloride Yield: 73%; Appearance: White crystals; Melting point: 71 to 72° C.; NMR spectrum (CDCl$_3$, δ): 0.77–0.84(2H,m), 0.88(3H,t,J=6.8 Hz), 0.94–1.06(2H,m), 1.11–1.34(24H,m), 1.55–1.82(4H,m), 1.87–2.00(2H,m), 2.10–2.23(2H,m), 2.27–2.38(1H,m), 2.48(2H,t,J=7.6 Hz), 2.70–2.89(2H,m), 3.39–3.49(1H,m), 4.62(1H,s), 7.07–7.37(4H,m); Mass spectrum (CI, m/z): 532 (M$^+$+1).

EXAMPLE 22

1-(α-Cyclopropylcarbonyl-2-fluorobenzyl)-4-stearoylthiopiperidine (Exemplified Compound No. 598)

Acid halide or acid anhydride employed: stearoyl chloride Yield: 60.1%; Appearance: White crystals; Melting point: 74 to 75° C.; NMR spectrum (CDCl$_3$, δ): 0.77–0.85(2H,m), 0.88(3H,t,J=7.1 Hz), 0.94–1.06(2H,m), 1.14–1.34(28H,m), 1.55–1.85(4H,m), 1.88–2.00(2H,m), 2.09–2.24(2H,m), 2.26–2.38(1H,m), 2.48(2H,t,J=7.3 Hz), 2.70–2.90(2H,m), 3.39–3.49(1H,m), 4.63(1H,s), 7.07–7.36(4H,m); Mass spectrum (CI, m/z): 560 (M$^+$+1).

EXAMPLE 23

1-(α-Cyclopropylcarbonyl-2-fluorobenzyl)-4-oleoylthiopiperidine (Exemplified Compound No. 600)

Acid halide or acid anhydride employed: oleoyl chloride Yield: 45.0%; Appearance: White crystals; Melting point: 35 to 37° C.; NMR spectrum (CDCl$_3$, δ): 0.77–0.85(2H,m), 0.88(3H,t,J=6.8 Hz), 0.94–1.07(2H,m), 1.18–1.38(20H,m), 1.56–1.82(4H,m), 1.88–2.07(6H,m), 2.10–2.23(2H,m), 2.27–2.38(1H,m), 2.48(2H,t,J=7.2 Hz), 2.70–2.89(2H,m), 3.39–3.49(1H,m), 4.63(1H,s), 5.27–5.42(2H,m), 7.07–7.37 (4H,m); Mass spectrum (CI, m/z): 558 (M$^+$+1).

EXAMPLE 24

4-Benzoylthio-1-(α-cyclopropylcarbonyl-2-fluorobenzyl)piperidine (Exemplified Compound No. 601)

Acid halide or acid anhydride to be employed: benzoyl chloride. Yield: 39.9%; Appearance: White crystals; Melting point: 55 to 59° C.; NMR spectrum (CDCl$_3$, δ): 0.78–0.92 (2H,m), 0.96–1.12(2H,m), 1.70–2.00(2H,m), 2.00–2.15(2H,m), 2.15–2.32(2H,m), 2.32–2.51(1H,m), 2.74–2.98(2H,m), 3.59–3.74(1H,m), 4.67(1H,s), 7.12–7.93(9H,m); Mass spectrum (CI, m/z): 398 (M$^+$+1).

EXAMPLES 25 to 28

In a similar manner to that described in Example 18 except for the use of 1-(2-fluoro-α-methoxycarbonylbenzyl)-4-mercaptopiperidine hydrochloride instead of 1-(α-cyclopropylcarbonyl-2-fluorobenzyl)-4-mercaptopiperidine hydrochloride and various acid halides or acid anhydrides instead of butyryl chloride, compounds of Examples 25 to 28 were obtained.

EXAMPLE 25

1-(2-Fluoro-α-methoxycarbonylbenzyl)-4-palmitoylthiopiperidine (Exemplified Compound No. 616)

Acid halide or acid anhydride to be employed: palmitoyl chloride; Yield: 34.7%; Appearance: White crystals; Melting point: 44 to 47° C.; NMR spectrum (CDCl$_3$, δ): 0.88(3H,t, J=6.8 Hz), 1.14–1.34(24H,m), 1.55–1.78(4H,m), 1.87–2.00 (2H,m), 2.22–2.45(2H,m), 2.49(2H,t,J=7.5 Hz), 2.72–2.87 (2H,m), 3.39–3.50(1H,m), 3.70(3H,s), 4.53(1H,s), 7.04–7.49(4H,m); Mass spectrum (CI, m/z): 522 (M$^+$+1).

EXAMPLE 26

1-(2-Fluoro-α-methoxycarbonylbenzyl)-4-stearoylthiopiperidine (Exemplified Compound No. 617)

Acid halide or acid anhydride to be employed: stearoyl chloride. Yield: 56.4%; Appearance: White crystals; Melting point: 50 to 52° C.; NMR spectrum (CDCl$_3$, δ): 0.88(3H,t, J=6.8 Hz), 1.15–1.35(28H,m), 1.57–1.81(4H,m), 1.86–1.99 (2H,m), 2.23–2.45(2H,m), 2.49(2H,t,J=7.6 Hz), 2.74–2.88 (2H,m), 3.40–3.50(1H,m), 3.71(3H,s), 4.53(1H,s), 7.04–7.48(4H,m); Mass spectrum (CI, m/z): 550 (M$^+$+1).

EXAMPLE 27

1-(2-Fluoro-α-methoxycarbonylbenzyl)-4-oleoylthiopiperidine (Exemplified Compound No. 619)

Acid halide or acid anhydride to be employed: oleoyl chloride. Yield: 70.4%; Appearance: Light yellow oil; NMR spectrum (CDCl$_3$, δ): 0.88(3H,t,J=6.8 Hz), 1.15–1.38(20H, m), 1.58–1.80(4H,m), 1.88–2.09(6H,m), 2.22–2.45(2H,m), 2.49(2H,t,J=7.6 Hz), 2.74–2.85(2H,m), 3.39–3.49(1H,m), 3.70(3H,s), 4.53(1H,s), 5.27–5.42(2H,m), 7.04–7.49(4H, m); Mass spectrum (CI, m/z): 548 (M$^+$+1).

EXAMPLE 28

4-Benzoylthio-1-(2-fluoro-α-methoxycarbonylbenzyl)piperidine (Exemplified Compound No. 620)

Acid halide or acid anhydride to be employed: benzoyl chloride. Yield: 71.8%; Appearance: yellow oil; NMR spectrum (CDCl$_3$, δ): 1.75–1.91(2H,m), 1.99–2.10(2H,m), 2.34 (1H,t,J=9.6 Hz), 2.45(1H,t,J=9.6 Hz), 2.81–2.91(2H,m), 3.62–3.70(1H,m), 3.72(3H,s), 4.56(1H,s), 7.05–7.94(9H, m); Mass spectrum (CI, m/z): 388 (M$^+$+1).

Preparation 1

1-(α-Cyclopropylcarbonyl-2-fluorobenzyl)-4-hydroxypiperidine

In 30 ml of dimethylformamide (DMF), 3.13 g (31 mmol) of 4-hydroxypiperidine were dissolved, followed by the addition of 7.94 g (31 mmol) of α-cyclopropylcarbonyl-2-fluorobenzylbromide and 4.7 g (34 mmol) of potassium carbonate. The resulting mixture was stirred at room temperature for 2 hours. Water was added to the reaction mixture, followed by extraction with toluene. The resulting organic layer was dried over anhydrous sodium sulfate. The solvent was concentrated by evaporation under reduced pressure. The residue was purified by chromatography on a silica gel column (eluting solvent: chloroform/methanol=19/1), whereby 8.00 g of the title compound were obtained as a brown oil (yield: 93%).

NMR spectrum (CDCl$_3$, δ): 0.79–0.87(2H,m), 0.98–1.04 (2H,m), 1.50–1.72(2H,m), 1.82–1.98(2H,m), 2.02–2.15(1H, m), 2.18–2.30(2H,m), 2.70–2.90(2H,m), 3.60–3.74(1H,m), 4.62(1H,s), 7.05–7.45(4H,m); Mass spectrum (CI, m/z): 278 (M$^+$+1).

Preparation 2

1-(2-Chloro-α-methoxycarbonylbenzyl)-4-hydroxypiperidine

In a similar manner to that described in Preparation 1 except for the use of 2-chloro-α-methoxycarbonylbenzylbromide instead of α-cyclopropylcarbonyl-2-fluorobenzylbromide, the reaction was effected, whereby the title compound was obtained as a colorless oil in a yield of 95%.

NMR spectrum (CDCl$_3$, δ): 1.55–1.70(2H,m), 1.80–2.00 (2H,m), 2.22–2.45(2H,m), 2.65–2.82(1H,m), 2.83–2.98(1H, m), 3.70(3H,s), 3.72–3.80(1H,m), 4.70(1H,s), 7.70(4H,m); Mass spectrum (CI, m/z): 284 (M$^+$+1).

Preparation 3

1-(α-Cyclopropylcarbonyl-2-fluorobenzyl)-3-hydroxypiperidine

In a similar manner to that described in Preparation 1 except for the use of 3-hydroxypiperidine instead of 4-hydroxypiperidine, the reaction was effected, whereby the title compound was obtained as a brown oil in a substantially quantitative yield.

NMR spectrum (CDCl$_3$, δ): 0.75–0.95(2H,m), 1.00–1.10 (2H,m), 1.45–1.68(3H,m), 1.72–1.95(1H,m), 2.02–2.20(1H, m), 2.30–2.70(4H,m), 3.80–3.90(1H,m), 4.72(1H,s), 7.05–7.45(4H,m); Mass spectrum (CI, m/z): 278 (M$^+$+1).

Preparation 4

1-(α-Cyclopropylcarbonyl-2-fluorobenzyl)-3-hydroxypyrrolidine

In a similar manner to that described in Preparation 1 except for the use of 3-hydroxypyrrolidine instead of 4-hydroxypiperidine, the reaction was effected, whereby the title compound was obtained as a yellow oil in a yield of 97%.

NMR spectrum (CDCl$_3$, δ): 0.79–0.90(2H,m), 1.00–1.03 (2H,m), 1.70–1.90(1H,m), 2.02–2.20(2H,m), 2.41–3.08(5H, m), 4.28–4.40(1H,m), 4.71,4.72(total 1H, each s) 7.07–7.46 (4H,m); Mass spectrum (CI, m/z): 264 (M$^+$+1).

Preparation 5

1-(α-Cyclopropylcarbonyl-2-fluorobenzyl)-3-hydroxyazetidine

In a similar manner to that described in Preparation 1 except for the use of 3-hydroxyazetidine instead of 4-hydroxypiperidine, the reaction was effected, whereby the title compound was obtained as white crystals in a yield of 66%.

NMR spectrum (CDCl$_3$, δ): 0.69–0.88(2H,m), 0.90–1.07 (2H,m), 1.87–1.96(1H,m), 2.94–3.03(2H,m), 3.17(1H,br.s), 3.44(1H,dd,J=6.1,6.7 Hz), 3.83(1H,dd,J=6.7,7.3 Hz), 4.45–4.53(1H,m), 4.62(1H,s), 7.07–7.38(4H,m); Mass spectrum (CI, m/z): 250 (M$^+$+1).

Preparation 6

1-(α-Cyclopropylcarbonyl-2-fluorobenzyl)-4-hydroxymethylpiperidine

In a similar manner to that described in Preparation 1 except for the use of 4-hydroxymethylpiperidine instead of 4-hydroxypiperidine, the reaction was effected, whereby the title compound was obtained as a brown oil in a substantially quantitative yield.

NMR spectrum (CDCl$_3$, δ): 0.75–0.90(2H,m), 0.92–1.08 (2H,m), 1.28–1.50(3H,m), 1.65–1.80(2H,m), 1.85–1.95(1H, m), 2.05–2.18(1H,m), 2.19–2.30(1H,m), 2.80–2.90(1H,m), 3.00–3.10(1H,m), 3.50(2H,d,J=6 Hz), 4.62(1H,s), 7.05–7.45 (4H,m); Mass spectrum (CI, m/z): 292 (M$^+$+1).

Preparation 7

1-(α-Cyclopropylcarbonyl-2-fluorobenzyl)-3-hydroxymethylpiperidine

In a similar manner to that described in Preparation 1 except for the use of 3-hydroxymethylpiperidine instead of 4-hydroxypiperidine, the reaction was effected, whereby the title compound was obtained as a light yellow oil in a substantially quantitative yield. NMR spectrum (CDCl$_3$, δ): 0.79–0.86(2H,m), 0.95–1.05(2H,m), 1.16–1.23(1H,m), 1.52–1.85(4H,m), 2.09–2.33(4H,m), 2.56–2.73(2H,m), 3.56–3.70(2H,m), 4.60(0.5H,s), 4.66(0.5H,s), 7.05–7.18 (2H,m), 7.25–7.41(2H,m); Mass spectrum (CI, m/z): 292 (M$^+$+1).

Preparation 8

8-(α-Cyclopropylcarbonyl-2-fluorobenzyl)-3-hydroxy-8-azabicyclo[3.2.1]octane

In a similar manner to that described in Preparation 1 except for the use of 3-hydroxy-8-azabicyclo[3.2.1]octane (exo-endo isomer mixture) instead of 4-hydroxypiperidine, the reaction was effected. By separation through chromatography on a silica gel column (eluting solvent: toluene/ethyl acetate=100/3), two isomers of the title compound, that is, Isomer A-1 and Isomer B-1 were obtained in a yield of 45.2% and 24.6%, respectively. As a result of high-performance liquid chromatography (column: TSK-GEL ODS-80TM, mobile phase: acetonitrile/12 mM KH$_2$PO$_4$= 45/55, temperature: 35° C., flow rate: 1.0 ml/min), Isomer A-1 and Isomer B-1showed retention time of 4.0 minutes and 4.3 minutes, respectively.

Isomer A-1

Appearance: Light yellow solid; NMR spectrum (CDCl$_3$, δ): 0.68–1.06(4H,m), 1.35(1H,s), 1.62 (1H,d,J=13.9 Hz), 1.72(1H,d,J=13.9 Hz), 1.82–2.32(6H,m), 2.39–2.54(1H,m), 3.05(1H,s), 3.22(1H,s), 4.13(1H,s), 4.64(1H,s), 6.95–7.80 (4H,m); Mass spectrum (CI, m/z): 304 (M$^+$+1).

Isomer B-1

Appearance: Light yellow oil; NMR spectrum (CDCl$_3$, δ): 0.68–1.08(4H,m), 1.25(1H,s), 1.46–2.35(8H,m), 2.38–2.54(1H,m), 3.18(1H,s), 3.26(1H,s), 3.89–4.05(1H,m), 4.72(1H,s), 6.96–7.95(4H,m); Mass spectrum (CI, m/z): 304 (M$^+$+1).

Preparation 9

(E)-1-(α-Cyclopropylcarbonyl-2-fluorobenzyl)-3-ethoxycarbonylmethylidene-4-hydroxypiperidine (a) 3-Ethoxycarbonylmethylidene-1-triphenylmethyl-4-piperidone To a solution of 10.6 g (65.1 mmol) of 4-piperidone monohydrate hydrochloride and 20.0 g (198 mmol) of triethylamine in 150 ml of dimethylformamide, 18.1 g (65.1 mmol) of chlorotriphenylmethane were added at 60° C. in portions under stirring, followed by stirring for further 5 hours at the same temperature. After cooling, the triethylamine hydrochloride thus precipitated was filtered off and the filtrate was concentrated by evaporation under reduced pressure. To the residue, 150 ml of water were added and the resulting mixture was extracted with 300 ml of ethyl acetate. The organic layer was washed with saturated saline and then dried over anhydrous magnesium sulfate. The solvent was concentrated by evaporation under reduced pressure, whereby 23.0 g (yield: 98.3%) of 1-triphenylmethyl-4-piperidone were obtained.

A solution of 23.0 g of the resulting product and 4.63 g (65.0 mmol) of pyrrolidine in 300 ml of benzene was subjected to azeotropic dehydration for 2 hours under heating and reflux by using water separator. To the residue, a solution of 6.63 g (65.0 mmol) of ethyl glyoxylate (polymer type) in 50 ml of benzene was added, followed by azeotropic dehydration again for 90 minutes under heating and reflux.

After cooling, 200 ml of water were added to wash the residue therewith. The organic layer was dried over anhydrous magnesium sulfate. The solvent was concentrated by evaporation under reduced pressure and the residue was purified by chromatography on a silica gel column (eluting solvent: toluene/ethyl acetate=19/1), whereby 16.6 g (yield: 60.2%) of the title compound were obtained as a light yellow oil.

NMR spectrum (CDCl$_3$, δ): 1.15(3H,t,J=6.3 Hz), 2.57–2.68 (2H, m), 2.72–2.81(2H,m), 3.61–3.79(2H,m), 4.08(2H,q,J= 6.3 Hz), 6.55(1H,s), 7.15–7.60(15H,m); Mass spectrum (CI, m/z): 426 (M$^+$+1).

(b) (E)-1-(α-Cyclopropylcarbonyl-2-fluorobenzyl)-3-ethoxycarbonylmethylidene-4-hydroxypiperidine To a solution of 16.6 g (39.1 mmol) of 3-ethoxycarbonylmethylidene-1-triphenylmethyl-4-piperidone in 150 ml of methanol, 1.48 g (39.1 mmol) of sodium borohydride were added in portions under ice cooling, followed by stirring at room temperature for 1 hour. After the reaction mixture was concentrated by evaporation under reduced pressure, 50 ml of water and 150 ml of ethyl acetate were added to the concentrate for extraction. The organic layer was washed with saturated saline and dried over anhydrous magnesium sulfate. The solvent was then distilled off under reduced pressure, whereby 16.8 g (yield: 100%) of 3-ethoxycarbonylmethylidene-4-hydroxypiperidine were obtained as a brown oil.

To the resulting product, 200 ml of tetrahydrofuran and 6.70 g (35.2 mmol) of paratoluenesulfonic acid monohydrate were added, followed by stirring at 50° C. for 1 hour. After the completion of the reaction, the solvent was distilled off under reduced pressure. The resulting solid was washed with toluene, whereby 10.8 g (yield: 86.6%) of 3-ethoxycarbonylmethylidene-4-hydroxypiperidine paratoluenesulfonate were obtained.

In 80 ml of dimethylformamide, the resulting product was dissolved, followed by the addition of 7.84 g (30.5 mmol) of α-cyclopropylcarbonyl-2-fluorobenzylbromide and 9.27 g (67.0 mmol) of potassium carbonate. The resulting mixture was stirred at room temperature for 1 hour and at 50° C. for 3 hours. After the completion of the reaction, 150 ml of water were added to the reaction mixture and the resulting mixture was extracted with ethyl acetate. The organic layer was washed with saturated saline and dried over anhydrous magnesium sulfate. The solvent was then distilled off under reduced pressure. The residue was purified by chromatography on a silica gel column (eluting solvent; toluene/ethyl acetate=9/1~4/1), whereby 7.63 g (yield: 69.3%) of the title compound were obtained as a light yellow oil.

NMR spectrum (CDCl$_3$, δ): 0.74–0.88(2H,m), 0.97–1.10 (2H,m), 1.22,1.25(total 3H, each t,J=6.8 Hz,J=7.3 Hz), 1.75–1.87(1H,m), 2.00–2.65(4H,m), 2.89–3.09(2H,m), 4.11,4.13 (total 2H, each q,J=6.8 Hz,J=7.3 Hz), 4.46,4.58 (total 1H, each d,J=13.6 Hz,J=14.1 Hz), 4.77,4.78(total 1H, each s), 6.00(1H,s), 7.05–7.43(4H, m); Mass spectrum (CI, m/z): 362 (M$^+$+1), 292.

Preparation 10

(E)-1-(2-Chloro-α-methoxycarbonylbenzyl)-3-ethoxycarbonylmethylidene-4-hydroxypiperidine In a similar manner to that described in Preparation 9(b) except for the use of 2-chloro-α-methoxycarbonylbenzylbromide instead of α-cyclopropylcarbonyl-2-fluorobenzylbromide, the reaction was effected, whereby the title compound was obtained as a yellow oil in a yield of 62.1%.

NMR spectrum (CDCl$_3$, δ): 1.10–1.35(3H,m), 1.70–1.89 (1H,m), 1.91–2.10(1H,m), 2.41–2.74(2H,m), 2.82–2.96(1H, m), 3.14(0.5H,d,J=13.9 Hz), 3.21(0.5H,d,J=13.9 Hz), 3.70, 3.71 (total 3H, each s), 4.00–4.22(2H,m), 4.52 (0.5H,d,J= 13.9 Hz), 4.61(0.5H,d,J=13.9 Hz), 4.82,4.87(total 1H, each s), 5.99,6.01 (total 1H, each s), 7.1–7.7(4H,m); Mass spectrum (CI, m/z): 368 (M$^+$+1).

Preparation 11

1-(α-Cyclopropylcarbonyl-2-fluorobenzyl)-3-(N,N-dimethylcarbamoyl)methylidene-4-hydroxypiperidine In a mixture of 75 ml of concentrated hydrochloric acid and 180 ml of acetic acid, 9.72 g (26.9 mmol) of 1-(α-cyclopropylcarbonyl-2-fluorobenzyl)-3-ethoxycarbonylmethylidene-4-hydroxypiperidine were dissolved and the resulting solution was allowed to stand at room temperature for 7 days. The reaction mixture was concentrated to dryness under reduced pressure, followed by chromatography on a silica gel column (eluting solvent: chloroform/methanol=100/3~2/1), whereby 5.11 g (yield: 57%) of 1-(α-cyclopropylcarbonyl-2-fluorobenzyl)-3-carboxymethylidene-4-hydroxypiperidine were obtained.

To the resulting product, 50 ml of methylene chloride and 3.25 g (32.2 mol) of triethylamine were added. The resulting mixture was cooled to −5° C.~0° C., followed by the dropwise addition of 1.66 g (15.3 mmol) of ethyl chlorocarbonate. The temperature of the reaction mixture was allowed to rise back to room temperature, at which stirring was carried out for 30 minutes. After cooling the reaction mixture to 10° C., 1.25 g (15.3 mmol) of dimethylamine hydrochloride and then, 1.54 g (15.3 mmol) of triethylamine were added thereto. The resulting mixture was stirred at room temperature for 5 hours. Methylene chloride—water was added to separate the methylene chloride layer. The layer so separated was dried over anhydrous magnesium sulfate and then concentrated by evaporation under reduced pressure. The residue was purified by chromatography on a silica gel column (eluting solvent: chloroform/methanol=10/3), whereby 3.56 g (yield: 64.4%) of the title compound were obtained as a light yellow oil. NMR spectrum (CDCl$_3$, δ): 0.75–0.90(2H,m), 0.93–1.06(2H,m), 1.62–1.83(1H,m), 1.85–2.10(1H,m), 2.10–2.59(2H,m), 2.75(0.5H,d,J=13.9 Hz), 2.83(0.5H,d,J=13.9 Hz), 2.89,2.92,3.04(total 6H, each s), 3.12–3.40(1H,m), 3.66(0.5H,d,J=13.9 Hz), 3.84(0.5H,d, J=13.9 Hz), 4.00–4.13(1H,m), 4.68,4.71 (total 1H, each s), 6.13(1H,s), 7.00–7.48(4H,m); Mass spectrum (CI, m/z): 361 (M$^+$+1).

Preparation 12

1-(α-Cyclopropylcarbonyl-2-fluorobenzyl)-3-(N-methylcarbamoyl)methylidene-4-hydroxypiperidine In a similar manner to Preparation 11 except for the use of methylamine hydrochloride instead of dimethylamine hydrochloride, the reaction was effected, whereby the title compound was obtained as a white solid in a yield of 55.1%.

NMR spectrum (CDCl$_3$, δ): 0.72–0.93(2H,m), 0.94–1.12 (2H,m), 1.65–1.85(1H,m), 1.85–2.12(2H,m), 2.15–2.34 (0.5H,m), 2.4–2.68(1H,m), 2.70–3.00(4.5H,m), 3.95–4.20 (2H,m), 4.79(0.5H,s), 4.85(0.5H,s), 5.96(0.5H,s), 5.97 (0.5H,s), 6.60(0.5H,br.s), 6.83(0.5H,br.s), 7.05–7.45(4H,m); Mass spectrum (CI, m/z): 347 (M$^+$+1).

Preparation 13

1-(α-Cyclopropylcarbonyl-2-fluorobenzyl)-3-ethylidene-4-hydroxypiperidine (a) 1-(t-Butoxycarbonyl)-3-ethylidene-4-piperidone A solution of 10.0 g (52.9 mmol) of 1-benzyl-4-piperidone and 4.61 g (52.9 mmol) of morpholine in 100 ml of toluene was subjected to azeotropic dehydration for 5 hours under heating and reflux by using a water separator. After the completion of the reaction, the solvent was distilled off under reduced pressure, whereby 13.7 g of 1-benzyl-4-morpholino-1,2,5,6-tetrahydropyridine were obtained in a quantitative yield. A solution of 1.52 g (34.6 mmol) of acetaldehyde in 20 ml of methylene chloride was cooled to −40° C. under an argon atmosphere, followed by the dropwise addition of 5.3 ml (43 mmol) of a boron trifluoride—ether complex and 7.44 g (28.8 mmol) of 1-benzyl-4-morpholino-1,2,5,6-tetrahydropyridine obtained above. After the completion of the dropwise addition, the temperature was raised gradually and the reaction mixture was allowed to stand overnight at room temperature. After the addition of water to terminate the reaction, the reaction mixture was extracted with methylene chloride. The organic layer was washed with saturated saline, dried over anhydrous sodium sulfate and concentrated by evaporation under reduced pressure. The residue was subjected to chromatography on a silica gel column (eluting solvent: toluene/ethyl acetate=4/1), whereby 4.68 g (yield: 69.7%) of 1-benzyl-3-(1-hydroxyethyl)-4-piperidone were obtained as a yellowish brown oil.

NMR spectrum (CDCl$_3$, δ): 1.11–1.14(3H,d,J=6 Hz), 2.35–2.95(7H,m), 3.54–3.70(2H,m), 4.02–4.22(1H,m), 7.28–7.36(5H,m).

In 100 ml of ethanol, 4.68 g (20 mmol) of the resulting 1-benzyl-3-(1-hydroxyethyl)-4-piperidone were dissolved. To the resulting solution, 0.5 g of 5% palladium-carbon were added, followed by stirring at 60° C. for 8 hours under a hydrogen gas atmosphere. After the completion of the reaction, the palladium-carbon was removed by filtration through Celite. The solvent was then distilled off under reduced pressure, whereby 2.98 g of 3-(1-hydroxyethyl)-4-piperidone were obtained as a colorless oil in a quantitative yield.

In 20 ml of methylene chloride, the resulting product was dissolved and to the resulting solution, 20 ml of a 15% aqueous potassium carbonate solution were added. Subsequent to the addition of 4.6 g (21 mmol) of di-t-butyl dicarbonate under stirring, stirring was conducted at room temperature for a further 3 hours. After the completion of the reaction, the reaction mixture was extracted with methylene chloride. The organic layer was washed with saturated saline and then dried over anhydrous sodium sulfate. The residue obtained by concentration by evaporation under reduced pressure was subjected to chromatography on a silica gel column (eluting solvent: toluene/ethyl acetate=4/1), whereby 1.86 g (yield: 38.3%) of 1-(t-butoxycarbonyl)-3-(1-hydroxyethyl)-4-piperidone was obtained as a colorless oil.

NMR spectrum (CDCl$_3$, δ): 1.21(1.5H,d,J=7 Hz), 1.25 (1.5H,d,J=6 Hz), 1.50(9H,s), 2.40–2.49(3H,m), 2.98–3.08 (0.5H,m), 3.26–3.33(1H,m), 3.40–3.90(2.5H,m), 3.95–3.98 (0.5H,m), 4.08–4.28(1.5H,m); Mass spectrum (CI, m/z): 188, 144.

To a solution of 1.86 g (7.6 mmol) of the resulting 1-(t-butoxycarbonyl)-3-(1-hydroxyethyl)-4-piperidone in 20 ml of methylene chloride, 0.77 g (7.6 mmol) of triethylamine were added. To the resulting mixture, 0.88 g (7.6 mmol) of methanesulfonyl chloride were added under ice cooling, followed by stirring at room temperature for 1 hour. The solvent was distilled off under reduced pressure. Ethyl acetate was added to the residue and the solid so precipitated was filtered off, followed by concentration by evaporation under reduced pressure. The concentrate was then dissolved in 20 ml of chloroform. To the resulting solution, 1.16 g (7.6 mmol) of 1,8-diazabicyclo[5.4.0]undec-7-ene (DBU) was added at room temperature, followed by stirring at the same temperature for 2 hours. After the completion of the reaction, the reaction mixture was concentrated by evaporation under reduced pressure and the residue was subjected to chromatography on a silica gel column (eluting solvent: toluene/ethyl acetate=19/1), whereby 1.32 g (yield: 77.2%) of the title compound was obtained as a colorless oil.

NMR spectrum (CDCl$_3$, δ): 1.49(9H,s), 1.80(3H,d,J=7 Hz), 2.54(2H,t,J=6 Hz), 3.71(2H,t,J=6 Hz), 4.35(2H,br.s), 6.86(1H,br.q); Mass spectrum (CI, m/z): 170.

(b) 1-(α-Cyclopropylcarbonyl-2-fluorobenzyl)-3-ethylidene-4-hydroxypiperidine

To a solution of 1.32 g (5.9 mmol) of 1-(t-butoxycarbonyl)-3-ethylidene-4-piperidone in 10 ml of methanol, 2.19 g (5.9 mmol) of cerium chloride 7 hydrate were added under ice cooling, followed by the addition of 0.22 g (5.9 mmol) of sodium borohydride. The resulting mixture was then stirred at room temperature for 1 hour. After removal of the solvent by distillation under reduced pressure, water was added to the residue, followed by extraction with ethyl acetate. The organic layer was dried over anhydrous sodium sulfate and concentrated by evaporation under reduced pressure. The residue was subjected to chromatography on a silica gel column (eluting solvent: chloroform), whereby 1.33 g of 1-(t-butoxycarbonyl)-3-ethylidene-4-hydroxypiperidine were obtained in a quantitative yield as a colorless oil.

NMR spectrum (CDCl$_3$, δ): 1.46(9H,s), 1.60–1.69(1H, m), 1.71 (3H,d,J=7 Hz), 1.80–1.90(1H,m), 3.50–3.65(2H, m), 4.04(1H,br.s), 4.23(1H, br.t), 5.54(1H,q,J=7 Hz); Mass spectrum (CI, m/z): 172, 154.

In 20 ml of methylene chloride, 1.51 g (6.7 mmol) of 1-(t-butoxycarbonyl)-3-ethylidene-4-hydroxypiperidine were dissolved. To the resulting solution, 5 ml of trifluoroacetic acid were added under ice cooling, followed by stirring at room temperature for 2 hours. To the reaction mixture, 11 ml of triethylamine and 1.70 g (6.7 mmol) of α-cyclopropylcarbonyl-2-fluorobenzylbromide were added under ice cooling, followed by stirring at room temperature for 2 hours. The solvent was distilled off under reduced pressure. Ethyl acetate was added to the residue and the solid so precipitated was filtered off. The filtrate was then concentrated by evaporation under reduced pressure. The residue was subjected to chromatography on a silica gel column (eluting solvent: chloroform/methanol=100/1), whereby 1.52 g (yield: 74.9%) of the title compound were obtained as a yellow oil.

NMR spectrum (CDCl$_3$, δ): 0.80–0.88(2H,m), 0.96–1.06 (2H,m), 1.23(3H,d,J=6 Hz), 2.20–2.27(3H,m), 2.40–2.73 (2H,m), 2.98–3.17(2H,m), 4.17–4.19(1H,m), 4.73(0.5H,s), 4.74(0.5H,s), 5.73(1H,br.s), 7.08–7.18(2H,m), 7.28–7.33 (1H,m), 7.41–7.48(1H,m); Mass spectrum (CI, m/z): 304 (M$^+$+1).

Preparation 14

1-(2-Fluoro-α-methoxycarbonylbenzyl)-4-hydroxypiperidine

In a similar manner to that described in Preparation 1 except for the use of 2-fluoro-α-methoxycarbonylbenzylbromide instead of α-cyclopropylcarbonyl-2-fluorobenzylbromide, the title compound was obtained as a colorless oil in a yield of 91.7%.

NMR spectrum (CDCl$_3$, δ): 1.54–1.74(2H,m), 1.83–1.97(2H,m), 2.16–2.35(2H,m), 2.73–2.88(2H,m), 3.55–3.78(1H, m), 3.70(3H,s), 4.53(1H,s), 7.02–7.53(4H,m); Mass spectrum (CI, m/z): 268 (M$^+$+1).

Test 1
Prolongation of Bleeding Time in Mice

Groups of 10 male ICR mice (Charles River Japan Inc.) were used in the experiment. Test compound suspended in 5% gum arabic solution was orally administered for 3 days (48, 24 and 4 hours before the experiment). Each mouse was placed in a retainer, and the tail was transected at 5 mm from the tip, and then the tail (2 cm) was immersed in saline solution warmed at 37° C. Bleeding time was defined as the interval between the time of transection until bleeding stopped over a 15 seconds period. Bleeding times beyond 5 minutes were recorded as 5 minutes (300 seconds). Results were expressed as ratios of bleeding times of test compound-treated to non-treated (control) groups in which mice received 5% gum arabic solution. Results are shown in Table 2.

TABLE 2

| Test compound | Test 1 (bleeding time extending ratio) | |
|---|---|---|
| | 10 mg/kg | 30 mg/kg |
| Example 1(a) | 1.06 | 2.06 |
| Example 1(b) | — | 1.46 |
| Example 10(a) | >2.75 | >2.75 |
| Example 13 | >2.75 | >2.75 |
| Example 15(a) | 2.53 | >2.75 |
| Example 18 | 1.45 | 2.57 |
| Example 28 | 1.24 | 2.16 |

Test 2
Antiaggregatory Action in Rats

Groups of 4 female SD rats (Charles River Japan Inc.) were used in the experiment Test compound suspended in 5% gum arabic solution was orally administered to rats 4 hours before the experiment. Control rats received 5% gum farabic solution. Platelet aggregation was measured according to the method of P. Lumley and P. P. A. Humphrey (*J. Pharmacol. Methods*, 6, 153–166 (1981)) with a slight modification. Blood (5.4 ml) was collected from the abdominal aorta of anesthetized rats using 3.8% (w/v) sodium citrate solution (0.6 ml) as an anticoagulant. An aliquot of citrated blood (1.2 ml) added to the cuvette was stirred (1000 rpm) at 37° C. Two minutes later, blood (0.3 ml) was taken from the cuvette, and the number of platelets was measured by an automatic hematology analyzer (E-4000, Toa Iyo Denshi), which was designated as the pre-aggregation number of platelets. To the remaining blood (0.9 ml) in the cuvette were added 0.1 ml of 0.05 mM adenosine-5'-diphosphate (ADP) or 0.06 mg/ml collagen to induce platelet aggregation. Two minutes after the addition of ADP or 4 minutes after the addition of collagen, blood (0.3 ml) was taken from the cuvette, and the number of platelets was measured, which was designated as the post-aggregation number of platelets. Platelet aggregation (%) was determined by the following equation:

100×(pre-aggregation number of platelets−post-aggregation number of platelets)/pre-aggregation number of platelets Antiaggregatory action of the test compound was determined comparing platelet aggregation of test compound-treated rats to that of control rats (without administration of test compound). Results are shown in Table 3.

TABLE 3

| Test compound | Test 2 (inhibition %) | |
|---|---|---|
| | 10 mg/kg | 30 mg/kg |
| Example 1(a) | 5.7 | 23.3 |
| Example 10(a) | 88.6 | 97.2 |
| Example 15(a) | 18.6 | 95.9 |
| Example 18 | — | 18.3 |
| Example 28 | — | 39.6 |

Test 3
Antiaggregatory Action in Human Platelets

Platelet aggregation was measured using an automatic platelet aggregometer (PAM-8C, Mebanix) by the method of G.V.R. Born (Nature, 194, 927–929 (1962)) with a slight modification. Blood was collected from the antecubital vein of healthy volunteers who had not taken any medications for 2 weeks using 3.8% sodium citrate as an anticoagulant (1/9 volume of blood). Platelet-rich plasma (PRP) was obtained by centrifugation (CR5DL, Hitachi) at 200×g for 15 minutes at room temperature. Platelet-poor plasma (PPP) was obtained by further centrifugation of the remained blood at 2000×g for 10 minutes at room temperature. The number of platelets in PRP was measured by an automatic hematology analyzer (K-1000, Toa Iyo Denshi), and adjusted to 3×10$^8$/ml using PPP. PRP prepared as described above was used for the platelet aggregation experiment. PRP (0.24 ml) was added to the cuvette and set in the platelet aggregometer. After pre-incubation for 1.5 minutes at 37° C., 0.01 ml of 0.25 mM ADP were added to the cuvette to initiate platelet aggregation. Platelet aggregation was monitored for 10 minutes.

Antiaggregatory action of test compound was expressed as inhibition (%) of aggregation comparing platelet aggregation of test compound to that of control (without addition of test compound). Results are shown in Table 4.

TABLE 4

| Test compound | Test 3 (inhibition %) | |
|---|---|---|
| | 10 μg/ml | 30 μg/ml |
| Example 1(b) | 48.6 | 70.6 |
| Example 12 | 41.2 | 68.9 |

Formulation 1
Hard Capsules

The compound (50 mg) of Example 12 in the powdery form, 128.7 mg of lactose, 70 mg of cellulose and 1.3 mg of magnesium stearate were mixed, followed by sifting through a 60-mesh sieve. The resulting powder was filled in 250-mg No.3 gelatin capsules, whereby capsules were obtained.

Formulation 2
Tablets

The compound (50 mg) of Example 12 in the powdery form, 124 mg of lactose, 25 mg of cellulose and 1 mg of magnesium stearate were mixed, followed by tableting in a tableting machine, whereby tablets, each 200 mg, were obtained. These tablets can be coated with sugar if necessary.

The compound of the formula (I) according to the present invention has excellent platelet aggregation inhibitory action or arteriosclerosis progress inhibitory action (particularly, platelet aggregation inhibitory action) and has low toxicity so that it is useful as a therapeutic agent or a preventive agent (particularly, therapeutic agent) for embolism, thrombosis or arteriosclerosis (particularly, embolism or thrombosis).

When the compound (I) or pharmaceutically acceptable salt thereof according to the present invention is used as a therapeutic agent or preventive agent for the above-described disease, it can be administered orally in the form of tablets, capsules, granules, powders or syrups, non-orally by injection or suppository by itself or mixed with a proper pharmaceutically acceptable additive such as an excipient or diluent.

The above formulations can be prepared in a well known manner by using additives. Examples of the additives may be excipients (for example, organic excipients such as sugar derivatives, e.g., lactose, sucrose, glucose, mannitol or sorbitol; starch derivatives, e.g., corn starch, potato starch, α-starch or dextrin; cellulose derivatives, e.g., crystalline cellulose; acacia; dextran; or pullulan; or inorganic excipients such as silicate derivatives, e.g., light anhydrous silicic acid, synthetic aluminum silicate, calcium silicate or magnesium aluminometasilicate; phosphate salts, e.g., calcium hydrogenphosphate; carbonates, e.g., calcium carbonate; or sulfate salts, e.g., calcium sulfate), lubricants (for example, stearic acid and metal stearates, such as calcium stearate or magnesium stearate; talc; colloidal silica; waxes such as bee gum or spermaceti; boric acid; adipic acid; sulfates such as sodium—sulfate; glycol; fumaric acid; sodium benzoate; DL leucine; lauryl sulfates such as sodium lauryl sulfate or magnesium lauryl sulfate; silicic acids such as silicic acid anhydride or silicic acid hydrate; or the above-described starch derivatives), binders (for example, hydroxypropyl cellulose, hydroxypropylmethyl cellulose, polyvinyl pyrrolidone, macrogol or the afore-mentioned excipients), decay agents (for example, cellulose derivatives such as low-substitution-degree hydroxypropyl cellulose, carboxymethyl cellulose, carboxymethyl cellulose calcium or internally crosslinked carboxymethyl cellulose sodium; or chemically-modified starches or celluloses such as carboxymethyl starch sodium, carboxymethyl starch or crosslinked polyvinylpyrrolidone), emulsifiers (for example, colloidal clay such as bentonite or bee gum; metal hydroxides such as magnesium hydroxide or aluminum hydroxide; anionic surfactants such as sodium lauryl sulfate or calcium stearate; cationic surfactants such as benzalkonium chloride; or nonionic surfactants such as a polyoxyethylene alkyl ether, a polyoxyethylene sorbitan fatty acid ester or a sucrose fatty acid ester), stabilizers (for example, paraoxybenzoates such as methylparaben or propylparaben; alcohols such as chlorobutanol, benzyl alcohol or phenylethyl alcohol; benzalkonium chloride, phenol derivatives such as phenol or cresol; thimerosal; acetic acid anhydride; or sorbic acid), taste or odor-masking agents (for example, generally used sweeteners, acidulants or flavors) and diluents.

The dose of the invention compound will vary depending on the symptoms and age of the patient. It is administered to an adult in an amount of 1 mg (preferably 10 mg) at the minimum and 1000 mg (preferably 500 mg) at the maximum in a single dose while in the case of oral administration, it is administered in an amount of 0.5 mg (preferably 5 mg) at the minimum and 500 mg (preferably 250 mg) at the maximum in a single dose in the case of intravenous administration. It is administered one to six times a day according to the symptom.

What is claimed is:

1. A cyclic amine compound having the following formula (I), or a pharmaceutically acceptable salt thereof:

wherein:
R$^1$ represents a phenyl group which may be unsubstituted or substituted by a substituent selected from the group consisting of C$_1$–C$_4$ alkyl groups, halogen atoms, fluoro-substituted-(C$_1$–C$_4$ alkyl) groups, C$_1$–C$_4$ alkoxy groups, fluoro-substituted-(C$_1$–C$_4$ alkoxy) groups, cyano groups and nitro groups;

R$^2$ is selected from the group consisting of:
C$_1$–C$_8$ aliphatic acyl groups which may be unsubstituted or substituted by a substituent selected from the group consisting of halogen atoms, hydroxyl groups, C$_1$–C$_4$ alkoxy groups and cyano groups;
benzoyl groups which may be unsubstituted or substituted by a substituent selected from the group consisting of C$_1$–C$_4$ alkyl groups, halogen atoms and C$_1$–C$_4$ alkoxy groups; and
(C$_1$–C$_4$ alkoxy)carbonyl groups;

R$^3$ represents a saturated cyclic amino group selected from the group consisting of 1-aziridinyl, 1-azetidinyl, 1-pyrrolidinyl, 1-piperidinyl, 2H-hexahydrozaepin-1-yl, 7-azabicyclo[3,1,1]heptan-7-yl, 8-azabicyclo[3,2,1]octan-8-yl, 9-azabicyclo[3,3,1]nonan-9-yl, 4-morpholinyl, 4-thiomorpholinyl and 4-piperazinyl group, which is substituted by a substituent selected from the group consisting of:
mercapto groups which are unprotected or protected by a mercapto protecting group selected from the mercapto protecting groups defined below; and
C$_1$–C$_4$ alkyl groups substituted with a mercapto group which is unprotected or protected by a group selected from the protecting groups defined below;

said mercapto protecting group is selected from the group consisting of C$_1$–C$_{20}$ alkanoyl groups, C$_3$–C$_{20}$ alkenoyl groups, benzoyl groups which are unsubstituted or substituted by a substituent selected from the group consisting of C$_1$–C$_4$ alkyl groups, halogen atoms and C$_1$–C$_4$ alkoxy groups, and (C$_1$–C$_4$ alkoxy)carbonyl groups;

and said cyclic amino group being optionally further substituted with a group of the formula =CR$^4$R$^5$, in which R$^4$ and R$^5$ are the same or different and each is independently selected from the group consisting of hydrogen atoms, C$_1$–C$_4$ alkyl groups, carboxy groups (C$_1$–C$_4$ alkoxy)carbonyl groups, carbamoyl groups and mono- and di-(C$_1$–C$_4$ alkyl)carbamoyl groups.

2. The cyclic amine compound or pharmaceutically acceptable salt thereof as defined in claim 1, wherein R$^1$ represents a substituted phenyl group (the substituent of said group being selected from the group consisting of methyl, ethyl, halogen, fluoro-substituted-methyl, methoxy, ethoxy, fluoro-substituted-methoxy, cyano and nitro).

3. The cyclic amine compound or pharmaceutically acceptable salt thereof as defined in claim 1, wherein R$^1$ represents a substituted phenyl group (the substituent of said group being selected from the group consisting of fluorine, chlorine, bromine, trifluoromethyl, difluoromethoxy, trifluoromethoxy, cyano and nitro).

4. The cyclic amine compound or pharmaceutically acceptable salt thereof as defined in claim 1, wherein $R^1$ represents a substituted phenyl group (the substituent of said group being selected from the group consisting of fluorine and chlorine).

5. The cyclic amine compound or pharmaceutically acceptable salt thereof as defined in claim 1, wherein $R^1$ represents a phenyl group which is substituted by from 1 to 3 substituents.

6. The cyclic amine compound or pharmaceutically acceptable salt thereof as defined in claim 1, wherein $R^1$ represents a phenyl group which is substituted by 1 or 2 substituents.

7. The cyclic amine compound or pharmaceutically acceptable salt thereof as defined in claim 1, wherein the position of said substituents on said substituted phenyl group represented by $R^1$ is 2 or 4.

8. The cyclic amine compound or pharmaceutically acceptable salt thereof as defined in claim 1, wherein $R^2$ is selected from the following group:

$C_2$–$C_4$ alkanoyl and ($C_3$–$C_6$ cycloalkyl)carbonyl groups, said group being unsubstituted or being substituted by a substituent selected from the group consisting of fluorine and chlorine atoms and hydroxyl, methoxy, ethoxy and cyano groups;

benzoyl groups which may be unsubstituted or substituted by a substituent selected from the group consisting of fluorine and chlorine atoms and methyl, ethyl, methoxy and ethoxy groups; and ($C_1$–$C_4$ alkoxy)carbonyl groups.

9. The cyclic amine compound or pharmaceutically acceptable salt thereof as defined in claim 1, wherein $R^2$ is selected from the group consisting of $C_2$–$C_4$ alkanoyl and ($C_3$–$C_6$ cycloalkyl)carbonyl groups which are unsubstituted or are substituted by fluorine or chlorine, benzoyl groups and ($C_1$–$C_4$ alkoxy)carbonyl groups.

10. The cyclic amine compound or pharmaceutically acceptable salt thereof as defined in claim 1, wherein $R^2$ is selected from the group consisting of acetyl, propionyl, isobutyryl, cyclopropylcarbonyl and cyclobutylcarbonyl group, said groups being unsubstituted or being substituted by fluorine, and methoxycarbonyl and ethoxycarbonyl groups.

11. The cyclic amine compound or pharmaceutically acceptable salt thereof as defined in claim 1, wherein $R^2$ is selected from the group consisting of propionyl, cyclopropylcarbonyl, methoxycarbonyl and ethoxycarbonyl groups.

12. The cyclic amine compound or pharmaceutically acceptable salt thereof as defined in claim 1, wherein $R^3$ is selected from the group consisting of:

a 3-(protected or unprotected mercapto, or protected or unprotected mercapto $C_1$–$C_4$ alkyl)-1-azetidinyl group;

a 3-(protected or unprotected mercapto, or protected or unprotected mercapto $C_1$–$C_4$ alkyl)-1-pyrrolidinyl group;

a 3- or 4-(protected or unprotected mercapto, or protected or unprotected mercapto $C_1$–$C_4$ alkyl)-1-piperidinyl group;

a 4-(protected or unprotected mercapto, or protected or unprotected mercapto $C_1$–$C_4$ alkyl)-3-(=$CR^4R^5$)-1-piperidinyl group, wherein $R^4$ and $R^5$ are the same or different and each is independently selected from the group consisting of hydrogen atoms, $C_1$–$C_4$ alkyl groups, carboxy groups, ($C_1$–$C_4$ alkoxy)carbonyl groups, carbamoyl groups, and mono- and di-($C_1$–$C_4$ alkyl)carbamoyl groups; and a 8-aza-3-(protected or unprotected mercapto, or protected or unprotected mercapto $C_1$–$C_4$ alkyl)bicyclo[3.2.1]octan-8-yl group; and said optional protecting group for said mercapto groups is selected from the group consisting of $C_1$–$C_{20}$ alkanoyl groups, $C_3$–$C_{20}$ alkenoyl groups, benzoyl groups which may be unsubstituted or substituted by a substituent selected from the group consisting of $C_1$–$C_4$ alkyl groups, halogen atoms and $C_1$–$C_4$ alkoxy groups, and ($C_1$–$C_4$ alkoxy)carbonyl groups.

13. The cyclic amine compound or pharmaceutically acceptable salt thereof as defined in claim 1, wherein $R^3$ is selected from the group consisting of:

a 3-(protected or unprotected mercapto, or protected or unprotected mercaptomethyl)-1-azetidinyl group;

a 3-(protected or unprotected mercapto, or protected or unprotected mercaptomethyl)-1-pyrrolidinyl group;

a 3- or 4-(protected or unprotected mercapto, or protected or unprotected mercaptomethyl)-1-piperidinyl group;

a 4-(protected or unprotected mercapto)-3-(=$CR^4R^5$)-1-piperidinyl group, wherein $R^4$ and $R^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and a 8-aza-3-(protected or unprotected mercapto, or protected or unprotected mercaptomethyl)bicyclo[3.2.1]octan-8-yl group; and said optional protecting group for said mercapto groups is selected from the group consisting of $C_1$–$C_{20}$ alkanoyl groups, $C_8$–$C_{20}$ alkenoyl groups, benzoyl groups which may be unsubstituted or substituted by a substituent selected from the group consisting of methyl, ethyl, fluorine, chlorine, methoxy and ethoxy, and methoxycarbonyl and ethoxycarbonyl groups.

14. The cyclic amine compound or pharmaceutically acceptable salt thereof as defined in claim 1, wherein $R^3$ is selected from the group consisting of:

a 3-(protected or unprotected mercapto)-1-azetidinyl group;

a 3-(protected or unprotected mercapto)-1-pyrrolidinyl group;

a 3- or 4-(protected or unprotected mercapto)-1-piperidinyl group;

a 4-(protected or unprotected mercapto)-3-(=$CR^4R^5$)-1-piperidinyl group, wherein $R^4$ represents a hydrogen atom and $R^5$ is selected from the group consisting of hydrogen atoms and methyl, carboxy, methoxycarbonyl, ethoxycarbonyl, carbamoyl, methylcarbamoyl and dimethylcarbamoyl groups; and a 8-aza-3-(protected or unprotected mercapto)bicyclo [3.2.1]octan-8-yl group; and said optional protecting group for said mercapto groups is selected from the group consisting of $C_2$–$C_6$ alkanoyl, palmitoleoyl, oleoyl, benzoyl, methoxycarbonyl and ethoxycarbonyl groups.

15. The cyclic amine compound or pharmaceutically acceptable salt thereof as defined in claim 1, wherein $R^3$ is selected from the group consisting of:

a 3-(protected or unprotected mercapto)-1-azetidinyl group;

a 4-(protected or unprotected mercapto)-1-piperidinyl group;

a 4-(protected or unprotected mercapto)-3-(=CR$^4$R$^5$)-1-piperidinyl group, wherein R$^4$ represents a hydrogen atom, and R$^5$ is selected from the group consisting of carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group; and said optional protecting group for said mercapto groups is selected from the group consisting of C$_2$–C$_5$ alkanoyl, benzoyl, methoxycarbonyl and ethoxycarbonyl groups.

16. The cyclic amine compound or pharmaceutically acceptable salt thereof as defined in claim 1, wherein:

R$^1$ represents a phenyl group which is substituted by from 1 to 3 substituents selected from the group consisting of methyl, ethyl, halogen, fluoro-substituted-methyl, methoxy, ethoxy, fluoro-substituted-methoxy, cyano and nitro; and R$^2$ is selected from the group consisting of:
C$_2$–C$_4$ alkanoyl and (C$_3$–C$_6$ cycloalkyl)carbonyl groups, said groups being unsubstituted or being substituted by a substituent selected from the group consisting of fluorine and chlorine atoms and hydroxyl, methoxy, ethoxy and cyano groups;
benzoyl groups which may be unsubstituted or substituted by a substituent selected from the group consisting of fluorine and chlorine atoms and methyl, ethyl, methoxy and ethoxy groups; and
(C$_1$–C$_4$ alkoxy)carbonyl groups.

17. The cyclic amine compound or pharmaceutically acceptable salt thereof as defined in claim 1, wherein:

R$^1$ represents a phenyl group which is substituted by 1 or 2 substituents selected from the group consisting of fluorine, chlorine, bromine, trifluoromethyl, difluoromethoxy, trifluoromethoxy, cyano and nitro; and R$^2$ is selected from the group consisting of C$_2$–C$_4$ alkanoyl and (C$_3$–C$_6$ cycloalkyl)carbonyl groups which are unsubstituted or are substituted by fluorine or chlorine, benzoyl groups and (C$_1$–C$_4$ alkoxy)carbonyl groups.

18. The cyclic amine compound or pharmaceutically acceptable salt thereof as defined in claim 1, wherein:

R$^1$ represents a phenyl group which is substituted at the 2- or 4-position by a substituent selected from the group consisting of fluorine, chlorine, bromine, trifluoromethyl, difluoromethoxy, trifluoromethoxy, cyano and nitro;

R$^2$ is selected from the group consisting of C$_2$–C$_4$ alkanoyl and (C$_3$–C$_6$ cycloalkyl)carbonyl groups which are unsubstituted or are substituted by fluorine or chlorine, benzoyl groups and (C$_1$–C$_4$ alkoxy)carbonyl groups; and R$^3$ is selected from the group consisting of:
a 3-(protected or unprotected mercapto, or protected or unprotected mercapto C$_1$–C$_4$ alkyl)-1-azetidinyl group;
a 3-(protected or unprotected mercapto, or protected or unprotected mercapto C$_1$–C$_4$ alkyl)-1-pyrrolidinyl group;
a 3- or 4-(protected or unprotected mercapto, or protected or unprotected mercapto C$_1$–C$_4$ alkyl)-1-piperidinyl group;
a 4-(protected or unprotected mercapto, or protected or unprotected mercapto C$_1$–C$_4$ alkyl)-3-(=CR$^4$R$^5$)-1-piperidinyl group, wherein R$^4$ and R$^5$ are the same or different and each is independently selected from the group consisting of hydrogen atoms, C$_1$–C$_4$ alkyl groups, carboxy groups, (C$_1$–C$_4$ alkoxy)carbonyl groups, carbamoyl groups, and mono- and di-(C$_1$–C$_4$ alkyl)carbamoyl groups; and a 8-aza-3-(protected or unprotected mercapto, or protected or unprotected mercapto C$_1$–C$_4$ alkyl)bicyclo[3.2.1]octan-8-yl group; and said optional protecting group for said mercapto groups is selected from the group consisting of C$_1$–C$_{20}$ alkanoyl groups, C$_3$–C$_{20}$ alkenoyl groups, benzoyl groups which may be unsubstituted or substituted by a substituent selected from the group consisting of C$_1$–C$_4$ alkyl groups, halogen atoms and C$_1$–C$_4$ alkoxy groups, and (C$_1$–C$_4$ alkoxy)carbonyl groups.

19. The cyclic amine compound or pharmaceutically acceptable salt thereof as defined in claim 1, wherein:

R$^1$ represents a phenyl group substituted at the 2- or 4-position by a fluorine or chlorine atom;

R$^2$ is selected from the group consisting of acetyl, propionyl, isobutyryl, cyclopropylcarbonyl and cyclobutylcarbonyl groups, said groups being unsubstituted or being substituted by fluorine, and methoxycarbonyl and ethoxycarbonyl groups;

R$^3$ is selected from the group consisting of:
a 3-(protected or unprotected mercapto, or protected or unprotected mercaptomethyl)-1-azetidinyl group;
a 3-(protected or unprotected mercapto, or protected or unprotected mercaptomethyl)-1-pyrrolidinyl group;
a 3- or 4-(protected or unprotected mercapto, or protected or unprotected mercaptomethyl)-1-piperidinyl group;
a 4-(protected or unprotected mercapto)-3-(=CR$^4$R$^5$)-1-piperidinyl group, wherein R$^4$ and R$^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and a 8-aza-3-(protected or unprotected mercapto, or protected or unprotected mercaptomethyl)bicyclo[3.2.1]octan-8-yl group; and said optional protecting group for said mercapto groups is selected from the group consisting of C$_1$–C$_{20}$ alkanoyl groups, C$_8$–C$_{20}$ alkenoyl groups, benzoyl groups which may be unsubstituted or may be substituted by a substituent selected from the group consisting of methyl, ethyl, fluorine, chlorine, methoxy and ethoxy, and (C$_1$–C$_4$ alkoxy)carbonyl groups.

20. The cyclic amine compound or pharmaceutically acceptable salt thereof as defined in claim 1, wherein:

R$^1$ represents a phenyl group substituted at the 2- or 4-position by a fluorine or chlorine atom;

R$^2$ is selected from the group consisting of propionyl, cyclopropylcarbonyl, methoxycarbonyl and ethoxycarbonyl groups; and R$^3$ represents:
a 3-(protected or unprotected mercapto)-1-azetidinyl group;
a 3-(protected or unprotected mercapto)-1-pyrrolidinyl group;
a 3- or 4-(protected or unprotected mercapto)-1-piperidinyl group;
a 4-(protected or unprotected mercapto)-3-(=CR$^4$R$^5$)-1-piperidinyl group wherein R$^4$ represents a hydrogen atom and R$^5$ is selected from the group consisting of hydrogen atoms and methyl, carboxy, methoxycarbonyl, ethoxycarbonyl, carbamoyl, methylcarbamoyl and dimethylcarbamoyl groups; and a 8-aza-3-(protected or unprotected mercapto)bicyclo [3.2.1]octan-8-yl group;

said optional protecting group for said mercapto groups is selected from the group consisting of $C_2$–$C_6$ alkanoyl, palmitoleoyl, oleoyl, benzoyl, methoxycarbonyl and ethoxycarbonyl groups.

21. The cyclic amine compound or pharmaceutically acceptable salt thereof as defined in claim 1, wherein:

$R^1$ represents a phenyl group substituted at the 2- or 4-position by a fluorine or chlorine atom;

$R^2$ is selected from the group consisting of propionyl, cyclopropylcarbonyl, methoxycarbonyl and ethoxycarbonyl groups; and $R^3$ represents:

a 3-(protected or unprotected mercapto)-1-azetidinyl group;

a 4-(protected or unprotected mercapto)-1-piperidinyl group;

a 4-(protected or unprotected mercapto)-3-(=$CR^4R^5$)-1-piperidinyl group, wherein $R^4$ represents a hydrogen atom and $R^5$ is selected from the group consisting of carboxy, methoxycarbonyl, ethoxycarbonyl, carbamoyl, methylcarbamoyl and dimethylcarbamoyl groups; and a 8-aza-3-(protected or unprotected mercapto)bicyclo [3.2.1]octan-8-yl group;

said optional protecting group for said mercapto groups is selected from the group consisting of $C_2$–$C_5$ alkanoyl, benzoyl, methoxycarbonyl and ethoxycarbonyl groups.

22. The cyclic amine compound of claim 1, selected from the group consisting of:

1-(α-cyclopropylcarbonyl-2-fluorobenzyl)-4-mercaptopiperidine, 1-(2-fluoro-α-methoxycarbonylbenzyl)-4-mercaptopiperidine, 1-(2-chloro-α-methoxycarbonylbenzyl)-4-mercaptopiperidine, 1-(α-cyclopropylcarbonyl-2-fluorobenzyl)-3-ethoxycarbonylmethylidene-4-mercaptopiperidine, 1-(2-chloro-α-methoxycarbonylbenzyl)-3-ethoxycarbonylmethylidene-4-mercaptopiperidine, 1-(α-cyclopropylcarbonyl-2-fluorobenzyl)-3-carboxymethylidene-4-mercaptopiperidine, 1-(2-chloro-α-methoxycarbonylbenzyl)-3-carboxymethylidene-4-mercaptopiperidine, 1-(α-cyclopropylcarbonyl-2-fluorobenzyl)-3-(N,N-dimethylcarbamoyl)methylidene-4-mercaptopiperidine, 1-(α-cyclopropylcarbonyl-2-fluorobenzyl)-3-(N-methylcarbamoyl)methylidene-4-mercaptopiperidine, 4-acetylthio-1-(α-cyclopropylcarbonyl-2-fluorobenzyl) piperidine, 4-butyrylthio-1-(α-cyclopropylcarbonyl-2-fluorobenzyl) piperidine, 1-(α-cyclopropylcarbonyl-2-fluorobenzyl)-4-pivaloylthiopiperidine, 4-benzoylthio-1-(α-cyclopropylcarbonyl-2-fluorobenzyl) piperidine, 4-acetylthio-1-(2-fluoro-α-methoxycarbonylbenzyl) piperidine, 4-benzoylthio-1-(2-fluoro-α-methoxycarbonylbenzyl) piperidine, 4-acetylthio-1-(2-chloro-α-methoxycarbonylbenzyl) piperidine, 3-acetylthio-1-(α-cyclopropylcarbonyl-2-fluorobenzyl) azetidine, 4-acetylthio-1-(α-cyclopropylcarbonyl-2-fluorobenzyl)-3-ethoxycarbonylmethylidenepiperidine, 4-acetylthio-1-(2-chloro-α-methoxycarbonylbenzyl)-3-ethoxycarbonylmethylidenepiperidine, 4-acetylthio-1-(α-cyclopropylcarbonyl-2-fluorobenzyl)-3-(N,N-dimethylcarbamoyl)methylidenepiperidine and 4-acetylthio-1-(α-cyclopropylcarbonyl-2-fluorobenzyl)-3-(N-methylcarbamoyl)methylidenepiperidine, and pharmaceutically acceptable salts thereof.

23. A pharmaceutical composition comprising an effective amount of a pharmacologically active compound together with a pharmacologically acceptable diluent or carrier, wherein said active compound is a cyclic amine compound of claim 1, or a pharmaceutically acceptable salt thereof.

24. The pharmaceutical composition according to claim 23, wherein $R^1$ represents a substituted phenyl group (the substituent of said group being selected from the group consisting of methyl, ethyl, halogen, fluoro-substituted-methyl, methoxy, ethoxy, fluoro-substituted-methoxy, cyano and nitro).

25. The pharmaceutical composition according to claim 23, wherein $R^1$ represents a substituted phenyl group (the substituent of said group being selected from the group consisting of fluorine, chlorine, bromine, trifluoromethyl, difluoromethoxy, trifluoromethoxy, cyano and nitro).

26. The pharmaceutical composition according to claim 23, wherein $R^1$ represents a substituted phenyl group (the substituent of said group being selected from the group consisting of fluorine and chlorine).

27. The pharmaceutical composition according to claim 23, wherein $R^1$ represents a phenyl group which is substituted by from 1 to 3 substituents.

28. The pharmaceutical composition according to claim 23, wherein $R^1$ represents a phenyl group which is substituted by 1 or 2 substituents.

29. The pharmaceutical composition according to claim 23, wherein the position of said substituents on said substituted phenyl group represented by $R^1$ is 2 or 4.

30. The pharmaceutical composition according to claim 23, wherein $R^2$ is selected from the following group:

$C_2$–$C_4$ alkanoyl and ($C_3$–$C_6$ cycloalkyl)carbonyl groups, said group being unsubstituted or being substituted by a substituent selected from the group consisting of fluorine and chlorine atoms and hydroxyl, methoxy, ethoxy and cyano groups;

benzoyl groups which may be unsubstituted or substituted by a substituent selected from the group consisting of fluorine and chlorine atoms and methyl, ethyl, methoxy and ethoxy groups; and ($C_1$–$C_4$ alkoxy)carbonyl groups.

31. The pharmaceutical composition according to claim 23, wherein $R^2$ is selected from the group consisting of $C_2$–$C_4$ alkanoyl and ($C_3$–$C^6$ cycloalkyl)carbonyl groups which are unsubstituted or are substituted by fluorine or chlorine, benzoyl groups and ($C_1$–$C_4$ alkoxy)carbonyl groups.

32. The pharmaceutical composition according to claim 23, wherein $R^2$ is selected from the group consisting of acetyl, propionyl, isobutyryl, cyclopropylcarbonyl and cyclobutylcarbonyl group, said groups being unsubstituted or being substituted by fluorine, and methoxycarbonyl and ethoxycarbonyl groups.

33. The pharmaceutical composition according to claim 23, wherein $R^2$ is selected from the group consisting of propionyl, cyclopropylcarbonyl, methoxycarbonyl and ethoxycarbonyl groups.

34. The pharmaceutical composition according to claim 23, wherein $R^3$ is selected from the group consisting of:

a 3-(protected or unprotected mercapto, or protected or unprotected mercapto $C_1$–$C_4$ alkyl)-1-azetidinyl group;

a 3-(protected or unprotected mercapto, or protected or unprotected mercapto $C_1$–$C_4$ alkyl)-1-pyrrolidinyl group;

a 3- or 4-(protected or unprotected mercapto, or protected or unprotected mercapto $C_1$–$C_4$ alkyl)-1-piperidinyl group;

a 4-(protected or unprotected mercapto, or protected or unprotected mercapto $C_1$–$C_4$ alkyl)-3-(=$CR^4R^5$)-1-piperidinyl group, wherein $R^4$ and $R^5$ are the same or different and each is independently selected from the group consisting of hydrogen atoms, $C_1$–$C_4$ alkyl groups, carboxy groups, ($C_1$–$C_4$ alkoxy)carbonyl groups, carbamoyl groups, and mono- and di-($C_1$–$C_4$ alkyl)carbamoyl groups; and a 8-aza-3-(protected or unprotected mercapto, or protected or unprotected mercapto $C_1$–$C_4$ alkyl)bicyclo[3.2.1]octan-8-yl group; and said optional protecting group for said mercapto groups is selected from the group consisting of $C_1$–$C_{20}$ alkanoyl groups, $C_3$–$C_{20}$ alkenoyl groups, benzoyl groups which may be unsubstituted or substituted by a substituent selected from the group consisting of $C_1$–$C_4$ alkyl groups, halogen atoms and $C_1$–$C_4$ alkoxy groups, and ($C_1$–$C_4$ alkoxy)carbonyl groups.

35. The pharmaceutical composition according to claim 23, wherein $R^3$ is selected from the group consisting of:

a 3-(protected or unprotected mercapto, or protected or unprotected mercaptomethyl)-1-azetidinyl group;

a 3-(protected or unprotected mercapto, or protected or unprotected mercaptomethyl)-1-pyrrolidinyl group;

a 3- or 4-(protected or unprotected mercapto, or protected or unprotected mercaptomethyl)-1-piperidinyl group;

a 4-(protected or unprotected mercapto)-3-(=$CR^4R^5$)-1-piperidinyl group, wherein $R^4$ and $R^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and a 8-aza-3-(protected or unprotected mercapto, or protected or unprotected mercaptomethyl)bicyclo[3.2.1]octan-8-yl group; and said optional protecting group for said mercapto groups is selected from the group consisting of $C_1$–$C_{20}$ alkanoyl groups, $C_8$–$C_{20}$ alkenoyl groups, benzoyl groups which may be unsubstituted or substituted by a substituent selected from the group consisting of methyl, ethyl, fluorine, chlorine, methoxy and ethoxy, and methoxycarbonyl and ethoxycarbonyl groups.

36. The pharmaceutical composition according to claim 23, wherein $R^3$ is selected from the group consisting of:

a 3-(protected or unprotected mercapto)-1-azetidinyl group;

a 3-(protected or unprotected mercapto)-1-pyrrolidinyl group;

a 3- or 4-(protected or unprotected mercapto)-1-piperidinyl group;

a 4-(protected or unprotected mercapto)-3-(=$CR^4R^5$)-1-piperidinyl group, wherein $R^4$ represents a hydrogen atom and $R^5$ is selected from the group consisting of hydrogen atoms and methyl, carboxy, methoxycarbonyl, ethoxycarbonyl, carbamoyl, methylcarbamoyl and dimethylcarbamoyl groups; and a 8-aza-3 -(protected or unprotected mercapto)bicyclo[3.2.1]octan-8-yl group; and said optional protecting group for said mercapto groups is selected from the group consisting of $C_2$–$C_6$ alkanoyl, palmitoleoyl, oleoyl, benzoyl, methoxycarbonyl and ethoxycarbonyl groups.

37. The pharmaceutical composition according to claim 23, wherein $R^3$ is selected from the group consisting of:

a 3-(protected or unprotected mercapto)-1-azetidinyl group;

a 4-(protected or unprotected mercapto)-1-piperidinyl group;

a 4-(protected or unprotected mercapto)-3-(=$CR^4R^5$)-1-piperidinyl group, wherein $R^4$ represents a hydrogen atom, and $R^5$ is selected from the group consisting of carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group; and said optional protecting group for said mercapto groups is selected from the group consisting of $C_2$–$C_5$ alkanoyl, benzoyl, methoxycarbonyl and ethoxycarbonyl groups.

38. The pharmaceutical composition according to claim 23, wherein:

$R^1$ represents a phenyl group which is substituted by from 1 to 3 substituents selected from the group consisting of methyl, ethyl, halogen, fluoro-substituted-methyl, methoxy, ethoxy, fluoro-substituted-methoxy, cyano and nitro; and $R^2$ is selected from the group consisting of:

$C_2$–$C_4$ alkanoyl and ($C_3$–$C_6$ cycloalkyl)carbonyl groups, said groups being unsubstituted or being substituted by a substituent selected from the group consisting of fluorine and chlorine atoms and hydroxyl, methoxy, ethoxy and cyano groups;

benzoyl groups which may be unsubstituted or substituted by a substituent selected from the group consisting of fluorine and chlorine atoms and methyl, ethyl, methoxy and ethoxy groups; and ($C_1$–$C_4$ alkoxy)carbonyl groups.

39. The pharmaceutical composition according to claim 23, wherein:

$R^1$ represents a phenyl group which is substituted by 1 or 2 substituents selected from the group consisting of fluorine, chlorine, bromine, trifluoromethyl, difluoromethoxy, trifluoromethoxy, cyano and nitro; and $R^2$ is selected from the group consisting of $C_2$–$C_4$ alkanoyl and ($C_3$–$C_6$ cycloalkyl)carbonyl groups which are unsubstituted or are substituted by fluorine or chlorine, benzoyl groups and ($C_1$–$C_4$ alkoxy)carbonyl groups.

40. The pharmaceutical composition according to claim 23, wherein:

$R^1$ represents a phenyl group which is substituted at the 2- or 4-position by a substituent selected from the group consisting of fluorine, chlorine, bromine, trifluoromethyl, difluoromethoxy, trifluoromethoxy, cyano and nitro;

$R^2$ is selected from the group consisting of $C_2-C_4$ alkanoyl and ($C_3-C_6$ cycloalkyl)carbonyl groups which are unsubstituted or are substituted by fluorine or chlorine, benzoyl groups and ($C_1-C_4$ alkoxy)carbonyl groups; and $R^3$ is selected from the group consisting of:
  a 3-(protected or unprotected mercapto, or protected or unprotected mercapto $C_1-C_4$ alkyl)-1-azetidinyl group;
  a 3-(protected or unprotected mercapto, or protected or unprotected mercapto $C_1-C_4$ alkyl)-1-pyrrolidinyl group;
  a 3- or 4-(protected or unprotected mercapto, or protected or unprotected mercapto $C_1-C_4$ alkyl)-1-piperidinyl group;
  a 4-(protected or unprotected mercapto, or protected or unprotected mercapto $C_1-C_4$ alkyl)-3-(=$CR^4R^5$)-1-piperidinyl group, wherein $R^4$ and $R^5$ are the same or different and each is independently selected from the group consisting of hydrogen atoms, $C_1-C_4$ alkyl groups, carboxy groups, ($C_1-C_4$ alkoxy)carbonyl groups, carbamoyl groups, and mono- and di-($C_1-C_4$ alkyl)carbamoyl groups; and
  a 8-aza-3-(protected or unprotected mercapto, or protected or unprotected mercapto $C_1-C_4$ alkyl)bicyclo[3.2.1]octan-8-yl group; and
  said optional protecting group for said mercapto groups is selected from the group consisting of $C_1-C_{20}$ alkanoyl groups, $C_3-C_{20}$ alkenoyl groups, benzoyl groups which may be unsubstituted or substituted by a substituent selected from the group consisting of $C_1-C_4$ alkyl groups, halogen atoms and $C_1-C_4$ alkoxy groups, and ($C_1-C_4$ alkoxy)carbonyl groups.

41. The pharmaceutical composition according to claim 23, wherein:

$R^1$ represents a phenyl group substituted at the 2- or 4-position by a fluorine or chlorine atom;

$R^2$ is selected from the group consisting of acetyl, propionyl, isobutyryl, cyclopropylcarbonyl and cyclobutylcarbonyl groups, said groups being unsubstituted or being substituted by fluorine, and methoxycarbonyl and ethoxycarbonyl groups;

$R^3$ is selected from the group consisting of:
  a 3-(protected or unprotected mercapto, or protected or unprotected mercaptomethyl)-1-azetidinyl group;
  a 3-(protected or unprotected mercapto, or protected or unprotected mercaptomethyl)-1-pyrrolidinyl group;
  a 3- or 4-(protected or unprotected mercapto, or protected or unprotected mercaptomethyl)-1-piperidinyl group;
  a 4-(protected or unprotected mercapto)-3-(=$CR^4R^5$)-1-piperidinyl group, wherein $R^4$ and $R^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and
  a 8-aza-3-(protected or unprotected mercapto, or protected or unprotected mercaptomethyl)bicyclo[3.2.1]octan-8-yl group; and
  said optional protecting group for said mercapto groups is selected from the group consisting of $C_1-C_{20}$ alkanoyl groups, $C_8-C_{20}$ alkenoyl groups, benzoyl groups which may be unsubstituted or may be substituted by a substituent selected from the group consisting of methyl, ethyl, fluorine, chlorine, methoxy and ethoxy, and ($C_1-C_4$ alkoxy)carbonyl groups.

42. The pharmaceutical composition according to claim 23, wherein:

$R^1$ represents a phenyl group substituted at the 2- or 4-position by a fluorine or chlorine atom;

$R^2$ is selected from the group consisting of propionyl, cyclopropylcarbonyl, methoxycarbonyl and ethoxycarbonyl groups; and $R^3$ represents:
  a 3-(protected or unprotected mercapto)-1-azetidinyl group;
  a 3-(protected or unprotected mercapto)-1-pyrrolidinyl group;
  a 3- or 4-(protected or unprotected mercapto)-1-piperidinyl group;
  a 4-(protected or unprotected mercapto)-3-(=$CR^4R^5$)-1-piperidinyl group wherein $R^4$ represents a hydrogen atom and $R^5$ is selected from the group consisting of hydrogen atoms and methyl, carboxy, methoxycarbonyl, ethoxycarbonyl, carbamoyl, methylcarbamoyl and dimethylcarbamoyl groups; and
  a 8-aza-3-(protected or unprotected mercapto)bicyclo[3.2.1]octan-8-yl group;
  said optional protecting group for said mercapto groups is selected from the group consisting of $C_2-C_6$ alkanoyl, palmitoleoyl, oleoyl, benzoyl, methoxycarbonyl and ethoxycarbonyl groups.

43. The pharmaceutical composition according to claim 23, wherein:

$R^1$ represents a phenyl group substituted at the 2- or 4-position by a fluorine or chlorine atom;

$R^2$ is selected from the group consisting of propionyl, cyclopropylcarbonyl, methoxycarbonyl and ethoxycarbonyl groups; and $R^3$ represents:
  a 3-(protected or unprotected mercapto)-1-azetidinyl group;
  a 4-(protected or unprotected mercapto)-1-piperidinyl group;
  a 4-(protected or unprotected mercapto)-3-(=$CR^4R^5$)-1-piperidinyl group, wherein $R^4$ represents a hydrogen atom and $R^5$ is selected from the group consisting of carboxy, methoxycarbonyl, ethoxycarbonyl, carbamoyl, methylcarbamoyl and dimethylcarbamoyl groups; and
  a 8-aza-3-(protected or unprotected mercapto)bicyclo[3.2.1]octan-8-yl group;
  said optional protecting group for said mercapto groups is selected from the group consisting of $C_2-C_5$ alkanoyl, benzoyl, methoxycarbonyl and ethoxycarbonyl groups.

44. The pharmaceutical composition according to claim 23, wherein said cyclic amine derivative is selected from the group consisting of:

1-(α-cyclopropylcarbonyl-2-fluorobenzyl)-4-mercaptopiperidine, 1-(2-fluoro-α-methoxycarbonylbenzyl)-4-mercaptopiperidine, 1-(2-chloro-α-methoxycarbonylbenzyl)-4-mercaptopiperidine, 1-(α-cyclopropylcarbonyl-2-fluorobenzyl)-3-ethoxycarbonylmethylidene-4-mercaptopiperidine, 1-(2-chloro-α-methoxycarbonylbenzyl)-3-ethoxycarbonylmethylidene-4-mercaptopiperidine, 1-(α-cyclopropylcarbonyl-2-fluorobenzyl)-3-carboxymethylidene-4-mercaptopiperidine, 1-(2-chloro-α-methoxycarbonylbenzyl)-3-carboxymethylidene-4-mercaptopiperidine, 1-(α-cyclopropylcarbonyl-2-fluorobenzyl)-3-(N,N-dimethylcarbamoyl)methylidene-4-mercaptopiperidine, 1-(α-cyclopropylcarbonyl-2-fluorobenzyl)-3-(N-methylcarbamoyl)methylidene-4-mercaptopiperidine, 4-acetylthio-1-(α-cyclopropylcarbonyl-2-fluorobenzyl) piperidine, 4-butyrylthio-1-(α-cyclopropylcarbonyl-2-fluorobenzyl) piperidine, 1-(α-cyclopropylcarbonyl-2-fluorobenzyl)-4-pivaloylthiopiperidine, 4-benzoylthio-1-(α-cyclopropylcarbonyl-2-fluorobenzyl) piperidine, 4-acetylthio-1-(2-fluoro-α-methoxycarbonylbenzyl) piperidine, 4-benzoylthio-1-(2-fluoro-α-methoxycarbonylbenzyl) piperidine, 4-acetylthio-1-(2-chloro-α-methoxycarbonylbenzyl) piperidine, 3-acetylthio-1-(α-cyclopropylcarbonyl-2-fluorobenzyl) azetidine, 4-acetylthio-1-(α-cyclopropylcarbonyl-2-fluorobenzyl)-3-ethoxycarbonylmethylidenepiperidine, 4-acetylthio-1-(2-chloro-α-methoxycarbonylbenzyl)-3-ethoxycarbonylmethylidenepiperidine, 4-acetylthio-1-(α-cyclopropylcarbonyl-2-fluorobenzyl)-3-(N,N-dimethylcarbamoyl)methylidenepiperidine and 4-acetylthio-1-(α-cyclopropylcarbonyl-2-fluorobenzyl)-3-(N-methylcarbamoyl)methylidenepiperidine, and pharmaceutically acceptable salts thereof.

45. A method for the prevention or treatment of a disease selected from the group consisting of embolism, thrombosis and arteriosclerosis, which comprises administering a pharmacologically effective amount of an active compound to a warm-blooded animal suffering from or susceptible to one of said diseases, wherein said active compound is a cyclic amine compound of claim 1, or a pharmaceutically acceptable salt thereof.

46. The method according to claim 45, wherein $R^1$ represents a substituted phenyl group (the substituent of said group being selected from the group consisting of methyl, ethyl, halogen, fluoro-substituted-methyl, methoxy, ethoxy, fluoro-substituted-methoxy, cyano and nitro).

47. The method according to claim 45, wherein $R^1$ represents a substituted phenyl group (the substituent of said group being selected from the group consisting of fluorine, chlorine, bromine, trifluoromethyl, difluoromethoxy, trifluoromethoxy, cyano and nitro).

48. The method according to claim 45, wherein $R^1$ represents a substituted phenyl group (the substituent of said group being selected from the group consisting of fluorine and chlorine).

49. The method according to claim 45, wherein $R^1$ represents a phenyl group which is substituted by from 1 to 3 substituents.

50. The method according to claim 45, wherein $R^1$ represents a phenyl group which is substituted by 1 or 2 substituents.

51. The method according to claim 45, wherein the position of said substituents on said substituted phenyl group represented by $R^1$ is 2 or 4.

52. The method according to claim 45, wherein $R^2$ is selected from the following group:

$C_2$–$C_4$ alkanoyl and ($C_3$–$C_6$ cycloalkyl)carbonyl groups, said group being unsubstituted or being substituted by a substituent selected from the group consisting of fluorine and chlorine atoms and hydroxyl, methoxy, ethoxy and cyano groups;

benzoyl groups which may be unsubstituted or substituted by a substituent selected from the group consisting of fluorine and chlorine atoms and methyl, ethyl, methoxy and ethoxy groups; and ($C_1$–$C_4$ alkoxy)carbonyl groups.

53. The method according to claim 45, wherein $R^2$ is selected from the group consisting of $C_2$–$C_4$ alkanoyl and ($C_3$–$C_6$ cycloalkyl)carbonyl groups which are unsubstituted or are substituted by fluorine or chlorine, benzoyl groups and ($C_1$–$C_4$ alkoxy)carbonyl groups.

54. The method according to claim 45, wherein $R^2$ is selected from the group consisting of acetyl, propionyl, isobutyryl, cyclopropylcarbonyl and cyclobutylcarbonyl group, said groups being unsubstituted or being substituted by fluorine, and methoxycarbonyl and ethoxycarbonyl groups.

55. The method according to claim 45, wherein $R^2$ is selected from the group consisting of propionyl, cyclopropylcarbonyl, methoxycarbonyl and ethoxycarbonyl groups.

56. The method according to claim 45, wherein $R^3$ is selected from the group consisting of:

a 3-(protected or unprotected mercapto, or protected or unprotected mercapto $C_1$–$C_4$ alkyl)-1-azetidinyl group;

a 3-(protected or unprotected mercapto, or protected or unprotected mercapto $C_1$–$C_4$ alkyl)-1-pyrrolidinyl group;

a 3- or 4-(protected or unprotected mercapto, or protected or unprotected mercapto $C_1$–$C_4$ alkyl)-1-piperidinyl group;

a 4-(protected or unprotected mercapto, or protected or unprotected mercapto $C_1$–$C_4$ alkyl)-3-(=$CR^4R^5$)-1-piperidinyl group, wherein $R^4$ and $R^5$ are the same or different and each is independently selected from the group consisting of hydrogen atoms, $C_1$–$C_4$ alkyl groups, carboxy groups, ($C_1$–$C_4$ alkoxy)carbonyl groups, carbamoyl groups, and mono- and di-($C_1$–$C_4$ alkyl)carbamoyl groups; and a 8-aza-3-(protected or unprotected mercapto, or protected or unprotected mercapto $C_1$–$C_4$ alkyl)bicyclo [3.2.1]octan-8-yl group; and said optional protecting group for said mercapto groups is selected from the group consisting of $C_1$–$C_{20}$ alkanoyl groups, $C_3$–$C_{20}$ alkenoyl groups, benzoyl groups which may be unsubstituted or substituted by a substituent selected from the group consisting of $C_1$–$C_4$ alkyl groups, halogen atoms and $C_1$–$C_4$ alkoxy groups, and ($C_1$–$C_4$ alkoxy)carbonyl groups.

57. The method according to claim 45, wherein $R^3$ is selected from the group consisting of:

a 3-(protected or unprotected mercapto, or protected or unprotected mercaptomethyl)-1-azetidinyl group;

a 3-(protected or unprotected mercapto, or protected or unprotected mercaptomethyl)-1-pyrrolidinyl group;

a 3- or 4-(protected or unprotected mercapto, or protected or unprotected mercaptomethyl)-1-piperidinyl group;

a 4-(protected or unprotected mercapto)-3-(=CR$^4$R$^5$)-1-piperidinyl group, wherein R$^4$ and R$^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and a 8-aza-3-(protected or unprotected mercapto, or protected or unprotected mercaptomethyl)bicyclo[3.2.1]octan-8-yl group; and said optional protecting group for said mercapto groups is selected from the group consisting of C$_1$–C$_{20}$ alkanoyl groups, C$_8$–C$_{20}$ alkenoyl groups, benzoyl groups which may be unsubstituted or substituted by a substituent selected from the group consisting of methyl, ethyl, fluorine, chlorine, methoxy and ethoxy, and methoxycarbonyl and ethoxycarbonyl groups.

58. The method according to claim 45, wherein R$^3$ is selected from the group consisting of:

a 3-(protected or unprotected mercapto)-1-azetidinyl group;

a 3-(protected or unprotected mercapto)-1-pyrrolidinyl group;

a 3- or 4-(protected or unprotected mercapto)-1-piperidinyl group;

a 4-(protected or unprotected mercapto)-3-(=CR$^4$R$^5$)-1-piperidinyl group, wherein R$^4$ represents a hydrogen atom and R$^5$ is selected from the group consisting of hydrogen atoms and methyl, carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group; and said optional protecting group for said mercapto groups is selected from the group consisting of C$_2$–C$_6$ alkanoyl, palmitoleoyl, oleoyl, benzoyl, methoxycarbonyl and ethoxycarbonyl groups.

59. The method according to claim 45, wherein R$^3$ is selected from the group consisting of:

a 3-(protected or unprotected mercapto)-1-azetidinyl group;

a 4-(protected or unprotected mercapto)-1-piperidinyl group;

a 4-(protected or unprotected mercapto)-3-(=CR$^4$R$^5$)-1-piperidinyl group, wherein R$^4$ represents a hydrogen atom, and R$^5$ is selected from the group consisting of carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group; and said optional protecting group for said mercapto groups is selected from the group consisting of C$_2$–C$_5$ alkanoyl, benzoyl, methoxycarbonyl and ethoxycarbonyl groups.

60. The method according to claim 45, wherein:

R$^1$ represents a phenyl group which is substituted by from 1 to 3 substituents selected from the group consisting of methyl, ethyl, halogen, fluoro-substituted-methyl, methoxy, ethoxy, fluoro-substituted-methoxy, cyano and nitro; and R$^2$ is selected from the group consisting of:

C$_2$–C$_4$ alkanoyl and (C$_3$–C$_6$ cycloalkyl)carbonyl groups, said groups being unsubstituted or being substituted by a substituent selected from the group consisting of fluorine and chlorine atoms and hydroxyl, methoxy, ethoxy and cyano groups;

benzoyl groups which may be unsubstituted or substituted by a substituent selected from the group consisting of fluorine and chlorine atoms and methyl, ethyl, methoxy and ethoxy groups; and (C$_1$–C$_4$ alkoxy)carbonyl groups.

61. The method according to claim 45, wherein:

R$^1$ represents a phenyl group which is substituted by 1 or 2 substituents selected from the group consisting of fluorine, chlorine, bromine, trifluoromethyl, difluoromethoxy, trifluoromethoxy, cyano and nitro; and R$^2$ is selected from the group consisting of C$_2$–C$_4$ alkanoyl and (C$_3$–C$_6$ cycloalkyl)carbonyl groups which are unsubstituted or are substituted by fluorine or chlorine, benzoyl groups and (C$_1$–C$_4$ alkoxy)carbonyl groups.

62. The method according to claim 45, wherein:

R$^1$ represents a phenyl group which is substituted at the 2- or 4-position by a substituent selected from the group consisting of fluorine, chlorine, bromine, trifluoromethyl, difluoromethoxy, trifluoromethoxy, cyano and nitro;

R$^2$ is selected from the group consisting of C$_2$–C$_4$ alkanoyl and (C$_3$–C$_6$ cycloalkyl)carbonyl groups which are unsubstituted or are substituted by fluorine or chlorine, benzoyl groups and (C$_1$–C$_4$ alkoxy)carbonyl groups; and R$^3$ is selected from the group consisting of:

a 3-(protected or unprotected mercapto, or protected or unprotected mercapto C$_1$–C$_4$ alkyl)-1-azetidinyl group;

a 3-(protected or unprotected mercapto, or protected or unprotected mercapto C$_1$–C$_4$ alkyl)-1-pyrrolidinyl group;

a 3- or 4-(protected or unprotected mercapto, or protected or unprotected mercapto C$_1$–C$_4$ alkyl)-1-piperidinyl group;

a 4-(protected or unprotected mercapto, or protected or unprotected mercapto C$_1$–C$_4$ alkyl)-3-(=CR$^4$R$^5$)-1-piperidinyl group, wherein R$^4$ and R$^5$ are the same or different and each is independently selected from the group consisting of hydrogen atoms, C$_1$–C$_4$ alkyl groups, carboxy groups, (C$_1$–C$_4$ alkoxy)carbonyl groups, carbamoyl groups, and mono- and di-(C$_1$–C$_4$ alkyl)carbamoyl groups; and a 8-aza-3-(protected or unprotected mercapto, or protected or unprotected mercapto C$_1$–C$_4$ alkyl)bicyclo[3.2.1]octan-8-yl group; and said optional protecting group for said mercapto groups is selected from the group consisting of C$_1$–C$_{20}$ alkanoyl groups, C$_3$–C$_{20}$ alkenoyl groups, benzoyl groups which may be unsubstituted or substituted by a substituent selected from the group consisting of C$_1$–C$_4$ alkyl groups, halogen atoms and C$_1$–C$_4$ alkoxy groups, and (C$_1$–C$_4$ alkoxy)carbonyl groups.

63. The method according to claim 45, wherein:

R$^1$ represents a phenyl group substituted at the 2- or 4-position by a fluorine or chlorine atom;

R$^2$ is selected from the group consisting of acetyl, propionyl, isobutyryl, cyclopropylcarbonyl and cyclobutylcarbonyl groups, said groups being unsubstituted or being substituted by fluorine, and methoxycarbonyl and ethoxycarbonyl groups;

R$^3$ is selected from the group consisting of:

a 3-(protected or unprotected mercapto, or protected or unprotected mercaptomethyl)-1-azetidinyl group;

a 3-(protected or unprotected mercapto, or protected or unprotected mercaptomethyl)-1-pyrrolidinyl group;

a 3- or 4-(protected or unprotected mercapto, or protected or unprotected mercaptomethyl)-1-piperidinyl group;

a 4-(protected or unprotected mercapto)-3-(=$CR^4R^5$)-1-piperidinyl group, wherein $R^4$ and $R^5$ are the same or different and each is independently selected from the group consisting of hydrogen atoms and methyl, ethyl, carboxy, methoxycarbonyl, ethoxycarbonyl, carbamoyl, methylcarbamoyl, ethylcarbamoyl, dimethylcarbamoyl and diethylcarbamoyl groups; and a 8-aza-3-(protected or unprotected mercapto, or protected or unprotected mercaptomethyl)bicyclo[3.2.1]octan-8-yl group; and said optional protecting group for said mercapto groups is selected from the group consisting of $C_1$–$C_{20}$ alkanoyl groups, $C_8$–$C_{20}$ alkenoyl groups, benzoyl groups which may be unsubstituted or may be substituted by a substituent selected from the group consisting of methyl, ethyl, fluorine, chlorine, methoxy and ethoxy, and ($C_1$–$C_4$ alkoxy)carbonyl groups.

64. The method according to claim 45, wherein:

$R^1$ represents a phenyl group substituted at the 2- or 4-position by a fluorine or chlorine atom;

$R^2$ is selected from the group consisting of propionyl, cyclopropylcarbonyl, methoxycarbonyl and ethoxycarbonyl groups; and $R^3$ represents:

a 3-(protected or unprotected mercapto)-1-azetidinyl group;

a 3-(protected or unprotected mercapto)-1-pyrrolidinyl group;

a 3- or 4-(protected or unprotected mercapto)-1-piperidinyl group;

a 4-(protected or unprotected mercapto)-3-(=$CR^4R^5$)-1-piperidinyl group wherein $R^4$ represents a hydrogen atom and $R^5$ is selected from the group consisting of hydrogen atoms and methyl, carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group;

said optional protecting group for said mercapto groups is selected from the group consisting of $C_2$–$C_6$ alkanoyl, palmitoleoyl, oleoyl, benzoyl, methoxycarbonyl and ethoxycarbonyl groups.

65. The method according to claim 45, wherein:

$R^1$ represents a phenyl group substituted at the 2- or 4-position by a fluorine or chlorine atom;

$R^2$ is selected from the group consisting of propionyl, cyclopropylcarbonyl, methoxycarbonyl and ethoxycarbonyl groups; and $R^3$ represents:

a 3-(protected or unprotected mercapto)-1-azetidinyl group;

a 4-(protected or unprotected mercapto)-1-piperidinyl group;

a 4-(protected or unprotected mercapto)-3-(=$CR^4R^5$)-1-piperidinyl group, wherein $R^4$ represents a hydrogen atom and $R^5$ is selected from the group consisting of carboxy, methoxycarbonyl, ethoxycarbonyl, carbamoyl, methylcarbamoyl and dimethylcarbamoyl groups; and a 8-aza-3-(protected or unprotected mercapto)bicyclo[3.2.1]octan-8-yl group;

said optional protecting group for said mercapto groups is selected from the group consisting of $C_2$–$C_5$ alkanoyl, benzoyl, methoxycarbonyl and ethoxycarbonyl groups.

66. The method according to claim 45, wherein said cyclic amine is selected from the group consisting of:

1-(α-cyclopropylcarbonyl-2-fluorobenzyl)-4-mercaptopiperidine, 1-(2-fluoro-α-methoxycarbonylbenzyl)-4-mercaptopiperidine, 1-(2-chloro-α-methoxycarbonylbenzyl)-4-mercaptopiperidine, 1-(α-cyclopropylcarbonyl-2-fluorobenzyl)-3-ethoxycarbonylmethylidene-4-mercaptopiperidine, 1-(2-chloro-α-methoxycarbonylbenzyl)-3-ethoxycarbonylmethylidene-4-mercaptopiperidine, 1-(α-cyclopropylcarbonyl-2-fluorobenzyl)-3-carboxymethylidene-4-mercaptopiperidine, 1-(2-chloro-α-methoxycarbonylbenzyl)-3-carboxymethylidene-4-mercaptopiperidine, 1-(α-cyclopropylcarbonyl-2-fluorobenzyl)-3-(N,N-dimethylcarbamoyl)methylidene-4-mercaptopiperidine, 1-(α-cyclopropylcarbonyl-2-fluorobenzyl)-3-(N-methylcarbamoyl)methylidene-4-mercaptopiperidine, 4-acetylthio-1-(α-cyclopropylcarbonyl-2-fluorobenzyl)piperidine, 4-butyrylthio-1-(α-cyclopropylcarbonyl-2-fluorobenzyl)piperidine, 1-(α-cyclopropylcarbonyl-2-fluorobenzyl)-4-pivaloylthiopiperidine, 4-benzoylthio-1-(α-cyclopropylcarbonyl-2-fluorobenzyl)piperidine, 4-acetylthio-1-(2-fluoro-α-methoxycarbonylbenzyl)piperidine, 4-benzoylthio-1-(2-fluoro-α-methoxycarbonylbenzyl)piperidine, 4-acetylthio-1-(2-chloro-α-methoxycarbonylbenzyl)piperidine, 3-acetylthio-1-(α-cyclopropylcarbonyl-2-fluorobenzyl)azetidine, 4-acetylthio-1-(α-cyclopropylcarbonyl-2-fluorobenzyl)-3-ethoxycarbonylmethylidenepiperidine, 4-acetylthio-1-(2-chloro-α-methoxycarbonylbenzyl)-3-ethoxycarbonylmethylidenepiperidine, 4-acetylthio-1-(α-cyclopropylcarbonyl-2-fluorobenzyl)-3-(N,N-dimethylcarbamoyl)methylidenepiperidine and 4-acetylthio-1-(α-cyclopropylcarbonyl-2-fluorobenzyl)-3-(N-methylcarbamoyl)methylidenepiperidine, and pharmaceutically acceptable salts thereof.

67. The method according to claim 45, wherein said disease to be prevented or treated is embolism.

68. The method according to claim 45, wherein said disease to be prevented or treated is thrombosis.

69. The method according to claim 45, wherein said disease to be prevented or treated is arteriosclerosis.

70. The compound of claim 1, wherein:

$R^1$ represents a phenyl group which is unsubstituted or substituted by a substituent selected from the group consisting of $C_1$–$C_4$ alkyl groups, halogen atoms, fluoro-substituted-($C_1$–$C_4$ alkyl) groups, $C_1$–$C_4$ alkoxy groups, fluoro-substituted-($C_1$–$C_4$ alkoxy) groups, cyano groups and nitro groups;

$R^2$ is selected from the group consisting of:
$C_1$–$C_8$ aliphatic acyl groups which is unsubstituted or substituted by a substituent selected from the group consisting of halogen atoms, hydroxyl groups, $C_1$–$C_4$ alkoxy groups and cyano groups;
benzoyl groups which may be unsubstituted or substituted by a substituent selected from the group consisting of $C_1$–$C_4$ alkyl groups, halogen atoms and $C_1$–$C_4$ alkoxy groups; and
($C_1$–$C_4$ alkoxy)carbonyl groups;

$R^3$ represents a 1-azetidinyl, 1-pyrrolidinyl, 1-piperidinyl or 8-azabicyclo[3,2,1]octan-8-yl group which is substituted by a substituent selected from the group defined below and which is optionally substituted by a group of the formula =$CR^4R^5$, in which $R^4$ and $R^5$ are the same or different and each is independently selected from the substituent group consisting of hydrogen atoms, $C_1$–$C_4$ alkyl groups, carboxy groups, ($C_1$–$C_4$ alkoxy)carbonyl groups, carbamoyl groups and mono- and di-($C_1$–$C_4$ alkyl)carbamoyl groups;

said substituent group is selected from the group consisting of:
mercapto groups which are unprotected or protected by a group selected from the protecting groups defined below; and
$C_1$–$C_4$ alkyl groups substituted with a mercapto group which is unprotected or protected by a group selected from the mercapto protecting groups defined below;
said mercapto protecting group is selected from the group consisting of $C_1$–$C_{20}$ alkanoyl groups, $C_3$–$C_{20}$ alkenoyl groups, benzoyl groups which may be unsubstituted or substituted by a substituent selected from the group consisting of $C_1$–$C_4$ alkyl groups, halogen atoms and $C_1$–$C_4$ alkoxy groups, and ($C_1$–$C_4$ alkoxy)carbonyl groups;

or a pharmaceutically acceptable salt thereof.

* * * * *